US008119614B2

(12) United States Patent
Dolezal et al.

(10) Patent No.: US 8,119,614 B2
(45) Date of Patent: Feb. 21, 2012

(54) SUBSTITUTION DERIVATIVES OF N⁶-BENZYLADENOSINE, METHODS OF THEIR PREPARATION, THEIR USE FOR PREPARATION OF DRUGS, COSMETIC PREPARATIONS AND GROWTH REGULATORS, PHARMACEUTICAL PREPARATIONS, COSMETIC PREPARATIONS AND GROWTH REGULATORS CONTAINING THESE COMPOUNDS

(75) Inventors: Karel Dolezal, Vidce (CZ); Igor Popa, Olomouc (CZ); Marek Zatloukal, Sumperk (CZ); René Lenobel, Stemberk (CZ); Dana Hradecká, Praha (CZ); Borivoj Vojtesek, Modrice (CZ); Stjepan Uldrijan, Brno (CZ); Petr Mlejnek, Brno (CZ); Stefaan Werbrouck, Harelbeke (BE); Miroslav Strnad, Olomouc (CZ)

(73) Assignee: Ustav Experimentalni Botaniky Akademie Ved Ceske Republiky, Prague (CZ)

(*) Notice: Subject to any disclaimer, the term of this patent is extended or adjusted under 35 U.S.C. 154(b) by 158 days.

(21) Appl. No.: 10/540,993

(22) PCT Filed: Dec. 29, 2003

(86) PCT No.: PCT/CZ03/00078
§ 371 (c)(1),
(2), (4) Date: Aug. 15, 2005

(87) PCT Pub. No.: WO2004/058791
PCT Pub. Date: Jul. 15, 2004

(65) Prior Publication Data
US 2006/0166925 A1   Jul. 27, 2006

(30) Foreign Application Priority Data
Dec. 30, 2002 (CZ) .............................. PV 2002-4273

(51) Int. Cl.
C07H 19/167 (2006.01)
C07H 19/173 (2006.01)
A01N 43/04 (2006.01)
A61K 31/70 (2006.01)
A61K 8/02 (2006.01)

(52) U.S. Cl. ........ 514/46; 514/45; 536/27.6; 536/27.62; 424/401

(58) Field of Classification Search .............. 536/27.1, 536/27.13, 27.2, 27.21; 514/45, 46
See application file for complete search history.

(56) References Cited

U.S. PATENT DOCUMENTS

| 3,506,643 | A | * | 4/1970 | Dietmann et al. | 536/27.62 |
| 3,551,409 | A | * | 12/1970 | Dietmann et al. | 536/27.63 |
| 3,781,273 | A | | 12/1973 | Kampe et al. | |
| 3,817,981 | A | * | 6/1974 | Kampe et al. | 536/27.62 |
| 3,845,035 | A | * | 10/1974 | Kampe et al. | 536/27.61 |
| 4,514,405 | A | * | 4/1985 | Irmscher et al. | 514/46 |
| 5,773,423 | A | * | 6/1998 | Jacobson et al. | 514/45 |

FOREIGN PATENT DOCUMENTS
EP   0 540 854   5/1993

OTHER PUBLICATIONS

Bressi et al. (J. Med. Chem., vol. 43, 2000, pp. 4135-4150).*
Hewett et al. "Cytokinins in Populus x robusta", Planta (1973) 114(2), 119-29.*
Golisade et al. "Anti-Malarial Activity of N6-Substituted Adenosine Derivatives", Bioorganic and Medicinal Chemistry, vol. 10, Mar. 2002, pp. 769-777.*
Dutta, S.P., et al., "Synthesis and Biological Activities of Some N-(Nitro-Aminobenzyl) Adenosines", Journal of Medicinal Chemistry, American Chemical Society, Washington, US vol. 18, No. 8, 1975.
Bressi, J C, et al., "Adenosine Analogues As Inhibitors of Trypanosoma Brucei Phosphoglycerate Kinase: Elucidation of a Novel Binding Mode for A 2-Amino-N6-Substituted Adenosine", Journal of Medicinal Chemistry, American Chemical Society, Washington, US, vol. 43, No. 22, 2000.
Fleysher M.H., et al., "Synthesis and Biological Activity of Some New N6-Substituted Purine Nucleosides", J. Med. Chem., vol. 12, 1969, pp. 1056-1061.
Wanner, M J, et al., "2-Netro Analogues of Adenosine and 1-Deazaadenosine: Synthesis and Binding Studies at the Adenosine A1, A2A and A3 Receptor Subtypes", Bioorganic & Medicinal Chemistry Letters. Oxford, GB, vol. 10, No. 18, Sep. 2000.
Trivedi, B K, et al., "C2N6-Disubstituted Adenosines: Synthesis and Structure-Activity Relationships", Journal of Medicinal Chemistry, American Chemical Society, Washington, US, vol. 32, 1989, pp. 1667-1673.
Magyar-Tabori, K., et al., "High in Vitro Shoot Proliferation in the Apple Cultivar Jonagold induced by Benzyladenine Analogues", ACTA Agronomica Hungarica, vol. 50, 2002, pp. 191-195.

* cited by examiner

*Primary Examiner* — Traviss C McIntosh, III
(74) *Attorney, Agent, or Firm* — Notaro, Michalos & Zaccaria P.C.

(57) ABSTRACT

The invention concerns novel substitution derivatives of N⁶-benzyladenosine having anticancer, mitotic, immunosuppressive and antisenescent properties for plant, animal and human cells. This invention also relates to the methods of preparation of these N⁶-benzyladenosine derivatives and their use as drugs, cosmetic preparations and growth regulators comprising these derivatives as active compound and use of these derivatives for preparation of pharmaceutical compositions, in biotechnological processes, in cosmetics and in agriculture.

4 Claims, 16 Drawing Sheets

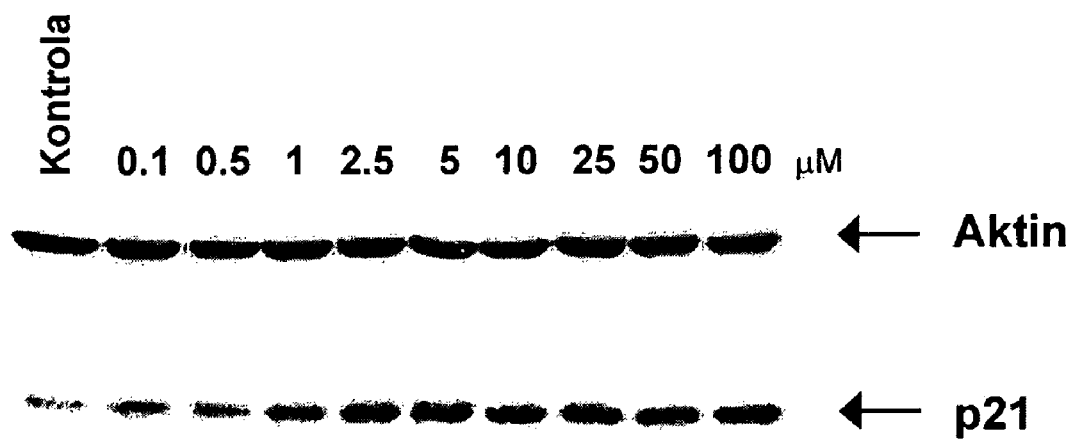
Fig.1: Protein p21$^{WAF-1}$ induction in MCF-7 cells after treatment by different concentrations of 2OH3MeOBAPR.
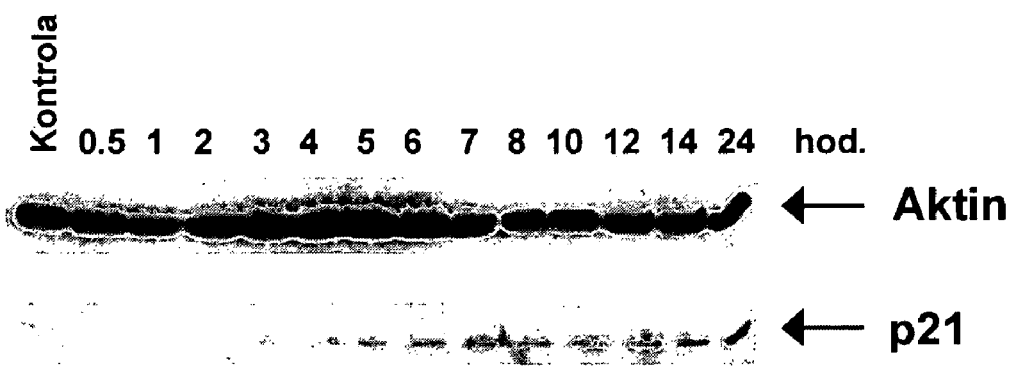
Fig. 2

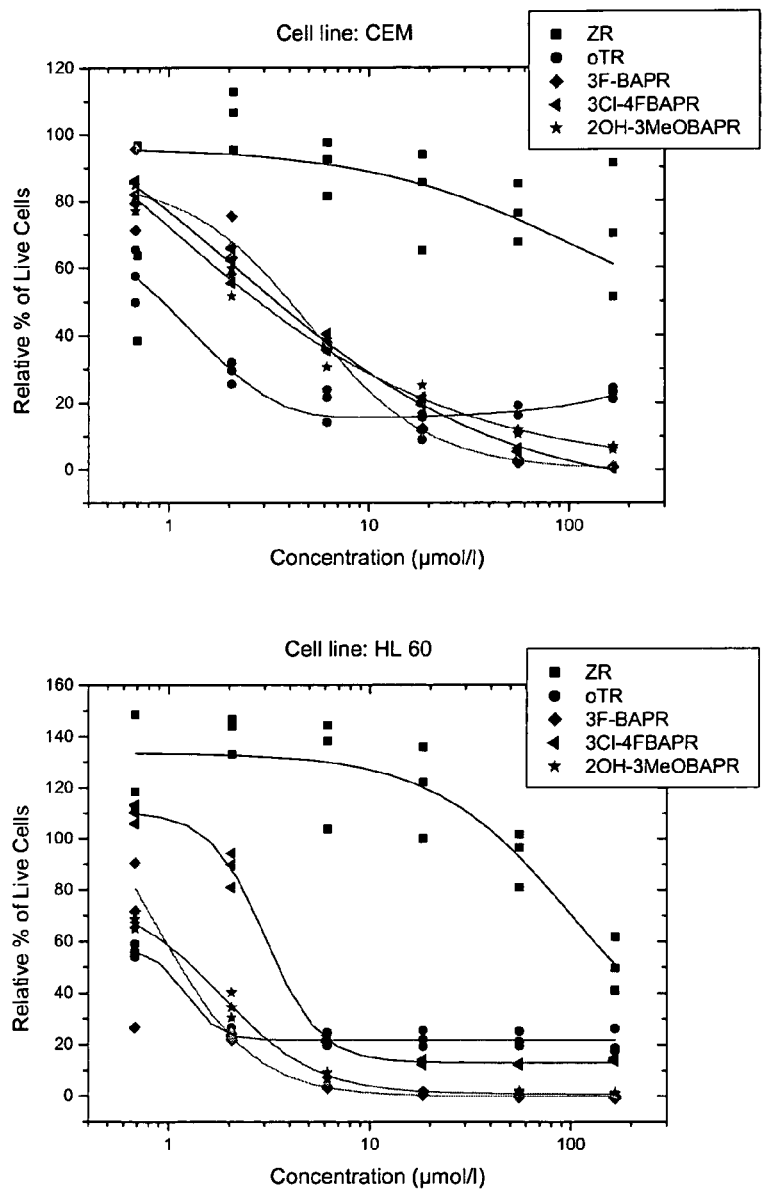

Fig. 3: Inhibition of growth of carcinoma cell line CEM (A) and HL60 (B) by new cytokinins. Cytotoxicity was measured using Calcein AM assay. Activity is presented as percentage of maximal activity (in absence of inhibitors). ZR: zeatin riboside; oTR: *ortho*-topolin riboside; 3F-BAPR: 6-(3-fluorobenzylamino)purine riboside; 3Cl-4FBAPR: 6-(3-chloro-4-fluorobenzylamino)purine riboside; 2OH3MeOBAPR: 6-(2-hydroxy-3-methoxybenzylamino)purine riboside.

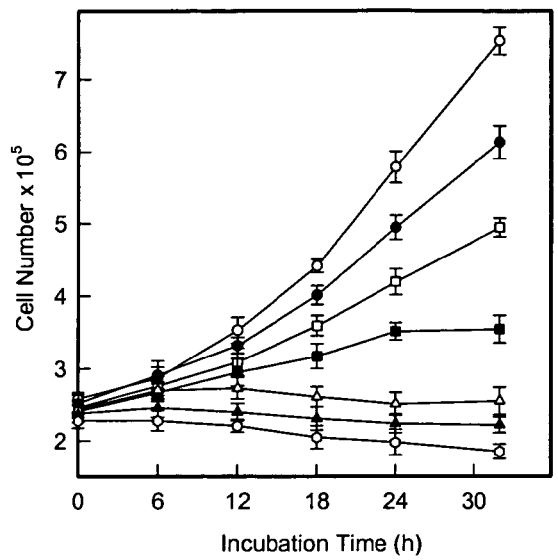
Fig. 4. Inhibition of HL-60 cell proliferation induced by 2OH3MeOBAPR. 2OH3MeOBAPR was added to the exponentially growing cells in following concentrations: 2.5μM (●), 5μM (□), 10μM (■), 20μM (△), 40μM (▲) and 60μM (◐). Control cells cultivated on standard media without 2OH3MeOBAPR (○).

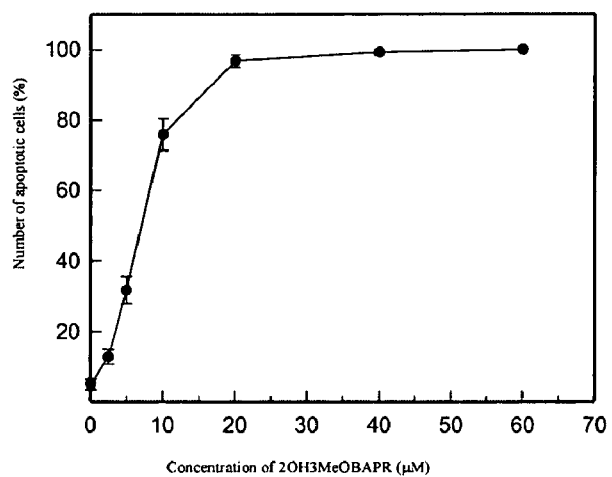
Fig. 5. Induction of apoptosis by 2OH3MeOBAPR in HL-60 cells. Different concentrations of 2OH3MeOBAPR were added to the exponentially growing cells. Number of apoptotic cells (with respect to the nucleus morphology) was monitored after 24 h of incubation. Control cells were cultivated on standard media without 2OH3MeOBAPR.

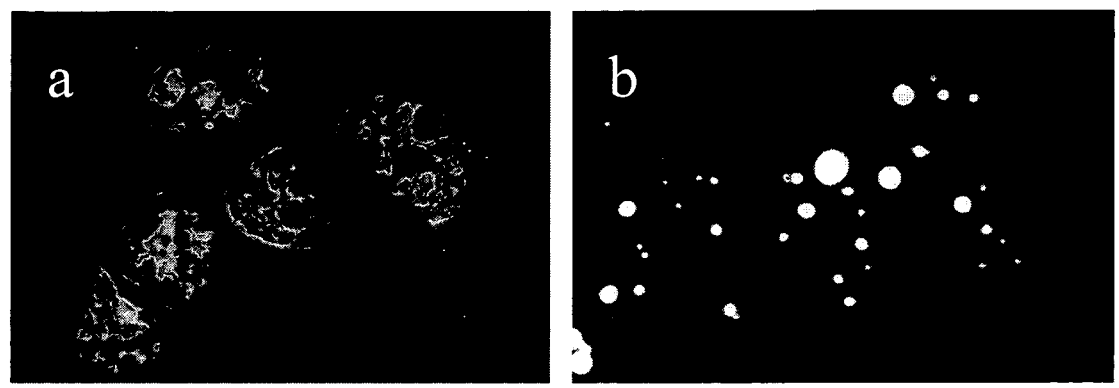
Fig. 6. Effect of 2OH3MeOBAPR on HL-60 cell nuclear morphology. Nuclei of cells cultivated at standard conditions on media without 2OH3MeOBAPR a), nuclei of cells cultivated on media containing 5 µM 2OH3MeOBAPR for 24 hours b)

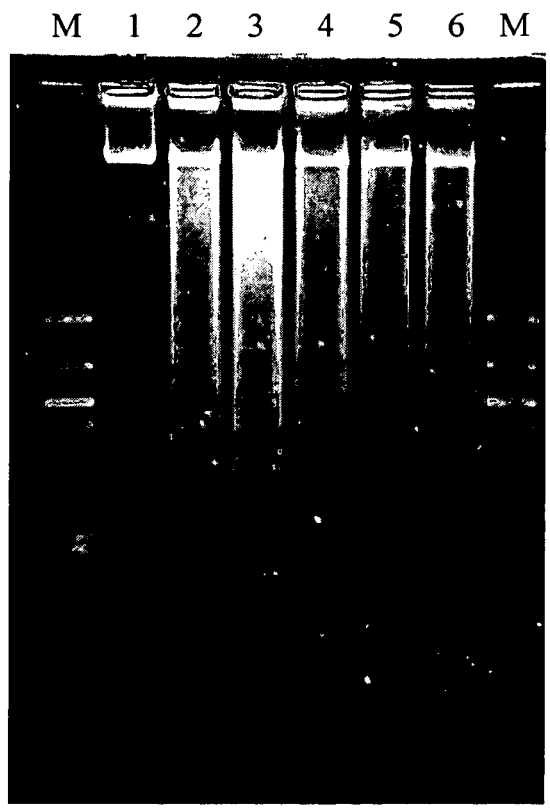
Fig. 7. Effect of 2OH3MeOBAPR on nuclear DNA integrity of HL-60 cells. M – molecular weight standards. Line 1- DNA isolated from cells cultivated on media without 2OH3MeOBAPR. Line 2-6 DNA isolated from cells cultivated on media containing 5, 10, 20 40 and 60 μM 2OH3MeOBAPR for 24 h.

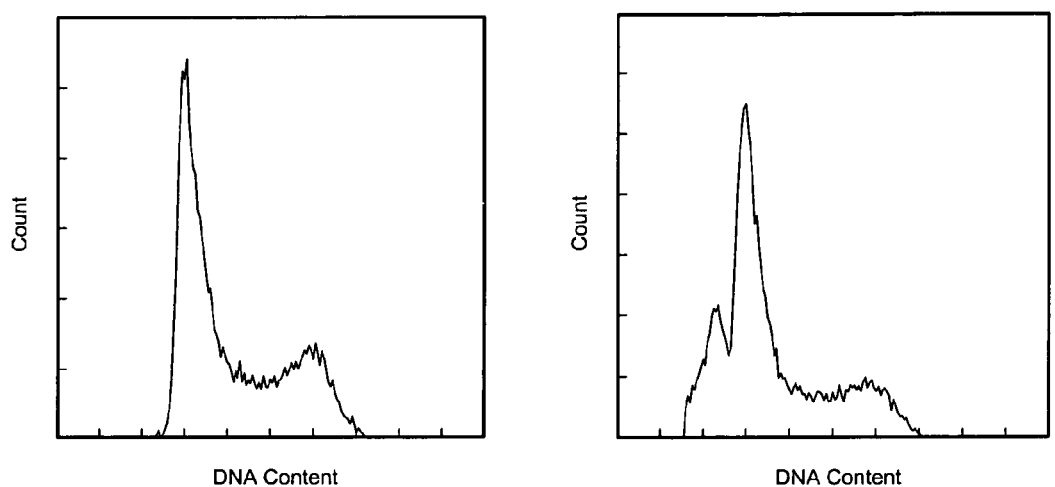
Fig. 8. Effect of 2OH3MeOBAPR (6-(2-hydroxy-3-methoxybenzylamino)purine riboside) on cell cycle. Cells were cultivated a) in standard media without 2OH3MeOBAPR (control), b) in media containing 5 μM 2OH3MeOBAPR for 24h prior analysis by flow-cytometry.

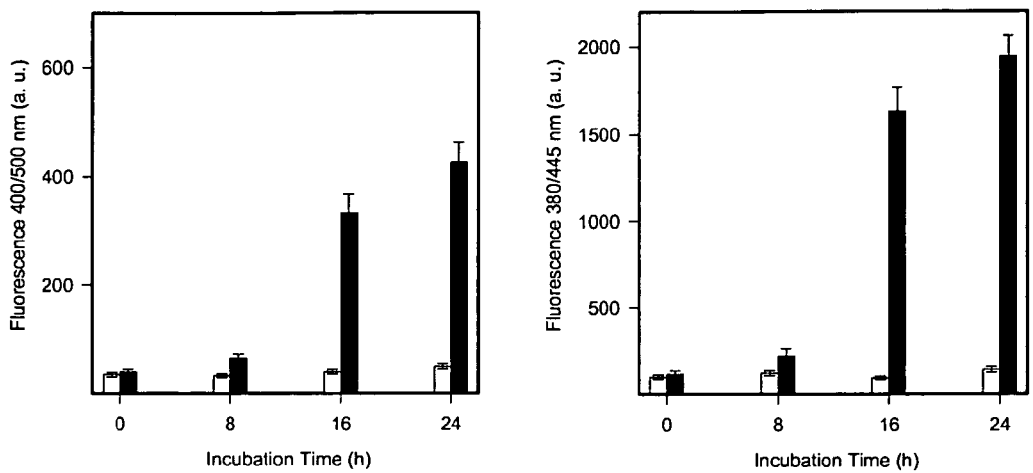
Fig. 9. Effect of 2OH3MeOBAPR on caspase proteases. Cells cultivated in standard media without 2OH3MeOBAPR (white bars), Cells cultivated in media containing 20 μM 2OH3MeOBAPR (black bars). Relative substrate hydrolysis for caspase-9 Ac-LEHD-AFC a) and caspase-3 Ac-DEVD-AMC b).

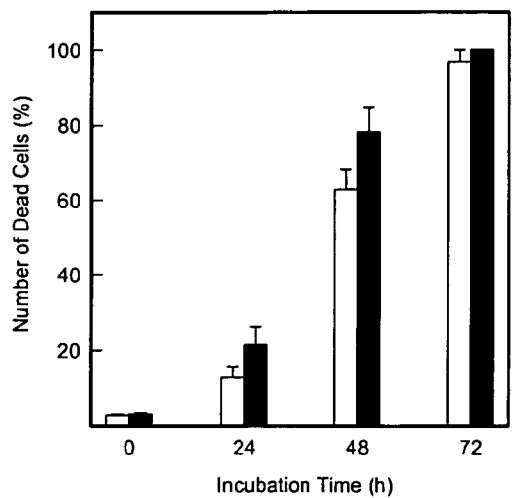
Fig. 10: Effect of caspase inhibitor Z-VAD-FMK on viability HL-60 cells cultivated in presence of 2OH3MeOBAPR. Exponentially growing cells were cultivated for 72h with 20 µM 2OH3MeOBAPR (white bars) and combination of 20 µM 2OH3MeOBAPR and 50µM Z-VAD-FMK (black bars). Cell viability was measured during the incubation using combined FDA/PI staining.

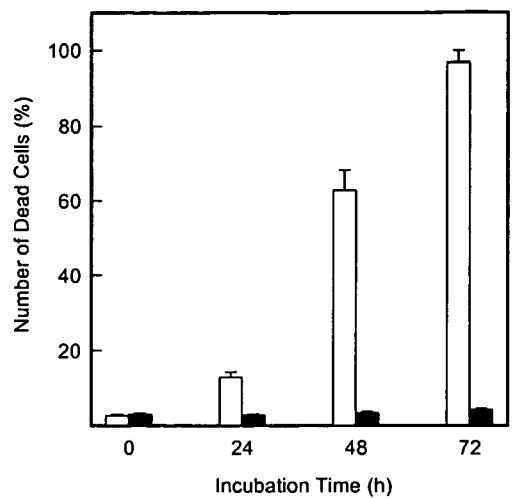

Fig. 11: Effect of adenosine kinase inhibitor, 4-amino-3-iodo-1β-D-ribofuranosylpyrazolo [3,4-d]-pyrimidine (AIRPP), on viability of HL-60 cells cultivated in presence of 2OH3MeOBAPR. Exponencially growing cells were cultivated for 72h with 20 μM 2OH3MeOBAPR (white bars) and comdination of 20 μM 2OH3MeOBAPR and 1μM AIRPP (black bars). Cell viability was measured during the incubation using combined FDA/PI staining.

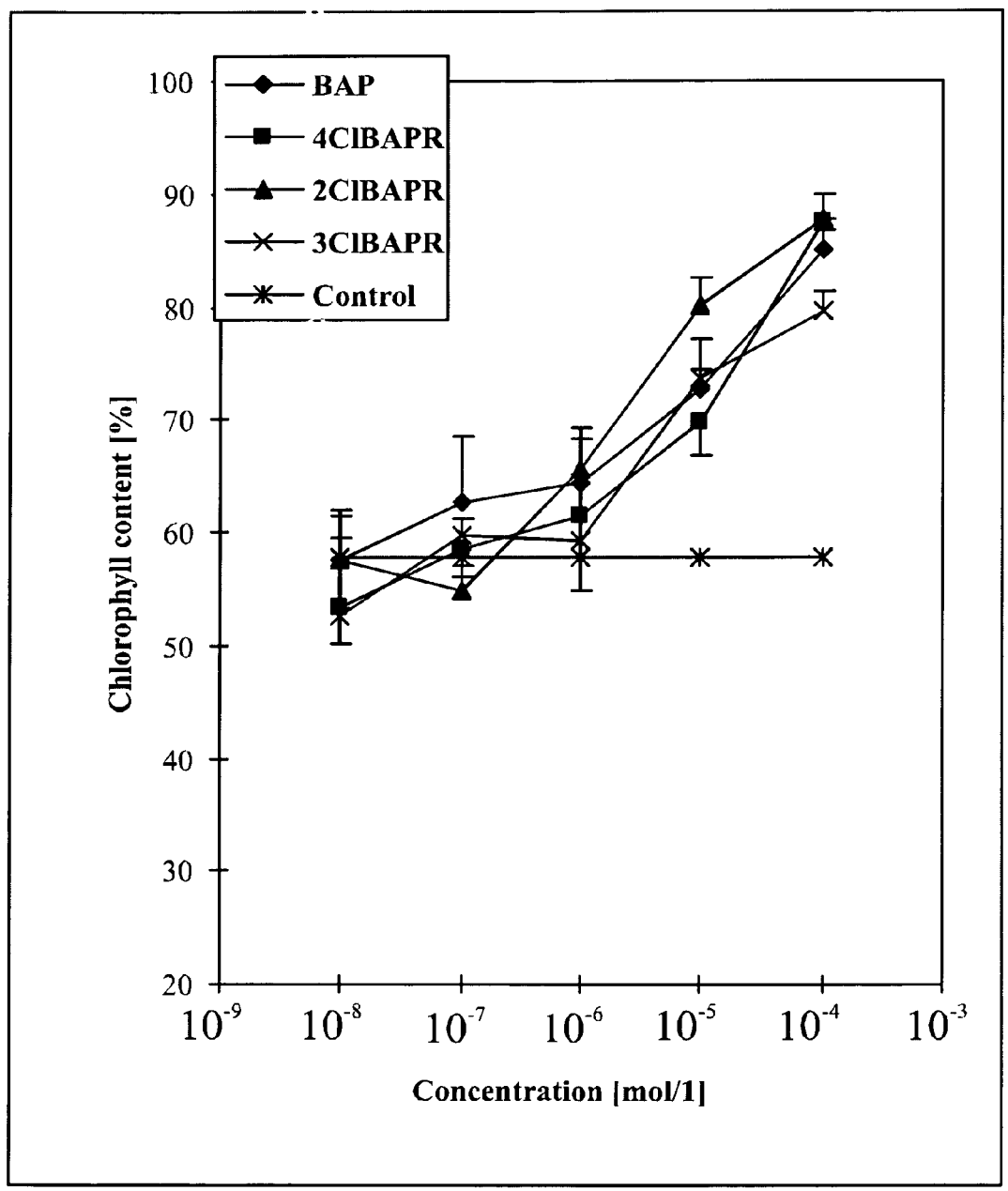
Fig. 12: Effect of tested compounds on retention of chlorophyll in excised wheat leaf tips. Values are expressed % of initial chlorophyll content of fresh leaves before the incubation. Dashed line indicates control incubation without any cytokinin, which was 57, 7 ± 0, 9.

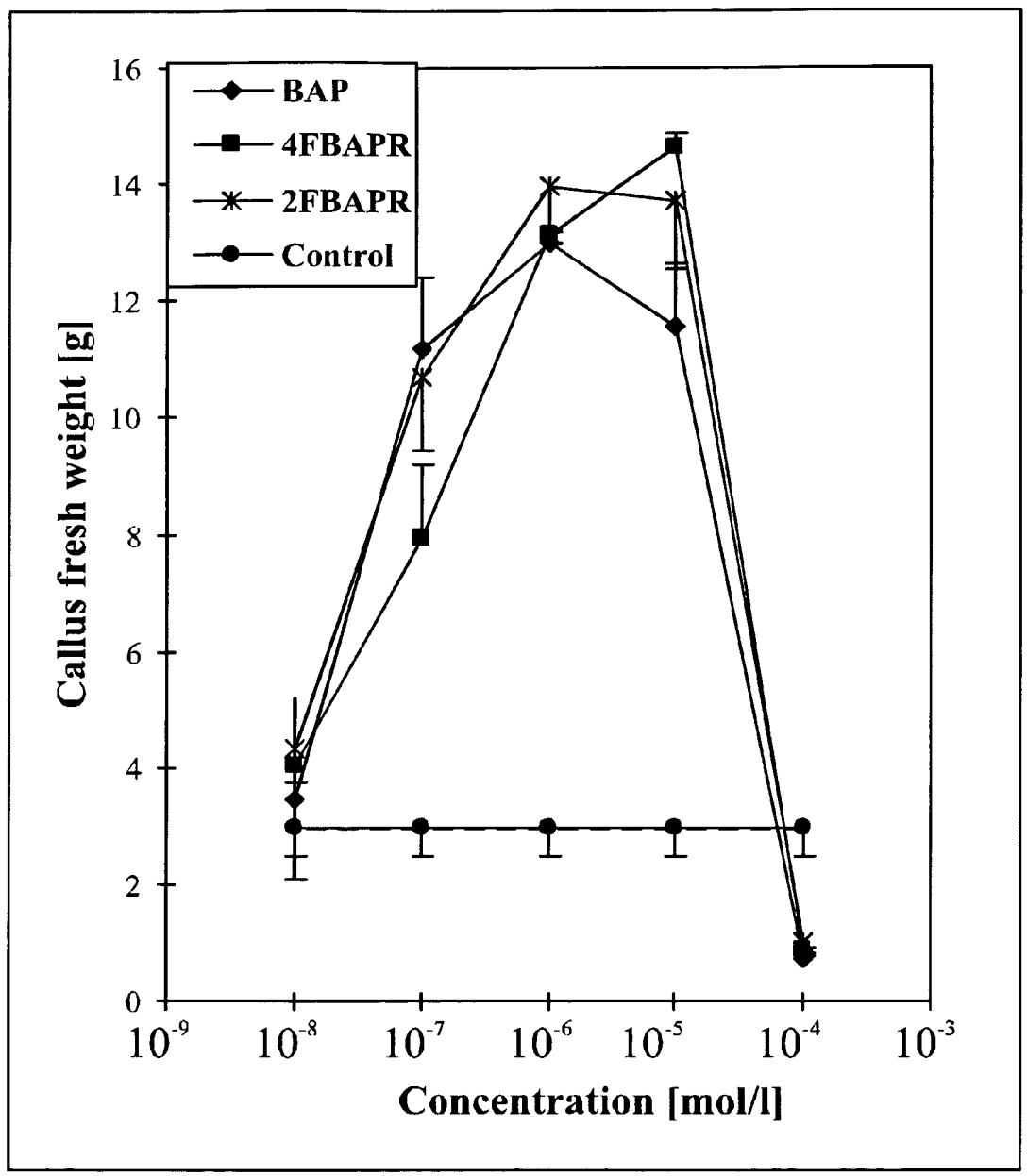
Fig. 13: Effect of tested compounds on fresh weight yield of tobacco callus culture. Error bars show standard deviation of the mean for 5 replicate determinations. Line —•— indicates the value for the control treatment without any cytokinin, 2,5 ± 0,3 g.

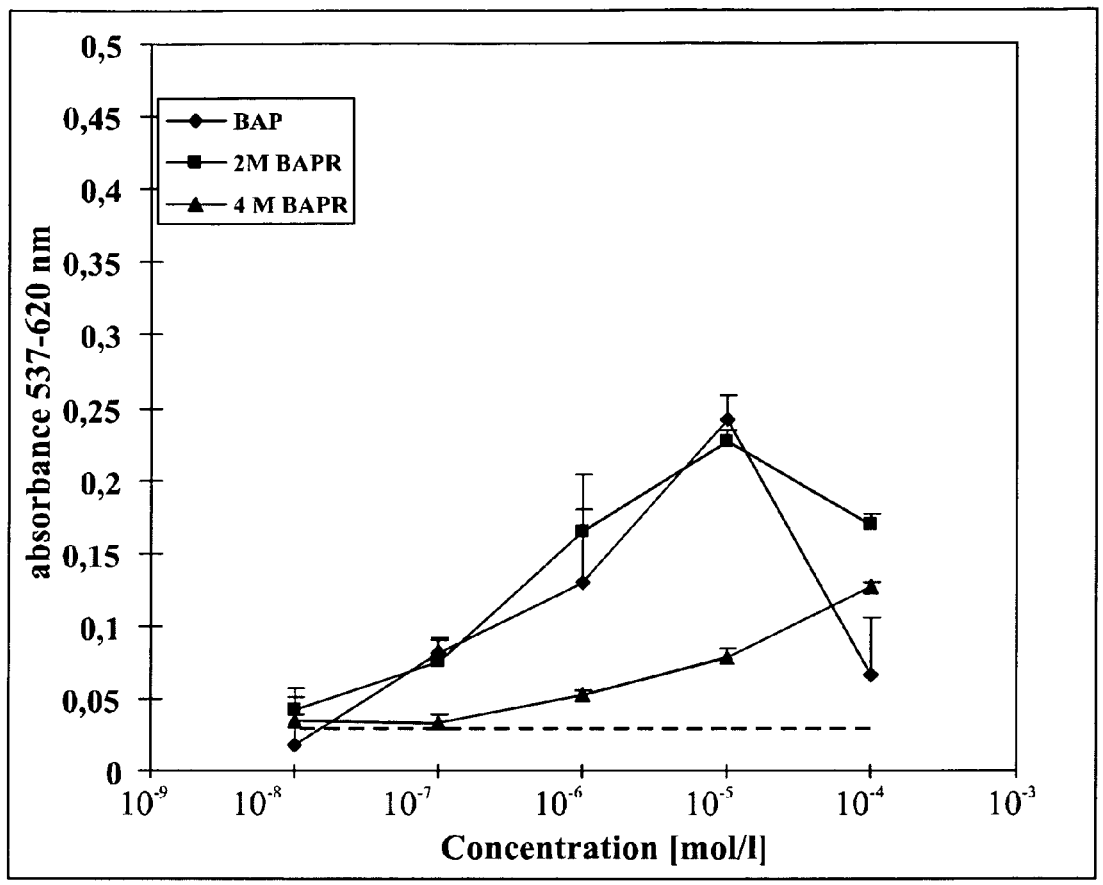
Fig. 14: Effect of tested compounds on dark induction of betacyanin synthesis in *Amarantus caudatus* cotyledons/hypocotyls explants. Values represent the difference in O.D. units between absorption at 537 and 620 nm.

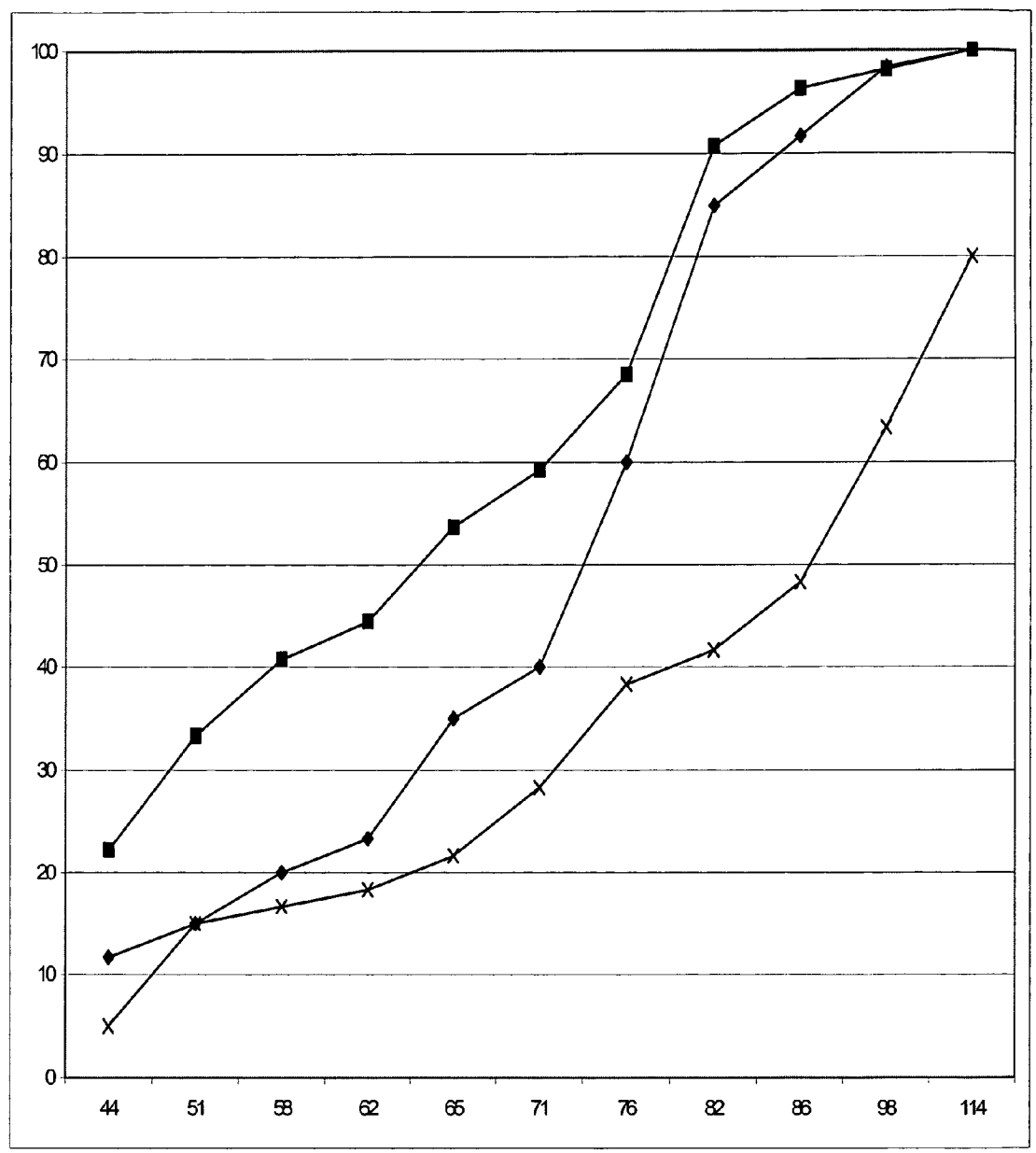
Fig. 15. Relative number of with at least one brown leaf in function of culture time
(■: BAP, ●: mT, ▲: mMeOBAPR)

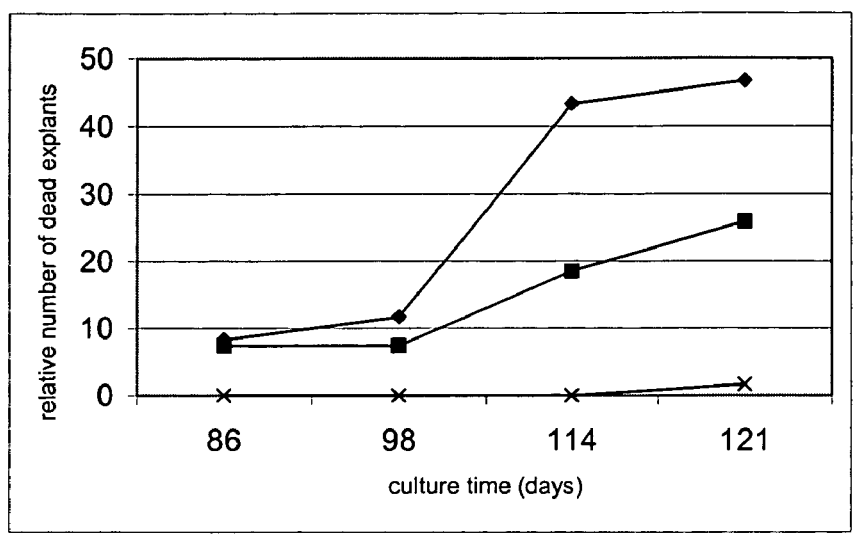
Fig. 16. Relative number of dead explants in relation to culture time (■: BA, ●: mT, ▲: mMeOBAPR)

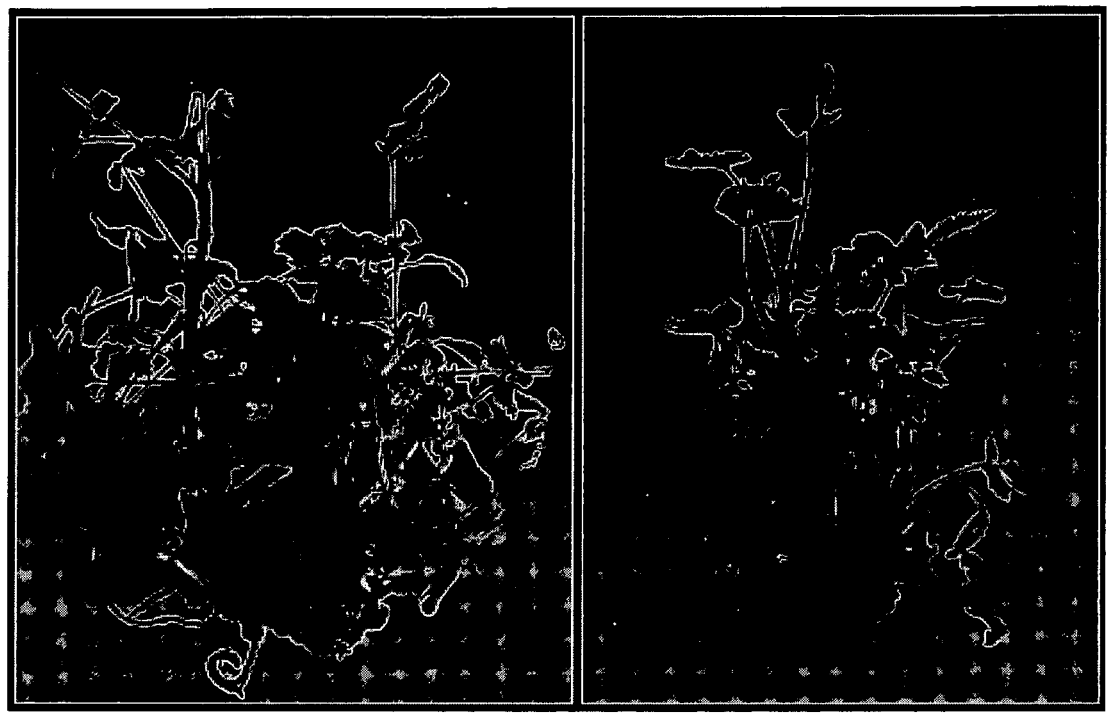
Fig. 17. Left: dead *Rosa* explant on BA containing medium; right: vigorous *Rosa* plantlet after 121 days of cultivation on mMeOBAPR containing medium

SUBSTITUTION DERIVATIVES OF N⁶-BENZYLADENOSINE, METHODS OF THEIR PREPARATION, THEIR USE FOR PREPARATION OF DRUGS, COSMETIC PREPARATIONS AND GROWTH REGULATORS, PHARMACEUTICAL PREPARATIONS, COSMETIC PREPARATIONS AND GROWTH REGULATORS CONTAINING THESE COMPOUNDS

TECHNICAL FIELD

The invention relates to new substitution derivatives of N⁶-benzyladenosine, having anticancer, mitotic, immunosuppressive and antisenescent properties for plant, animal and human cells. This invention also relates to the methods of their preparation and their use as drugs, pharmaceutical compositions, which contain these derivatives as active compound and the use of these derivatives for the preparation of drugs, in biotechnological processes, in cosmetics and in agriculture.

BACKGROUND ART

Cytokinins can be chemically characterised as N⁶-substituted derivatives of adenine. The current nomenclature based on the system suggested by Letham (Planta 181: 361-364, 1974) and Letham and Palni (Ann. Rev. Plant. Physiol. 34: 163-197, 1983) was originally suggested for zeatin (Z) and isopentenyladenine (iP). Conjugation of purine ring is labelled by number of substituent position, as shown in the overview for iP.

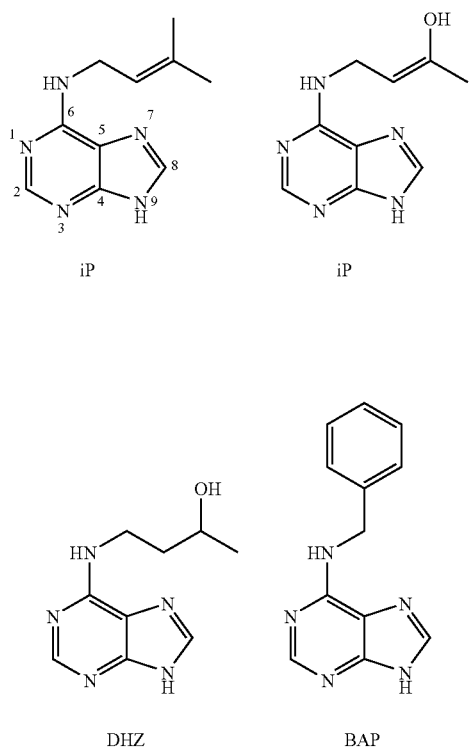

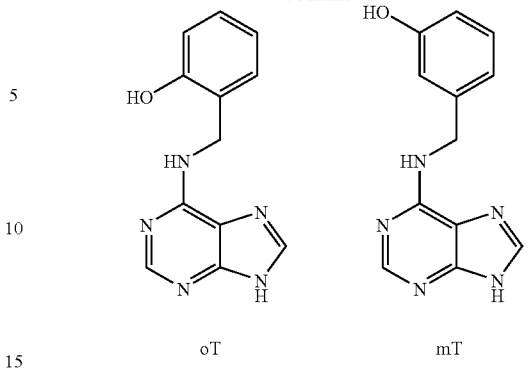

In the overview of chemical formulas of fundamental cytokinin bases have the following meaning: iP—N⁶-(Δ²-isopentenyl)adenine, Z—trans-zeatin, DHZ—dihydrozeatin, BAP—6-benzylaminopurine, oT—ortho-topolin, mT—meta-topolin.

Based on their side chain structure, cytokinins can be divided into two groups: isoprenoid and aromatic. Isoprenoid cytokinins are represented by compounds derived from the following bases: N⁶-(Δ²-isopentenyl)adenine, dihydrozeatin and zeatin. 6-benzylaminopurine, meta- and ortho-topolin and their metabolites belong to the aromatic cytokinin group.

In case of isoprenoid cytokinins, conjugation plays an important role, including modifications of purine ring and N⁶-side chain. The major cytokinin conjugates in plants are 9-ribosides, 9-ribotides, 3-, 7-, 9-a O-glukosides, O-xylosides, 9-ribosylglukosides, O-acetyl a O-allyl derivatives and also alanin conjugates (the details see in Mok, D. W. S., Mok, M. C.: Cytokinins: Chemistry, Activity and Function. CRC Press, Boca Raton, London, Tokyo 1994).

Whereas free bases represent an active cytokinin form, (Laloue and Pethe, In: Wareing, P. F. (ed.): Plant Growth Substances 1982. Pp. 185-195. Academic Press, London 1982), their ribosides are an important xylem transport forms and dominant forms in plant tissues. Riboside-5'-monophosfates are central compounds in cytokinin metabolism (Laloue et al. FEBS Let 46: 45-50, 1974; Physiol. Veg. 13: 781-796, 1975; Plant Physiol. 59: 478-483, 1977; In: Guern, J., Péaud-Lenoël, C., (eds.): Metabolism and Molecular Activities of Cytokinins. Pp. 80-96. Springer-Verlag, Berlin 1981; Mok et al., J. Plant Physiol. 130: 423-431, 1987), which are accumulated in plant cells even against high concentration gradient, because of cell membrane impermeability for these metabolites (Laloue et al., 1974, 1975, Laloue and Pethe In: Wareing, P. F. (ed.): Plant Growth Substances 1982. Pp. 185-195. Academic Press, London 1982.).

Cytokinins play an important role in many different developmental processes, including cell division, growth and differentiation, as well as flower and fruit development. They can break seed dormancy, inhibit apical dominance and stimulate the growth of side shoots, delay the cell aging, increase stress resistance, affect membrane permeability and cause accumulation of various metabolites in the site of their application (Letham a Palni 1983—Ann. Rev. Plant. Physiol. 34: 163-197, 1983, Mok, D. W. S., Mok, M. C.: Cytokinins: Chemistry, Activity and Function. CRC Press, Boca Raton, London, Tokyo 1994).

Since all living organisms on the Earth have been evolutionary developing together for many million years, the presence of regulatory interactions of plant compounds, as cytokinins are, in animals and human can be assumed. Cytokinin-derived compounds probably affect many different molecular mechanisms in animal and human cells. We have recently discovered that novel generations of anti-inflammatory, anticancer, immunosuppressive, antiviral and other drugs could be based on $N^6$-substituted purines and their derivatives.

It is an object of this invention to provide anticancer, immunosuppressive, growth-regulatory, morphogeneticaly active and antisenescence heterocyclic compounds derived from C2- and phenyl-substituted 6-benzylaminopurine ribosides having improved selectivity and efficiency index, i.e. which are less toxic yet more efficacious than analogues known heretofore.

DISCLOSURE OF INVENTION

Object of this invention are substitution derivatives of $N^6$-benzyladenosine of the general formula I

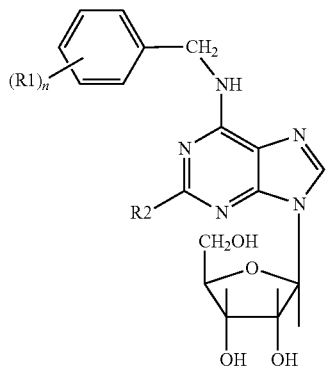

and their pharmaceutically acceptable salts with alkali metals, ammonium or amines, wherein R2 is hydrogen atom, hydroxyl, halogen, alkoxy, amino, hydrazo, mercapto, methylmercapto, carboxyl, cyano, nitro, amido, sulpho, sulphamido, acylamino, acyloxy, alkylamino, dialkylamino, alkylmercapto, carbylalkoxy, cycloalkyl or carbamoyl group, and $(R1)_n$, wherein n is 2-6 carbon atoms of the phenyl ring optionally substituted with one to five substituents selected from the group R1 wherein R1 is hydrogen, hydroxyl, halogen, alkoxy, amino, hydrazo, mercapto, methylmercapto, carboxyl, cyano, nitro, amido, sulpho, sulphamido, acylamino, acyloxy, alkylamino, dialkylamino, alkylmercapto, carbylalkoxy, cycloalkyl or carbamoyl alkyl, substituted alkyl, cycloalkyl, substituted cycloalkyl, cycloalkylalkyl, arylalkyl, heteroalkyl, heteroarylalkyl, cycloheteroalkyl alkyl or R1'-X, wherein X is NH—, —N($C_1$-$C_6$-alkyl)-, —O— or —S— and R1' is hydrogen, alkyl, substituted alkyl, acyl, amido, sulpho, cycloalkyl, substituted cycloalkyl, aryl, substituted aryl, heterocycle, heteroaryl, substituted heteroaryl, arylalkyl, cycloheteroalkyl, substituted cycloheteroalkyl, heteroarylalkyl, heteroalkyl, cycloalkyl alkyl and cycloheteroalkyl alkyl;

wherein the generic substituent groups have meanings as defined in this legend, wherein halogen refers to
  halogen atom selected from the group containing fluorine atom, bromine atom, chlorine atom and iodine atom, alkyl refers to
  branched or unbranched alkyl chain containing 1 to 6 carbon atoms,
  branched or unbranched alkenyl chain containing 2 to 6 carbon atoms,
  branched or unbranched alkynyl chain containing 2 to 6 carbon atoms, substituted alkyl refers to
  branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, carbyloxy refers to
  group —$OR_a$, wherein $R_a$ is alkyl, substituted alkyl, aryl, substituted aryl, arylalkyl, substituted arylalkyl, cycloalkyl, substituted cycloalkyl, cycloheteroalkyl or substituted cycloheteroalkyl, wherein mentioned generic substituent groups have meanings as defined in this legend, carbylmercapto refers to
  group —$SR_b$, wherein $R_b$ is alkyl, substituted alkyl, aryl, substituted aryl, arylalkyl, substituted arylalkyl, cycloalkyl, substituted cycloalkyl, cycloheteroalkyl or substituted cycloheteroalkyl, wherein mentioned generic substituent groups have meanings as defined in this legend, sulpho refers to —$SO_3R_c$, wherein $R_c$ is
  hydrogen atom H,
  branched or unbranched alkyl chain containing 1 to 6 carbon atoms,
  branched or unbranched alkenyl chain containing 2 to 6 carbon atoms,
  branched or unbranched alkynyl chain containing 2 to 6 carbon atoms,
  branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, sulphamido refers to —$NHSO_3R_d$, wherein $R_d$ is
  hydrogen atom H,
  branched or unbranched alkyl chain containing 1 to 6 carbon atoms,
  branched or unbranched alkenyl chain containing 2 to 6 carbon atoms,
  branched or unbranched alkynyl chain containing 2 to 6 carbon atoms,
  branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, acyl refers to
- group —C(O)$R_e$, wherein $R_e$ is hydrogen atom, alkyl, substituted alkyl, aryl, substituted aryl, arylalkyl, substituted arylalkyl, cycloalkyl, substituted cycloalkyl, wherein mentioned generic substituent groups have meanings as defined in this legend, aryloxy refers to
- group —OAr, wherein Ar is aryl, substituted aryl, heteroaryl or substituted heteroaryl, wherein mentioned generic substituent groups have meanings as defined in this legend, alkylamino refers to
- group $NR_f R'_g$, wherein $R_f$ and $R'_g$ are independently one of another hydrogen atom, alkyl, substituted alkyl, aryl, substituted aryl, heteroaryl or substituted heteroaryl, wherein mentioned generic substituent groups have meanings as defined in this legend, amido refers to
- group —C(O)$NR_h R'_i$, wherein $R_h$ and $R'_i$ are independently one of another hydrogen atom, alkyl, substituted alkyl, aryl, substituted aryl, heteroaryl or substituted heteroaryl, wherein mentioned generic substituent groups have meanings as defined in this legend, carboxyl refers to
- group —C(O)$OR_j$, wherein $R_j$ is hydrogen atom, alkyl, substituted alkyl, aryl, substituted aryl, heteroaryl or substituted heteroaryl, wherein mentioned generic substituent groups have meanings as defined in this legend, carbamino refers to
- group —NHCO$R_k$, wherein $R_k$ is hydrogen atom, alkyl, substituted alkyl, aryl, substituted aryl, heteroaryl or substituted heteroaryl, wherein mentioned generic substituent groups have meanings as defined in this legend, aryl refers to
- aromatic carbocyclic group containing 6 to 18 carbon atoms, which is formed by at least one aromatic ring (e.g. phenyl or biphenyl) or multiple condensed rings, from which at least one ring is aromatic (e.g. 1,2,3,4-tetrahydronaphtyl, naphtyl, anthryl or phenanthryl), substituted aryl refers to
- aromatic carbocyclic group containing 6 to 18 carbon atoms, which is formed by at least one aromatic ring (e.g. phenyl or biphenyl) or multiple condensed rings, from which at least one ring is aromatic (e.g. 1,2,3,4-tetrahydronaphtyl, naphtyl, anthryl or phenanthryl), which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, heterocycle refers to
- heterocyclic group containing 4 to 9 carbon atoms and at least one heteroatom selected from the group containing oxygen atom, sulphur atom and nitrogen atom, heteroaryl refers to
- heterocyclic group containing 4 to 9 carbon atoms and at least one heteroatom selected from the group containing oxygen atom, sulphur atom and nitrogen atom, wherein at least one ring is aromatic, substituted heteroaryl refers to
- heterocyclic group containing 4 to 9 carbon atoms and at least one heteroatom selected from the group containing oxygen atom, sulphur atom and nitrogen atom, wherein at least one ring is aromatic, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, arylalkyl refers to
- group —R1-Ar, wherein Ar refers to aryl group and $R_1$ is
- branched or unbranched alkyl chain containing 1 to 6 carbon atoms,
- branched or unbranched alkenyl chain containing 2 to 6 carbon atoms,
- branched or unbranched alkynyl chain containing 2 to 6 carbon atoms,
- aromatic carbocyclic group containing 6 to 18 carbon atoms, which is formed by at least one aromatic ring (e.g. phenyl or biphenyl) or multiple condensed rings, from which at least one ring is aromatic (e.g. 1,2,3,4-tetrahydronaphtyl, naphtyl, anthryl or phenanthryl), which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, heteroalkyl refers to
- group —$R_m$-L, wherein $R_m$ is
- branched or unbranched alkyl chain containing 1 to 6 carbon atoms,
- branched or unbranched alkenyl chain containing 2 to 6 carbon atoms,
- branched or unbranched alkynyl chain containing 2 to 6 carbon atoms,
- branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, and L is
- heterocyclic group containing 4 to 9 carbon atoms and at least one heteroatom selected from the group containing oxygen atom, sulphur atom and nitrogen atom, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, heteroarylalkyl refers to
- group —$R_n$-G, wherein $R_n$ is
- branched or unbranched alkyl chain containing 1 to 6 carbon atoms,
- branched or unbranched alkenyl chain containing 2 to 6 carbon atoms,
- branched or unbranched alkynyl chain containing 2 to 6 carbon atoms,
- branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, and G is
heterocyclic group containing 4 to 9 carbon atoms and at least one heteroatom selected from the group containing oxygen atom, sulphur atom and nitrogen atom, wherein at least one ring is aromatic, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, cycloalkyl refers to
monocyclic or polycyclic alkyl group containing 3 to 15 carbon atoms, substituted cycloalkyl refers to
monocyclic or polycyclic alkyl group containing 3 to 15 carbon atoms, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, heterocycloalkyl refers to
monocyclic or polycyclic alkyl group containing 3 to 15 carbon atoms, in whose cyclic structure is at least one carbon atom replaced by heteroatom from the group containing oxygen atom, sulphur atom, nitrogen atom and phosphorus atom, substituted cycloheteroalkyl refers to
monocyclic or polycyclic alkyl group containing 3 to 15 carbon atoms, in whose cyclic structure is at least one carbon atom replaced by heteroatom from the group containing oxygen atom, sulphur atom, nitrogen atom and phosphorus atom, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, cycloalkylalkyl refers to
group —$R_o$-J, wherein $R_o$ is
branched or unbranched alkyl chain containing 1 to 6 carbon atoms,
branched or unbranched alkenyl chain containing 2 to 6 carbon atoms,
branched or unbranched alkynyl chain containing 2 to 6 carbon atoms,
branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, and J is
monocyclic or polycyclic alkyl group containing 3 to 15 carbon atoms, or
monocyclic or polycyclic alkyl group containing 3 to 15 carbon atoms, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, and heterocycloalkylalkyl refers to
group —$R_p$V, wherein $R_p$ is
branched or unbranched alkyl chain containing 1 to 6 carbon atoms,
branched or unbranched alkenyl chain containing 2 to 6 carbon atoms,
branched or unbranched alkynyl chain containing 2 to 6 carbon atoms,
branched or unbranched alkyl, alkenyl and alkynyl chain containing 1 to 6 carbon atoms which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, and V is
monocyclic or polycyclic alkyl group containing 3 to 15 carbon atoms, in whose cyclic structure is at least one carbon atom replaced by heteroatom from the group containing oxygen atom, sulphur atom, nitrogen atom and phosphorus atom,
monocyclic or polycyclic alkyl group containing 3 to 15 carbon atoms, in whose cyclic structure is at least one carbon atom replaced by heteroatom from the group containing oxygen atom, sulphur atom, nitrogen atom and phosphorus atom, which is optionally substituted with one to five substituents selected from the group containing hydroxyl, alkoxy, amino, hydrazo, mercapto, carboxyl, cyano, nitro, amido, sulpho, sulphamido, acylamino, acyloxy, alkylamino, dialkylamino, alkylmercapto, carbylalkoxy, cycloalkyl and carbamoyl group, wherein mentioned generic substituent groups have meanings as defined in this legend, in the form of racemates or optically active isomers, as well as their addition salts with acids.

The following heterocyclic derivatives are particularly preferred, namely: 6-(2-fluorobenzylamino)purine riboside, 6-(3-fluorobenzylamino)purine riboside, 6-(4-fluorobenzylamino)purine riboside, 6-(2-bromobenzylamino)purine riboside, 6-(3-bromobenzylamino)purine riboside, 6-(4-bromobenzylamino)purine riboside, 6-(2-iodobenzylamino)purine riboside, 6-(3-iodobenzylamino)purine riboside, 6-(4-iodobenzylamino)purine riboside, 6-(2-chlorobenzylamino) purine riboside, 6-(2-chlorobenzylamino)purine riboside, 6-(3-chlorobenzylamino)purine riboside, 6-(4-chlorobenzylamino)purine riboside, 6-(2-acetylbenzylamino)purine riboside, 6-(3-acetylbenzylamino)purine riboside, 6-(4-acetylbenzylamino)purine riboside, 6-(3-carboxybenzylamino) purine riboside, 6-(4-carboxybenzylamino)purine riboside, 6-(2-acetoxybenzylamino)purine riboside, 6-(3-acetoxybenzylamino)purine riboside, 6-(4-acetoxybenzylamino)purine riboside, 6-(2-nitrobenzylamino)purine riboside, 6-(3-nitrobenzylamino)purine riboside, 6-(4-nitrobenzylamino)purine riboside, 6-(2-sulphobenzylamino)purine riboside, 6-(3-sulphobenzylamino)purine riboside, 6-(4-sulphobenzylamino)purine riboside, 6-(2-cyanobenzylamino)purine riboside, 6-(3-cyanobenzylamino)purine riboside, 6-(4-cyanobenzylamino)purine riboside, 6-(5-nitro-2-methylbenzylamino)purine riboside, 6-(2-methylbenzylamino)purine riboside, 6-(3-methylbenzylamino)purine riboside, 6-(4-methylbenzylamino)purine riboside, 6-(4-methylaminobenzylamino)purine riboside, 6-(2-methoxybenzylamino)purine riboside, 6-(3-methoxybenzylamino)purine riboside, 6-(4-methoxybenzylamino)purine riboside, 6-(2-hydroxybenzylamino)purine riboside, 6-(3-hydroxybenzylamino)purine riboside, 6-(4-hydroxybenzylamino)purine riboside, 6-(4-hexylbenzylamino)purine riboside, 6-(4-hexyloxybenzylamino)purine riboside, 6-(2-formylbenzylamino)purine riboside, 6-(3-formylbenzylamino)purine riboside, 6-(4-formylbenzylamino)purine riboside, 6-(2-ethoxybenzylamino)purine riboside, 6-(3-ethoxybenzylamino)purine riboside, 6-(4-ethoxybenzylamino)purine riboside, 6-(4-ethylbenzylamino)purine riboside, 6-(4-pentylbenzylamino)purine riboside, 6-(4-pentyloxybenzylamino)purine riboside, 6-(4-phenoxybenzylamino)purine riboside, 6-(4-phenylbenzylamino)purine riboside, 6-(4-propylbenzylamino)purine riboside, 6-(4-propyloxybenzylamino)purine riboside, 6-(4-oktylbenzylamino)purine riboside, 6-(4-octyloxybenzylamino)purine riboside, 6-(4-ethyloxybenzylamino)purine riboside, 6-(3,4-diacetoxybenzylamino)purine riboside, 6-(3,5-diacetoxybenzylamino)purine riboside, 6-(2,5-diaminobenzylamino)purine riboside, 6-(3,5-dibromobenzylamino)purine riboside, 6-(3,5-dibromo-4-methoxybenzylamino)purine riboside, 6-(2,3-dichlorobenzylamino)purine riboside, 6-(2,4-dichlorobenzylamino)purine riboside, 6-(2,5-dichlorobenzylamino)purine riboside, 6-(2,6-dichlorobenzylamino)purine riboside, 6-(3,4-dichlorobenzylamino)purine riboside, 6-(3,5-dichlorobenzylamino)purine riboside, 6-(2,3,4,5-tetrafluorobenzylamino)purine riboside, 6-(2-chloro-3,6-difluorobenzylamino)purine riboside, 6-(5-chloro-2-fluorobenzylamino)purine riboside, 6-(2,3,4-trifluorobenzylamino)purine riboside, 6-(2,3,5-trifluorobenzylamino)purine riboside, 6-(2,4,5-trifluorobenzylamino)purine riboside, 6-(3,4,5-trifluorobenzylamino)purine riboside, 6-(2,3,6-trifluorobenzylamino)purine riboside, 6-(3-chloro-2,6-difluorobenzylamino)purine riboside, 6-(2-chloro-6-fluorobenzylamino)purine riboside, 6-(2,6-difluorobenzylamino)purine riboside, 6-(2,4-difluorobenzylamino)purine riboside, 6-(3,4-difluorobenzylamino)purine riboside, 6-(2,5-difluorobenzylamino)purine riboside, 6-(3,5-difluorobenzylamino)purine riboside, 6-(5-fluoro-2-(trifluoromethyl)benzylamino)purine riboside, 6-(4-fluoro-2-(trifluoromethyl)benzylamino)purine riboside, 6-(2-chloro-5-(trifluoromethyl)benzylamino)purine riboside, 6-(2-(difluoromethoxy)benzylamino)purine riboside, 6-(4-(difluoromethoxy)benzylamino)purine riboside, 6-(2-fluoro-5-(trifluoromethyl)benzylamino)purine riboside, 6-(3-fluoro-4-(trifluoromethyl)benzylamino)purine riboside, 6-(2-fluoro-4-(trifluoromethyl)benzylamino)purine riboside, 6-(2-(trifluoromethylthio)benzylamino)purine riboside, 6-(2-fluoro-3-(trifluoromethyl)benzylamino)purine riboside, 6-(2-chloro-6-fluoro-3-methylbenzylamino)purine riboside, 6-(6-chloro-2-fluoro-3-methylbenzylamino)purine riboside, 6-(3-chloro-2-fluoro-5-(trifluoromethyl)benzylamino)purine riboside, 6-(3-chloro-2-fluoro-6-(trifluoromethyl)benzylamino)purine riboside, 6-(2,3-difluoro-4-methylbenzylamino)purine riboside, 6-(2,6-difluoro-3-methylbenzylamino)purine riboside, 6-(2-fluoro-6-(trifluoromethyl)benzylamino)purine riboside, 6-(3-chloro-2,6-difluorobenzylamino)purine riboside, 6-(3-(trifluoromethylthio)benzylamino)purine riboside, 6-(3-fluoro-4-methyl benzylamino)purine riboside, 6-(4-fluoro-3-methylbenzylamino)purine riboside, 6-(5-fluoro-2-methylbenzylamino)purine riboside, 6-(2-chloro-3,6-difluorobenzylamino)purine riboside, 6-(4-(trifluoromethylthio)benzylamino)purine riboside, 6-(3-fluoro-5-(trifluoromethyl)benzylamino)purine riboside, 6-(2-chloro-4-fluorobenzylamino)purine riboside, 6-(2-(trifluoromethoxy)benzylamino)purine riboside, 6-(3-(trifluoromethyl)benzylamino)purine riboside, 6-(2-(trifluoromethyl)benzylamino)purine riboside, 6-(4-(trifluoromethyl)benzylamino)purine riboside, 6-(4-chloro-3-(trifluoromethyl)benzylamino)purine riboside, 6-(4-fluoro-3-(trifluoromethyl)benzylamino)purine riboside, 6-(3,5-bis(trifluoromethyl)benzylamino)purine riboside, 6-(3-(trifluoromethoxy)benzylamino)purine riboside, 6-(4-(trifluoromethoxy)benzylamino)purine riboside, 6-(4-(trifluoromethyl)benzylamino)purine riboside, 6-(4-diethylaminobenzylamino)purine riboside, 6-(3,4-dihydroxybenzylamino)purine riboside, 6-(3,5-dihydroxybenzylamino)purine riboside, 6-(3,4-dihydroxybenzylamino)purine riboside, 6-(2,3-ethylenedioxybenzylamino)purine riboside, 6-(2,4-dihydroxybenzylamino)purine, 6-(2,5-dihydroxybenzylamino)purine riboside, 6-(2,6-dihydroxybenzylamino)purine riboside, 6-(3,4-dimethoxybenzylamino)purine riboside, 6-(3,4-dimethoxybenzylamino)purine riboside, 6-(3,5-dimethoxybenzylamino)purine riboside, 6-(2,3-dimethoxybenzylamino)purine riboside, 6-(2,4-dimethoxybenzylamino)purine riboside, 6-(2,5-dimethoxybenzylamino)purine riboside, 6-(2,6-dimethoxybenzylamino)purine riboside, 6-(2-hydroxy-3-methoxybenzylamino)purine riboside, 6-(2-hydroxy-4-methoxybenzylamino)purine riboside, 6-(2-hydroxy-5-methoxybenzylamino)purine riboside, 6-(2-hydroxy-6-methoxybenzylamino)purine riboside, 6-(3-hydroxy-2-methoxybenzylamino)purine riboside, 6-(3-hydroxy-4-methoxybenzylamino)purine riboside, 6-(3-hydroxy-5-methoxybenzylamino)purine riboside, 6-(3-hydroxy-6-methoxybenzylamino)purine riboside, 6-(4-hydroxy-2-methoxybenzylamino)purine riboside, 6-(4-hydroxy-3-methoxybenzylamino)purine riboside, 6-(4-hydroxy-5-methoxybenzylamino)purine riboside, 6-(4-hydroxy-6-methoxybenzylamino)purine riboside, 6-(2-hydroxy-3,4-dimethoxybenzylamino)purine riboside, 6-(2-hydroxy-3,5-dimethoxybenzylamino)purine riboside, 6-(2-hydroxy-3,6-dimethoxybenzylamino)purine riboside, 6-(2-hydroxy-4,5-dimethoxybenzylamino)purine riboside, 6-(2-hydroxy-4,6-dimethoxybenzylamino)purine riboside, 6-(2-hydroxy-5,6-dimethoxybenzylamino)purine riboside, 6-(3-hydroxy-4,5-dimethoxybenzylamino)purine riboside, 6-(3-hydroxy-4,6-dimethoxybenzylamino)purine riboside, 6-(3-hydroxy-2,4-dimethoxybenzylamino)purine riboside, 6-(3-hydroxy-2,5- dimethoxybenzylamino)purine riboside, 6-(3-hydroxy-2,6-dimethoxybenzylamino)purine riboside, 6-(4-hydroxy-2,3-dimethoxybenzylamino)purine riboside, 6-(4-hydroxy-2,5-dimethoxybenzylamino)purine riboside, 6-(4-hydroxy-2,6-dimethoxybenzylamino)purine riboside, 6-(4-hydroxy-3,5-dimethoxybenzylamino)purine riboside, 6-(4-hydroxy-3,6-dimethoxybenzylamino)purine riboside, 6-(2,3-dihydroxy-4-methoxybenzylamino)purine riboside, 6-(2,3-dihydroxy-5-methoxybenzylamino)purine riboside, 6-(2,3-dihydroxy-6-methoxybenzylamino)purine riboside, 6-(2,4-dihydroxy-3-methoxybenzylamino)purine riboside, 6-(2,4-dihydroxy-5-methoxybenzylamino)purine riboside, 6-(2,4-dihydroxy-6-methoxybenzylamino)purine riboside, 6-(2,5-dihydroxy-3-methoxybenzylamino)purine riboside, 6-(2,5-dihydroxy-4-methoxybenzylamino)purine riboside, 6-(2,5-dihydroxy-6-methoxybenzylamino)purine riboside, 6-(2,6-dihydroxy-3-methoxybenzylamino)purine riboside, 6-(2,6-dihydroxy-4-methoxybenzylamino)purine riboside, 6-(2,6-dihydroxy-5-methoxybenzylamino)purine riboside, 6-(3,4-dihydroxy-2-methoxybenzylamino)purine riboside, 6-(3,4-dihydroxy-5-methoxybenzylamino)purine riboside, 6-(3,4-dihydroxy-6-methoxybenzylamino)purine riboside, 6-(3,5-dihydroxy-2-methoxybenzylamino)purine riboside, 6-(3,5-dihydroxy-4-methoxybenzylamino)purine riboside, 6-(3,5-dihydroxy-6-methoxybenzylamino)purine riboside, 6-(2,3,4-trimethoxybenzylamino)purine riboside, 6-(2,4,5-trimethoxybenzylamino)purine riboside, 6-(2,4,6-trimethoxybenzylamino)purine riboside, 6-(3,4,5-trimethoxybenzylamino)purine riboside, 6-(2-hydroxy-3,4,5-trimethoxybenzylamino)purine riboside, 6-(2-hydroxy-3,4,6-trimethoxybenzylamino)purine riboside, 6-(2-hydroxy-4,5,6-trimethoxybenzylamino)purine riboside, 6-(2,4,6-trimethoxybenzylamino)purine riboside, 6-(2,3,4-trihydroxybenzylamino)purine riboside, 6-(2,4,6-trihydroxybenzylamino)purine riboside, 6-(2,3,4-trihydroxybenzylamino)purine riboside, 6-(3,4,5-trihydroxybenzylamino)purine riboside, 6-(2,4,6-trihydroxybenzylamino)purine riboside, 6-(2-hydroxy-3-chlorobenzylamino)purine riboside, 6-(2-hydroxy-4-chlorobenzylamino)purine riboside, 6-(2-hydroxy-5-chlorobenzylamino)purine riboside, 6-(2-hydroxy-6-chlorobenzylamino)purine riboside, 6-(2-hydroxy-3-iodobenzylamino)purine riboside, 6-(2-hydroxy-4-iodobenzylamino)purine riboside, 6-(2-hydroxy-5-iodobenzylamino)purine riboside, 6-(2-hydroxy-6-iodobenzylamino)purine riboside, 6-(2-hydroxy-3-bromobenzylamino)purine riboside, 6-(2-hydroxy-4-bromobenzylamino)purine riboside, 6-(2-hydroxy-5-bromobenzylamino)purine riboside, 6-(2-hydroxy-6-bromobenzylamino)purine riboside, 6-(2-hydroxy-3-fluorobenzylamino)purine riboside, 6-(2-hydroxy-4-fluorobenzylamino)purine riboside, 6-(2-hydroxy-5-fluorobenzylamino)purine riboside, 6-(2-hydroxy-6-fluorobenzylamino)purine riboside, 6-(2-hydroxy-3-methylbenzylamino)purine riboside, 6-(2-hydroxy-4-methylbenzylamino)purine riboside, 6-(2-hydroxy-5-methylbenzylamino)purine riboside, 6-(2-hydroxy-6-methylbenzylamino)purine riboside, 6-(2,3-dihydroxy-4-chlorobenzylamino)purine riboside, 6-(2,3-dihydroxy-5-chlorobenzylamino)purine riboside, 6-(2,5-dihydroxy-4-chlorobenzylamino)purine riboside, 6-(2,6-dihydroxy-4-chlorobenzylamino)purine riboside, 6-(2,6-dihydroxy-4-bromoxybenzylamino)purine riboside, 6-(2,6-dihydroxy-4-iodobenzylamino)purine riboside, 6-(2,6-dihydroxy-3-chlorobenzylamino)purine riboside, 6-(2,6-dihydroxy-3-bromobenzylamino)purine riboside, 6-(2,6-dihydroxy-3-iodobenzylamino)purine riboside, 6-(2,6-dihydroxy-3-fluorobenzylamino)purine riboside, 6-(2,6-dihydroxy-3,5-dichlorobenzylamino)purine riboside, 6-(2,6-dihydroxy-3,5-dibromobenzylamino)purine riboside, 6-(2,6-dihydroxy-3,5-diiodobenzylamino)purine riboside, 6-(2,6-dihydroxy-3,5-difluorobenzylamino)purine riboside, 6-(4,5-dimethoxy-2-nitrobenzylamino)purine riboside, 6-(3,4-dimethylbenzylamino)purine riboside, 6-(2,3-dimethylbenzylamino)purine riboside, 6-(2,4-dimethylbenzylamino)purine riboside, 6-(2,6-dimethylbenzylamino)purine riboside, 6-(2,6-dimethyl-4-hydroxybenzylamino)purine riboside, 6-(3,5-dimethyl-4-hydroxybenzylamino)purine riboside, 6-(2-fluoro-4-hydroxybenzylamino)purine riboside, 6-(3-fluoro-4-methylbenzylamino)purine riboside, 6-(3,4-dinitrobenzylamino)purine riboside, 6-(3,5-dinitrobenzylamino)purine riboside, 6-(2-methyl-5-nitrobenzylamino)purine riboside, 6-(3-methyl-4-nitrobenzylamino)purine riboside, 6-(3,4-diiodo-hydroxybenzylamino)purine riboside, 6-(2-chloro-3,4-dimethoxybenzylamino)purine riboside, 6-(4-chloro-3,5-dinitrobenzylamino)purine riboside, 6-(2-chloro-4-fluorobenzylamino)purine riboside, 6-(3-chloro-4-fluorobenzylamino)purine riboside, 6-(2-chloro-6-methylbenzylamino)purine riboside, 6-(3-chloro-2-methylbenzylamino)purine riboside, 6-(3-chloro-4-methylbenzylamino)purine riboside, 6-(5-chloro-2-methoxybenzylamino)purine riboside, 6-(2-chloro-4-fluorobenzylamino)purine riboside, 6-(4-chloromethylbenzylamino)purine riboside, 6-(2-chloro-5-nitrobenzylamino)purine riboside, 6-(2-chloro-6-nitrobenzylamino)purine riboside, 6-(4-chloro-3-nitrobenzylamino)purine riboside, 6-(5-chloro-2-nitrobenzylamino)purine riboside, 6-(3-bromo-4-hydroxybenzylamino)purine riboside, 6-(3,5-dibromo-4-hydroxybenzylamino)purine, 6-(3-bromo-4-methoxybenzylamino)purine, 6-(4-bromomethylbenzylamino)purine riboside, 6-(4-butoxybenzylamino)purine riboside, 6-(4-butoxybenzylamino)purine riboside, 6-(4-/t-butyl)benzylamino)purine riboside, 6-(4-t-butyl-2,6-dimethylbenzylamino)purine riboside, 6-(2-aminobenzylamino)purine riboside, 6-(3-aminobenzylamino)purine riboside, 6-(4-aminobenzylamino)purine riboside, 6-(2-amino-3-chlorobenzylamino)purine riboside, 6-(2-amino-4-chlorobenzylamino)purine riboside, 6-(2-amino-5-chlorobenzylamino)purine riboside, 6-(2-amino-6-chlorobenzylamino)purine riboside, 6-(3-amino-2-chlorobenzylamino)purine riboside, 6-(3-amino-4-chlorobenzylamino)purine riboside, 6-(3-amino-5-chlorobenzylamino)purine riboside, 6-(3-amino-6-chlorobenzylamino)purine riboside, 6-(2,6-diamino-3-chlorobenzylamino)purine riboside, 6-(2,6-diamino-4-chlorobenzylamino)purine riboside, 6-(4-amino-3-chlorobenzylamino)purine riboside, 6-(4-amino-5-dichlorobenzylamino)purine riboside, 6-(5-amino-2-methylbenzylamino)purine riboside, 6-(2-amino-3-nitrobenzylamino)purine riboside, 6-(4-amino-3-nitrobenzylamino)purine riboside, 6-(4-benzyloxybenzylamino)purine riboside, 6-(3-acetylbenzylamino)purine riboside, 6-(2-acetylbenzylamino)purine riboside, 6-(2,4,5-trichlorobenzylamino)purine riboside, 6-(2,4,5-trichlorobenzylamino)purine riboside, 6-(2,4,6-trichlorobenzylamino)purine riboside, 6-(2,3,4-trichlorobenzylamino)purine riboside, 6-(2,3,5-trichlorobenzylamino)purine riboside, 6-(2,3,6- trichlorobenzylamino)purine riboside, 6-(2,5,6-trichlorobenzylamino)purine riboside, 2-(amino, hydroxy, chloro, fluoro, bromo, methyl or methylmercapto)-6-(2-fluorobenzylamino)purine riboside, 2-(amino, hydroxy, chloro, fluoro, bromo, methyl or methylmercapto)-6-(3-fluorobenzylamino)purine riboside, 2-(amino, hydroxy, chloro, fluoro, bromo, methyl or methylmercapto)-6-(4-fluorobenzylamino)purine riboside, 2-(amino, hydroxy, chloro, fluoro, bromo, methyl or methylmercapto)-6-(2-bromobenzylamino)purine riboside, 2-(amino, hydroxy, chloro, fluoro, bromo, methyl or methylmercapto)-6-(3-bromobenzylamino)purine riboside, 2-(amino, hydroxy, chloro, fluoro, bromo, methyl or methylmercapto)-6-(4-bromobenzylamino)purine riboside, 2-(amino, hydroxy, chloro, fluoro, bromo, methyl or methylmercapto)-6-(2-iodobenzylamino)purine riboside, 2-(amino, hydroxy, chloro, fluoro, bromo, methyl or methylmercapto)-6-(3-iodobenzylamino)purine riboside, 2-(amino, hydroxy, chloro, fluoro, bromo, methyl or methylmercapto)-6-(4-iodobenzylamino)purine riboside, 2-(amino, hydroxy, chloro, fluoro, bromo, methyl or methylmercapto)-6-(2-chlorobenzylamino)purine riboside, 2-(amino, hydroxy, chloro, fluoro, bromo, methyl or methylmercapto)-6-(2-chlorobenzylamino)purine riboside, 2-(amino, hydroxy, chloro, fluoro, bromo, methyl or methylmercapto)-6-(3-chlorobenzylamino)purine riboside, 6-(4-chlorobenzylamino)purine riboside, 2-(amino, hydroxy, chloro, fluoro, bromo, methyl or methylmercapto)-6-(2-acetylbenzylamino)purine riboside, 2-(amino, hydroxy, chloro, fluoro, bromo, methyl or methylmercapto)-6-(3-acetylbenzylamino)purine riboside, 2-(amino, hydroxy, chloro, fluoro, bromo, methyl or methylmercapto)-6-(4-acetylbenzylamino)purine riboside, 2-(amino, hydroxy, chloro, fluoro, bromo, methyl or methylmercapto)-6-(3-carboxybenzylamino)purine riboside, 2-(amino, hydroxy, chloro, fluoro, bromo, methyl or methylmercapto)-6-(4-carboxybenzylamino)purine riboside, 6-(2-acetoxybenzylamino)purine riboside, 2-(amino, hydroxy, chloro, fluoro, bromo, methyl or methylmercapto)-6-(3-acetoxybenzylamino)purine riboside, 2-(amino, hydroxy, chloro, fluoro, bromo, methyl or methylmercapto)-6-(4-acetoxybenzylamino)purine riboside, 2-(amino, hydroxy, chloro, fluoro, bromo, methyl or methylmercapto)-6-(2-nitrobenzylamino)purine riboside, 2-(amino, hydroxy, chloro, fluoro, bromo, methyl or methylmercapto)-6-(3-nitrobenzylamino)purine riboside, 2-(amino, hydroxy, chloro, fluoro, bromo, methyl or methylmercapto)-6-(4-nitrobenzylamino)purine riboside, 2-(amino, hydroxy, chloro, fluoro, bromo, methyl or methylmercapto)-6-(2-sulphobenzylamino)purine riboside, 2-(amino, hydroxy, chloro, fluoro, bromo, methyl or methylmercapto)-6-(3-sulphoobenzylamino)purine riboside, 2-(amino, hydroxy, chloro, fluoro, bromo, methyl or methylmercapto)-6-(4-sulphobenzylamino)purine riboside, 2-(amino, hydroxy, chloro, fluoro, bromo, methyl or methylmercapto)-6-(2-cyanobenzylamino)purine riboside, 2-(amino, hydroxy, chloro, fluoro, bromo, methyl or methylmercapto)-6-(3-cyanobenzylamino)purine riboside, 6-(4-cyanobenzylamino)purine riboside, 2-(amino, hydroxy, chloro, fluoro, bromo, methyl or methylmercapto)-6-(5-nitro-2-methylbenzylamino)purine riboside, 2-(amino, hydroxy, chloro, fluoro, bromo, methyl or methylmercapto)-6-(2-methylbenzylamino)purine riboside, 2-(amino, hydroxy, chloro, fluoro, bromo, methyl or methylmercapto)-6-(3-methylbenzylamino)purine riboside, 6-(4-methylbenzylamino)purine riboside, 2-(amino, hydroxy, chloro, fluoro, bromo, methyl or methylmercapto)-6-(4-methylaminobenzylamino)purine riboside, 6-(2-methoxybenzylamino)purine riboside, 2-(amino, hydroxy, chloro, fluoro, bromo, methyl or methylmercapto)-6-(3-methoxybenzylamino)purine riboside, 2-(amino, hydroxy, chloro, fluoro, bromo, methyl or methylmercapto)-6-(4-methoxybenzylamino)purine riboside, 2-(amino, hydroxy, chloro, fluoro, bromo, methyl or methylmercapto)-6-(2-hydroxybenzylamino)purine riboside, 2-(amino, hydroxy, chloro, fluoro, bromo, methyl or methylmercapto)-6-(3-hydroxybenzylamino)purine riboside, 2-(amino, hydroxy, chloro, fluoro, bromo, methyl or methylmercapto)-6-(4-hydroxybenzylamino)purine riboside, 2-(amino, hydroxy, chloro, fluoro, bromo, methyl or methylmercapto)-6-(4-hexylbenzylamino)purine riboside, 2-(amino, hydroxy, chloro, fluoro, bromo, methyl or methylmercapto)-6-(4-hexyloxybenzylamino)purine riboside, 2-(amino, hydroxy, chloro, fluoro, bromo, methyl or methylmercapto)-6-(2-formylbenzylamino)purine riboside, 2-(amino, hydroxy, chloro, fluoro, bromo, methyl or methylmercapto)-6-(3-formylbenzylamino)purine riboside, 2-(amino, hydroxy, chloro, fluoro, bromo, methyl or methylmercapto)-6-(4-formylbenzylamino)purine riboside, 2-(amino, hydroxy, chloro, fluoro, bromo, methyl or methylmercapto)-6-(2-ethoxybenzylamino)purine riboside, 2-(amino, hydroxy, chloro, fluoro, bromo, methyl or methylmercapto)-6-(3-ethoxybenzylamino)purine riboside, 2-(amino, hydroxy, chloro, fluoro, bromo, methyl or methylmercapto)-6-(4-ethoxybenzylamino)purine riboside, 2-(amino, hydroxy, chloro, fluoro, bromo, methyl or methylmercapto)-6-(4-ethylbenzylamino)purine riboside, 2-(amino, hydroxy, chloro, fluoro, bromo, methyl or methylmercapto)-6-(4-penthylbenzylamino)purine riboside, 2-(amino, hydroxy, chloro, fluoro, bromo, methyl or methylmercapto)-6-(4-penthyloxybenzylamino)purine riboside, 2-(amino, hydroxy, chloro, fluoro, bromo, methyl or methylmercapto)-6-(4-phenoxybenzylamino)purine riboside, 2-(amino, hydroxy, chloro, fluoro, bromo, methyl or methylmercapto)-6-(4-phenylbenzylamino)purine riboside, 2-(amino, hydroxy, chloro, fluoro, bromo, methyl or methylmercapto)-6-(4-propylbenzylamino)purine riboside, 2-(amino, hydroxy, chloro, fluoro, bromo, methyl or methylmercapto)-6-(4-propyloxybenzylamino)purine riboside, 2-(amino, hydroxy, chloro, fluoro, bromo, methyl or methylmercapto)-6-(4-oktylbenzylamino)purine riboside, 2-(amino, hydroxy, chloro, fluoro, bromo, methyl or methylmercapto)-6-(4-octyloxybenzylamino)purine riboside, 2-(amino, hydroxy, chloro, fluoro, bromo, methyl or methylmercapto)-6-(4-ethyloxybenzylamino)purine riboside, 2-(amino, hydroxy, chloro, fluoro, bromo, methyl or methylmercapto)-6-(3,4-diacetoxybenzylamino)purine riboside, 2-(amino, hydroxy, chloro, fluoro, bromo, methyl or methylmercapto)-6-(3,5-diacetoxybenzylamino)purine riboside, 6-(2,5-diaminobenzylamino)purine riboside, 2-(amino, hydroxy, chloro, fluoro, bromo, methyl or methylmercapto)-6-(3,5-dibromobenzylamino)purine riboside, 2-(amino, hydroxy, chloro, fluoro, bromo, methyl or methylmercapto)-6-(3,5-dibromo-4-methoxybenzylamino)purine riboside, 2-(amino, hydroxy, chloro, fluoro, bromo, methyl or methylmercapto)-6-(2,3-dichlorobenzylamino)purine riboside, 2-(amino, hydroxy, chloro, fluoro, bromo, methyl or methylmercapto)-6-(2,4-dichlorobenzylamino)purine riboside, 2-(amino, hydroxy, chloro, fluoro, bromo, methyl or methylmercapto)-6-(2,5-dichlorobenzylamino)purine riboside, 2-(amino, hydroxy, chloro, fluoro, bromo, methyl or methylmercapto)-6-(2,6-dichlorobenzylamino)purine riboside, 2-(amino, hydroxy, chloro, fluoro, bromo, methyl or methylmercapto)-6-(3,4-dichlorobenzylamino)purine riboside, 2-(amino, hydroxy, chloro, fluoro, bromo, methyl or methylmercapto)-6-(3,5-dichlorobenzylamino)purine riboside, 2-(amino, hydroxy, chloro, fluoro, bromo, methyl or methylmercapto)-6-(2,3,4,5-tetrafluorobenzylamino)purine riboside, 2-(amino, hydroxy, chloro, fluoro, bromo, methyl or methylmercapto)-6-(2-chloro-3,6-difluorobenzylamino)purine riboside, 2-(amino, hydroxy, chloro, fluoro, bromo, methyl or methylmercapto)-6-(5-chloro-2-fluorobenzylamino)purine riboside, 2-(amino, hydroxy, chloro, fluoro, bromo, methyl or methylmercapto)-6-(2,3,4-trifluorobenzylamino)purine riboside, 2-(amino, hydroxy, chloro, fluoro, bromo, methyl or methylmercapto)-6-(2,3,5-trifluorobenzylamino)purine riboside, 2-(amino, hydroxy, chloro, fluoro, bromo, methyl or methylmercapto)-6-(2,4,5-trifluorobenzylamino)purine riboside, 2-(amino, hydroxy, chloro, fluoro, bromo, methyl or methylmercapto)-6-(3,4,5-trifluorobenzylamino)purine riboside, 2-(amino, hydroxy, chloro, fluoro, bromo, methyl or methylmercapto)-6-(2,3,6-trifluorobenzylamino)purine riboside, 2-(amino, hydroxy, chloro, fluoro, bromo, methyl or methylmercapto)-6-(3-chloro-2,6-difluorobenzylamino)purine riboside, 2-(amino, hydroxy, chloro, fluoro, bromo, methyl or methylmercapto)-6-(2-chloro-6-fluorobenzylamino)purine riboside, 2-(amino, hydroxy, chloro, fluoro, bromo, methyl or methylmercapto)-6-(2,6-difluorobenzylamino)purine riboside, 2-(amino, hydroxy, chloro, fluoro, bromo, methyl or methylmercapto)-6-(2,4-difluorobenzylamino)purine riboside, 2-(amino, hydroxy, chloro, fluoro, bromo, methyl or methylmercapto)-6-(3,4-difluorobenzylamino)purine riboside, 2-(amino, hydroxy, chloro, fluoro, bromo, methyl or methylmercapto)-6-(2,5-difluorobenzylamino)purine riboside, 2-(amino, hydroxy, chloro, fluoro, bromo, methyl or methylmercapto)-6-(3,5-difluorobenzylamino)purine riboside, 2-(amino, hydroxy, chloro, fluoro, bromo, methyl or methylmercapto)-6-(5-fluoro-2-(trifluoromethyl)benzylamino)purine riboside, 2-(amino, hydroxy, chloro, fluoro, bromo, methyl or methylmercapto)-6-(4-fluoro-2-(trifluoromethyl)benzylamino) purine riboside, 2-(amino, hydroxy, chloro, fluoro, bromo, methyl or methylmercapto)-6-(2-chloro-5-(trifluoromethyl)benzylamino)purine riboside, 2-(amino, hydroxy, chloro, fluoro, bromo, methyl or methylmercapto)-6-(2-(difluoromethoxy)benzylamino)purine riboside, 2-(amino, hydroxy, chloro, fluoro, bromo, methyl or methylmercapto)-6-(3-(difluoromethoxy)benzylamino)purine riboside, 2-(amino, hydroxy, chloro, fluoro, bromo, methyl or methylmercapto)-6-(4-(difluoromethoxy)benzylamino)purine riboside, 2-(amino, hydroxy, chloro, fluoro, bromo, methyl or methylmercapto)-6-(2-fluoro-5-(trifluoromethyl)benzylamino)purine riboside, 2-(amino, hydroxy, chloro, fluoro, bromo, methyl or methylmercapto)-6-(3-fluoro-4-(trifluoromethyl)benzylamino)purine riboside, 2-(amino, hydroxy, chloro, fluoro, bromo, methyl or methylmercapto)-6-(2-fluoro-4-(trifluoromethyl)benzylamino)purine riboside, 2-(amino, hydroxy, chloro, fluoro, bromo, methyl or methylmercapto)-6-(2-(trifluoromethylthio)benzylamino)purine riboside, 2-(amino, hydroxy, chloro, fluoro, bromo, methyl or methylmercapto)-6-(2-fluoro-3-(trifluoromethyl)benzylamino)purine riboside, 2-(amino, hydroxy, chloro, fluoro, bromo, methyl or methylmercapto)-6-(2-chloro-6-fluoro-3-methylbenzylamino)purine purine riboside, 2-(amino, hydroxy, chloro, fluoro, bromo, methyl or methylmercapto)-6-(6-chloro-2-fluoro-3-methylbenzylamino)purine riboside, 2-(amino, hydroxy, chloro, fluoro, bromo, methyl or methylmercapto)-6-(3-chloro-2-fluoro-5-(trifluoromethyl)benzylamino)purine riboside, 2-(amino, hydroxy, chloro, fluoro, bromo, methyl or methylmercapto)-6-(3-chloro-2-fluoro-6-(trifluoromethyl)benzylamino)purine riboside, 2-(amino, hydroxy, chloro, fluoro, bromo, methyl or methylmercapto)-6-(2,3-difluoro-4-methylbenzylamino)purine riboside, 2-(amino, hydroxy, chloro, fluoro, bromo, methyl or methylmercapto)-6-(2,6-difluoro-3-methylbenzylamino)purine riboside, 2-(amino, hydroxy, chloro, fluoro, bromo, methyl or methylmercapto)-6-(2-fluoro-6-(trifluoromethyl)benzylamino)purine riboside, 2-(amino, hydroxy, chloro, fluoro, bromo, methyl or methylmercapto)-6-(3-chloro-2,6-difluorobenzylamino)purine riboside, 2-(amino, hydroxy, chloro, fluoro, bromo, methyl or methylmercapto)-6-(3-(trifluoromethylthio)benzylamino)purine riboside, 2-(amino, hydroxy, chloro, fluoro, bromo, methyl or methylmercapto)-6-(3-fluoro-4-methyl benzylamino)purine riboside, 2-(amino, hydroxy, chloro, fluoro, bromo, methyl or methylmercapto)-6-(4-fluoro-3-methylbenzylamino)purine riboside, 2-(amino, hydroxy, chloro, fluoro, bromo, methyl or methylmercapto)-6-(5-fluoro-2-methylbenzylamino)purine riboside, 2-(amino, hydroxy, chloro, fluoro, bromo, methyl or methylmercapto)-6-(2-chloro-3,6-difluorobenzylamino)puri riboside, 2-(amino, hydroxy, chloro, fluoro, bromo, methyl or methylmercapto)-6-(4-(trifluoromethylthio)benzylamino) purine riboside, 2-(amino, hydroxy, chloro, fluoro, bromo, methyl or methylmercapto)-6-(3-fluoro-5-(trifluoromethyl) benzylamino)purine riboside, 2-(amino, hydroxy, chloro, fluoro, bromo, methyl or methylmercapto)-6-(2-chloro-4-fluorobenzylamino)purine riboside, 2-(amino, hydroxy, chloro, fluoro, bromo, methyl or methylmercapto)-6-(2-(trifluoromethoxy)benzylamino)purine riboside, 6-(3-(trifluoromethyl)benzylamino)purine riboside, 2-(amino, hydroxy, chloro, fluoro, bromo, methyl or methylmercapto)-6-(2-(trifluoromethyl)benzylamino)purine riboside, 2-(amino, hydroxy, chloro, fluoro, bromo, methyl or methylmercapto)-6-(4-(trifluoromethyl)benzylamino)purine riboside, 2-(amino, hydroxy, chloro, fluoro, bromo, methyl or methylmercapto)-6-(4-chloro-3-(trifluoromethyl)benzylamino) purine riboside, 2-(amino, hydroxy, chloro, fluoro, bromo, methyl or methylmercapto)-6-(4-fluoro-3-(trifluoromethyl) benzylamino)purine riboside, 2-(amino, hydroxy, chloro, fluoro, bromo, methyl or methylmercapto)-6-(3,5-bis(trifluoromethyl)benzylamino)purine riboside, 2-(amino, hydroxy, chloro, fluoro, bromo, methyl or methylmercapto)-6-(3-(trifluoromethoxy)benzylamino)purine riboside, 2-(amino, hydroxy, chloro, fluoro, bromo, methyl or methylmercapto)-6-(4-(trifluoromethoxy)benzylamino)purine riboside, 2-(amino, hydroxy, chloro, fluoro, bromo, methyl or methylmercapto)-6-(4-(trifluoromethyl)benzylamino)purine riboside, 2-(amino, hydroxy, chloro, fluoro, bromo, methyl or methylmercapto)-6-(4-diethylaminobenzylamino)purine riboside, 2-(amino, hydroxy, chloro, fluoro, bromo, methyl or methylmercapto)-6-(3,4-dihydroxybenzylamino)purine riboside, 2-(amino, hydroxy, chloro, fluoro, bromo, methyl or methylmercapto)-6-(3,5-dihydroxybenzylamino)purine riboside, 2-(amino, hydroxy, chloro, fluoro, bromo, methyl or methylmercapto)-6-(3,4-dihydroxybenzylamino)purine riboside, 2-(amino, hydroxy, chloro, fluoro, bromo, methyl or methylmercapto)-6-(2,3-ethylenedioxybenzylamino)purine riboside, 2-(amino, hydroxy, chloro, fluoro, bromo, methyl or methylmercapto)-6-(2,4-dihydroxybenzylamino)purine, 2-(amino, hydroxy, chloro, fluoro, bromo, methyl or methylmercapto)-6-(2,5-dihydroxybenzylamino)purine riboside, 2-(amino, hydroxy, chloro, fluoro, bromo, methyl or methylmercapto)-6-(2,6-dihydroxybenzylamino)purine riboside, 2-(amino, hydroxy, chloro, fluoro, bromo, methyl or methylmercapto)-6-(3,4-dimethoxybenzylamino)purine riboside, 2-(amino, hydroxy, chloro, fluoro, bromo, methyl or methylmercapto)-6-(3,4-dimethoxybenzylamino)purine riboside, 2-(amino, hydroxy, chloro, fluoro, bromo, methyl or methylmercapto)-6-(3,5-dimethoxybenzylamino)purine riboside, 2-(amino, hydroxy, chloro, fluoro, bromo, methyl or methylmercapto)-6-(2,3-dimethoxybenzylamino)purine riboside, 2-(amino, hydroxy, chloro, fluoro, bromo, methyl or methylmercapto)-6-(2,4-dimethoxybenzylamino)purine riboside, 2-(amino, hydroxy, chloro, fluoro, bromo, methyl or methylmercapto)-6-(2,5-dimethoxybenzylamino)purine riboside, 2-(amino, hydroxy, chloro, fluoro, bromo, methyl or methylmercapto)-6-(2,6-dimethoxybenzylamino)purine riboside, 2-(amino, hydroxy, chloro, fluoro, bromo, methyl or methylmercapto)-6-(2-hydroxy-3-methoxybenzylamino)purine riboside, 2-(amino, hydroxy, chloro, fluoro, bromo, methyl or methylmercapto)-6-(2-hydroxy-4-methoxybenzylamino)purine riboside, 2-(amino, hydroxy, chloro, fluoro, bromo, methyl or methylmercapto)-6-(2-hydroxy-5-methoxybenzylamino)purine riboside, 2-(amino, hydroxy, chloro, fluoro, bromo, methyl or methylmercapto)-6-(2-hydroxy-6-methoxybenzylamino)purine riboside, 2-(amino, hydroxy, chloro, fluoro, bromo, methyl or methylmercapto)-6-(3-hydroxy-2-methoxybenzylamino)purine riboside, 2-(amino, hydroxy, chloro, fluoro, bromo, methyl or methylmercapto)-6-(3-hydroxy-4-methoxybenzylamino)purine riboside, 2-(amino, hydroxy, chloro, fluoro, bromo, methyl or methylmercapto)-6-(3-hydroxy-5-methoxybenzylamino)purine riboside, 2-(amino, hydroxy, chloro, fluoro, bromo, methyl or methylmercapto)-6-(3-hydroxy-6-methoxybenzylamino)purine riboside, 2-(amino, hydroxy, chloro, fluoro, bromo, methyl or methylmercapto)-6-(4-hydroxy-2-methoxybenzylamino)purine riboside, 2-(amino, hydroxy, chloro, fluoro, bromo, methyl or methylmercapto)-6-(4-hydroxy-3-methoxybenzylamino)purine riboside, 2-(amino, hydroxy, chloro, fluoro, bromo, methyl or methylmercapto)-6-(4-hydroxy-5-methoxybenzylamino)purine riboside, 2-(amino, hydroxy, chloro, fluoro, bromo, methyl or methylmercapto)-6-(4-hydroxy-6-methoxybenzylamino)purine riboside, 2-(amino, hydroxy, chloro, fluoro, bromo, methyl or methylmercapto)-6-(2-hydroxy-3,4-dimethoxybenzylamino)purine riboside, 2-(amino, hydroxy, chloro, fluoro, bromo, methyl or methylmercapto)-6-(2-hydroxy-3,5-dimethoxybenzylamino)purine riboside, 2-(amino, hydroxy, chloro, fluoro, bromo, methyl or methylmercapto)-6-(2-hydroxy-3,6-dimethoxybenzylamino)purine riboside, 2-(amino, hydroxy, chloro, fluoro, bromo, methyl or methylmercapto)-6-(2-hydroxy-4,5-dimethoxybenzylamino)purine riboside, 2-(amino, hydroxy, chloro, fluoro, bromo, methyl or methylmercapto)-6-(2-hydroxy-4,6-dimethoxybenzylamino)purine riboside, 2-(amino, hydroxy, chloro, fluoro, bromo, methyl or methylmercapto)-6-(2-hydroxy-5,6-dimethoxybenzylamino)purine riboside, 2-(amino, hydroxy, chloro, fluoro, bromo, methyl or methylmercapto)-6-(3-hydroxy-4,5-dimethoxybenzylamino)purine riboside, 2-(amino, hydroxy, chloro, fluoro, bromo, methyl or methylmercapto)-6-(3-hydroxy-4,6-dimethoxybenzylamino)purine riboside, 2-(amino, hydroxy, chloro, fluoro, bromo, methyl or methylmercapto)-6-(3-hydroxy-2,4-dimethoxybenzylamino)purine riboside, 2-(amino, hydroxy, chloro, fluoro, bromo, methyl or methylmercapto)-6-(3-hydroxy-2,5-dimethoxybenzylamino)purine riboside, 2-(amino, hydroxy, chloro, fluoro, bromo, methyl or methylmercapto)-6-(3-hydroxy-2,6-dimethoxybenzylamino)purine riboside, 2-(amino, hydroxy, chloro, fluoro, bromo, methyl or methylmercapto)-6-(4-hydroxy-2,3-dimethoxybenzylamino)purine riboside, 2-(amino, hydroxy, chloro, fluoro, bromo, methyl or methylmercapto)-6-(4-hydroxy-2,5-dimethoxybenzylamino)purine riboside, 2-(amino, hydroxy, chloro, fluoro, bromo, methyl or methylmercapto)-6-(4-hydroxy-2,6-dimethoxybenzylamino)purine riboside, 2-(amino, hydroxy, chloro, fluoro, bromo, methyl or methylmercapto)-6-(4-hydroxy-3,5-dimethoxybenzylamino)purine riboside, 2-(amino, hydroxy, chloro, fluoro, bromo, methyl or methylmercapto)-6-(4-hydroxy-3,6-dimethoxybenzylamino)purine riboside, 2-(amino, hydroxy, chloro, fluoro, bromo, methyl or methylmercapto)-6-(2,3-dihydroxy-4-methoxybenzylamino)purine riboside, 2-(amino, hydroxy, chloro, fluoro, bromo, methyl or methylmercapto)-6-(2,3-dihydroxy-5-methoxybenzylamino)purine riboside, 2-(amino, hydroxy, chloro, fluoro, bromo, methyl or methylmercapto)-6-(2,3-dihydroxy-6-methoxybenzylamino)purine riboside, 2-(amino, hydroxy, chloro, fluoro, bromo, methyl or methylmercapto)-6-(2,4-dihydroxy-3-methoxybenzylamino)purine riboside, 2-(amino, hydroxy, chloro, fluoro, bromo, methyl or methylmercapto)-6-(2,4-dihydroxy-5-methoxybenzylamino)purine riboside, 2-(amino, hydroxy, chloro, fluoro, bromo, methyl or methylmercapto)-6-(2,4-dihydroxy-6-methoxybenzylamino)purine riboside, 2-(amino, hydroxy, chloro, fluoro, bromo, methyl or methylmercapto)-6-(2,5-dihydroxy-3-methoxybenzylamino)purine riboside, 2-(amino, hydroxy, chloro, fluoro, bromo, methyl or methylmercapto)-6-(2,5-dihydroxy-4-methoxybenzylamino)purine riboside, 2-(amino, hydroxy, chloro, fluoro, bromo, methyl or methylmercapto)-6-(2,5-dihydroxy-6-methoxybenzylamino)purine riboside, 2-(amino, hydroxy, chloro, fluoro, bromo, methyl or methylmercapto)-6-(2,6-dihydroxy-3-methoxybenzylamino)purine riboside, 2-(amino, hydroxy, chloro, fluoro, bromo, methyl or methylmercapto)-6-(2,6-dihydroxy-4-methoxybenzylamino)purine riboside, 2-(amino, hydroxy, chloro, fluoro, bromo, methyl or methylmercapto)-6-(2,6-dihydroxy-5-methoxybenzylamino)purine riboside, 2-(amino, hydroxy, chloro, fluoro, bromo, methyl or methylmercapto)-6-(3,4-dihydroxy-2-methoxybenzylamino)purine riboside, 2-(amino, hydroxy, chloro, fluoro, bromo, methyl or methylmercapto)-6-(3,4-dihydroxy-5-methoxybenzylamino)purine riboside, 2-(amino, hydroxy, chloro, fluoro, bromo, methyl or methylmercapto)-6-(3,4-dihydroxy-6-methoxybenzylamino)purine riboside, 2-(amino, hydroxy, chloro, fluoro, bromo, methyl or methylmercapto)-6-(3,5-dihydroxy-2-methoxybenzylamino)purine riboside, 2-(amino, hydroxy, chloro, fluoro, bromo, methyl or methylmercapto)-6-(3,5-dihydroxy-4-methoxybenzylamino)purine riboside, 2-(amino, hydroxy, chloro, fluoro, bromo, methyl or methylmercapto)-6-(3,5-dihydroxy-6-methoxybenzylamino)purine riboside, 2-(amino, hydroxy, chloro, fluoro, bromo, methyl or methylmercapto)-6-(2,3,4-trimethoxybenzylamino)purine riboside, 2-(amino, hydroxy, chloro, fluoro, bromo, methyl or methylmercapto)-6-(2,4,5-trimethoxybenzylamino)purine riboside, 2-(amino, hydroxy, chloro, fluoro, bromo, methyl or methylmercapto)-6-(2,4,6-trimethoxybenzylamino)purine riboside, 2-(amino, hydroxy, chloro, fluoro, bromo, methyl or methylmercapto)-6-(3,4,5-trimethoxybenzylamino)purine riboside, 2-(amino, hydroxy, chloro, fluoro, bromo, methyl or methylmercapto)-6-(2-hydroxy-3,4,5-trimethoxybenzylamino)purine riboside, 2-(amino, hydroxy, chloro, fluoro, bromo, methyl or methylmercapto)-6-(2-hydroxy-3,4,6-trimethoxybenzylamino)purine riboside, 2-(amino, hydroxy, chloro, fluoro, bromo, methyl or methylmercapto)-6-(2-hydroxy-4,5,6-trimethoxybenzylamino)purine riboside, 2-(amino, hydroxy, chloro, fluoro, bromo, methyl or methylmercapto)-6-(2,4,6-trimethoxybenzylamino)purine riboside, 2-(amino, hydroxy, chloro, fluoro, bromo, methyl or methylmercapto)-6-(2,3,4-trihydroxybenzylamino)purine riboside, 2-(amino, hydroxy, chloro, fluoro, bromo, methyl or methylmercapto)-6-(2,4,6-trihydroxybenzylamino)purine riboside, 2-(amino, hydroxy, chloro, fluoro, bromo, methyl or methylmercapto)-6-(2,3,4-trihydroxybenzylamino)purine riboside, 2-(amino, hydroxy, chloro, fluoro, bromo, methyl or methylmercapto)-6-(3,4,5-trihydroxybenzylamino)purine riboside, 2-(amino, hydroxy, chloro, fluoro, bromo, methyl or methylmercapto)-6-(2,4,6-trihydroxybenzylamino)purine riboside, 2-(amino, hydroxy, chloro, fluoro, bromo, methyl or methylmercapto)-6-(2-hydroxy-3-chlorobenzylamino)purine riboside, 2-(amino, hydroxy, chloro, fluoro, bromo, methyl or methylmercapto)-6-(2-hydroxy-4-chlorobenzylamino)purine riboside, 2-(amino, hydroxy, chloro, fluoro, bromo, methyl or methylmercapto)-6-(2-hydroxy-5-chlorobenzylamino)purine riboside, 2-(amino, hydroxy, chloro, fluoro, bromo, methyl or methylmercapto)-6-(2-hydroxy-6-chlorobenzylamino)purine riboside, 2-(amino, hydroxy, chloro, fluoro, bromo, methyl or methylmercapto)-6-(2-hydroxy-3-iodobenzylamino)purine riboside, 2-(amino, hydroxy, chloro, fluoro, bromo, methyl or methylmercapto)-6-(2-hydroxy-4-iodobenzylamino)purine riboside, 2-(amino, hydroxy, chloro, fluoro, bromo, methyl or methylmercapto)-6-(2-hydroxy-5-iodobenzylamino)purine riboside, 2-(amino, hydroxy, chloro, fluoro, bromo, methyl or methylmercapto)-6-(2-hydroxy-6-iodobenzylamino)purine riboside, 2-(amino, hydroxy, chloro, fluoro, bromo, methyl or methylmercapto)-6-(2-hydroxy-3-bromobenzylamino)purine riboside, 2-(amino, hydroxy, chloro, fluoro, bromo, methyl or methylmercapto)-6-(2-hydroxy-4-bromobenzylamino)purine riboside, 2-(amino, hydroxy, chloro, bromo, methyl or methylmercapto)-6-(2-hydroxy-5-bromobenzylamino)purine riboside, 2-(amino, hydroxy, chloro, fluoro, bromo, methyl or methylmercapto)-6-(2-hydroxy-6-bromobenzylamino)purine riboside, 2-(amino, hydroxy, chloro, fluoro, bromo, methyl or methylmercapto)-6-(2-hydroxy-3-fluorobenzylamino)purine riboside, 2-(amino, hydroxy, chloro, fluoro, bromo, methyl or methylmercapto)-6-(2-hydroxy-4-fluorobenzylamino)purine riboside, 2-(amino, hydroxy, chloro, fluoro, bromo, methyl or methylmercapto)-6-(2-hydroxy-5-fluorobenzylamino)purine riboside, 2-(amino, hydroxy, chloro, fluoro, bromo, methyl or methylmercapto)-6-(2-hydroxy-6-fluorobenzylamino)purine riboside, 2-(amino, hydroxy, chloro, fluoro, bromo, methyl or methylmercapto)-6-(2-hydroxy-3-methylbenzylamino)purine riboside, 2-(amino, hydroxy, chloro, fluoro, bromo, methyl or methylmercapto)-6-(2-hydroxy-4-methylbenzylamino)purine riboside, 2-(amino, hydroxy, chloro, fluoro, bromo, methyl or methylmercapto)-6-(2-hydroxy-5-methylbenzylamino)purine riboside, 2-(amino, hydroxy, chloro, fluoro, bromo, methyl or methylmercapto)-6-(2-hydroxy-6-methylbenzylamino)purine riboside, 2-(amino, hydroxy, chloro, fluoro, bromo, methyl or methylmercapto)-6-(2,3-dihydroxy-4-chlorobenzylamino)purine riboside, 2-(amino, hydroxy, chloro, fluoro, bromo, methyl or methylmercapto)-6-(2,3-dihydroxy-5-chlorobenzylamino)purine riboside, 2-(amino, hydroxy, chloro, fluoro, bromo, methyl or methylmercapto)-6-(2,5-dihydroxy-4-chlorobenzylamino)purine riboside, 2-(amino, hydroxy, chloro, fluoro, bromo, methyl or methylmercapto)-6-(2,6-dihydroxy-4-chlorobenzylamino)purine riboside, 2-(amino, hydroxy, chloro, fluoro, bromo, methyl or methylmercapto)-6-(2,6-dihydroxy-4-bromoxybenzylamino)purine riboside, 2-(amino, hydroxy, chloro, fluoro, bromo, methyl or methylmercapto)-6-(2,6-dihydroxy-4-iodobenzylamino)purine riboside, 2-(amino, hydroxy, chloro, fluoro, bromo, methyl or methylmercapto)-6-(2,6-dihydroxy-3-chlorobenzylamino)purine riboside, 2-(amino, hydroxy, chloro, fluoro, bromo, methyl or methylmercapto)-6-(2,6-dihydroxy-3-bromobenzylamino)purine riboside, 2-(amino, hydroxy, chloro, fluoro, bromo, methyl or methylmercapto)-6-(2,6-dihydroxy-3-iodobenzylamino)purine riboside, 2-(amino, hydroxy, chloro, fluoro, bromo, methyl or methylmercapto)-6-(2,6-dihydroxy-3-fluorobenzylamino)purine riboside, 2-(amino, hydroxy, chloro, fluoro, bromo, methyl or methylmercapto)-6-(2,6-dihydroxy-3,5-dichlorobenzylamino)purine riboside, 2-(amino, hydroxy, chloro, fluoro, bromo, methyl or methylmercapto)-6-(2,6-dihydroxy-3,5-dibromobenzylamino)purine riboside, 2-(amino, hydroxy, chloro, fluoro, bromo, methyl or methylmercapto)-6-(2,6-dihydroxy-3,5-diiodobenzylamino)purine riboside, 2-(amino, hydroxy, chloro, fluoro, bromo, methyl or methylmercapto)-6-(2,6-dihydroxy-3,5-difluorobenzylamino)purine riboside, 2-(amino, hydroxy, chloro, fluoro, bromo, methyl or methylmercapto)-6-(4,5-dimethoxy-2-nitrobenzylamino)purine riboside, 2-(amino, hydroxy, chloro, fluoro, bromo, methyl or methylmercapto)-6-(3,4-dimethylbenzylamino)purine riboside, 2-(amino, hydroxy, chloro, fluoro, bromo, methyl or methylmercapto)-6-(2,3-dimethylbenzylamino)purine riboside, 2-(amino, hydroxy, chloro, fluoro, bromo, methyl or methylmercapto)-6-(2,4-dimethylbenzylamino)purine riboside, 2-(amino, hydroxy, chloro, fluoro, bromo, methyl or methylmercapto)-6-(2,6-dimethylbenzylamino)purine riboside, 2-(amino, hydroxy, chloro, fluoro, bromo, methyl or methylmercapto)-6-(2,6-dimethyl-4-hydroxybenzylamino)purine riboside, 2-(amino, hydroxy, chloro, fluoro, bromo, methyl or methylmercapto)-6-(3,5-dimethyl-4-hydroxybenzylamino)purine riboside, 2-(amino, hydroxy, chloro, fluoro, bromo, methyl or methylmercapto)-6-(2-fluoro-4-hydroxybenzylamino)purine riboside, 2-(amino, hydroxy, chloro, fluoro, bromo, methyl or methylmercapto)-6-(3-fluoro-4-methylbenzylamino)purine riboside, 2-(amino, hydroxy, chloro, fluoro, bromo, methyl or methylmercapto)-6-(3,4-dinitrobenzylamino)purine riboside, 2-(amino, hydroxy, chloro, fluoro, bromo, methyl or methylmercapto)-6-(3,5-dinitrobenzylamino)purine riboside, 2-(amino, hydroxy, chloro, fluoro, bromo, methyl or methylmercapto)-6-(2-methyl-5-nitrobenzylamino)purine riboside, 2-(amino, hydroxy, chloro, fluoro, bromo, methyl or methylmercapto)-6-(3-methyl-4-nitrobenzylamino)purine riboside, 2-(amino, hydroxy, chloro, fluoro, bromo, methyl or methylmercapto)-6-(3,4-diiodo-4-hydroxybenzylamino)purine riboside, 2-(amino, hydroxy, chloro, fluoro, bromo, methyl or methylmercapto)-6-(2-chloro-3,4-dimethoxybenzylamino)purine riboside, 2-(amino, hydroxy, chloro, fluoro, bromo, methyl or methylmercapto)-6-(4-chloro-3,5-dinitrobenzylamino)purine riboside, 2-(amino, hydroxy, chloro, fluoro, bromo, methyl or methylmercapto)-6-(2-chloro-4-fluorobenzylamino)purine riboside, 2-(amino, hydroxy, chloro, fluoro, bromo, methyl or methylmercapto)-6-(3-chloro-4-fluorobenzylamino)purine riboside, 2-(amino, hydroxy, chloro, fluoro, bromo, methyl or methylmercapto)-6-(2-chloro-6-methylbenzylamino)purine riboside, 2-(amino, hydroxy, chloro, fluoro, bromo, methyl or methylmercapto)-6-(3-chloro-2-methylbenzylamino)purine riboside, 2-(amino, hydroxy, chloro, fluoro, bromo, methyl or methylmercapto)-6-(3-chloro-4-methylbenzylamino)purine riboside, 2-(amino, hydroxy, chloro, fluoro, bromo, methyl or methylmercapto)-6-(5-chloro-2-methoxybenzylamino)purine riboside, 2-(amino, hydroxy, chloro, fluoro, bromo, methyl or methylmercapto)-6-(2-chloro-4-fluorobenzylamino)purine riboside, 2-(amino, hydroxy, chloro, fluoro, bromo, methyl or methylmercapto)-6-(4-chloromethylbenzylamino)purine riboside, 2-(amino, hydroxy, chloro, fluoro, bromo, methyl or methylmercapto)-6-(2-chloro-5-nitrobenzylamino)purine riboside, 2-(amino, hydroxy, chloro, fluoro, bromo, methyl or methylmercapto)-6-(2-chloro-6-nitrobenzylamino)purine riboside, 2-(amino, hydroxy, chloro, fluoro, bromo, methyl or methylmercapto)-6-(4-chloro-3-nitrobenzylamino)purine riboside, 2-(amino, hydroxy, chloro, fluoro, bromo, methyl or methylmercapto)-6-(5-chloro-2-nitrobenzylamino)purine riboside, 2-(amino, hydroxy, chloro, fluoro, bromo, methyl or methylmercapto)-6-(3-bromo-4-hydroxybenzylamino)purine riboside, 2-(amino, hydroxy, chloro, fluoro, bromo, methyl or methylmercapto)-6-(3,5-dibromo-4-hydroxybenzylamino)purine, 2-(amino, hydroxy, chloro, fluoro, bromo, methyl or methylmercapto)-6-(3-bromo-4-methoxybenzylamino)purine, 2-(amino, hydroxy, chloro, fluoro, bromo, methyl or methylmercapto)-6-(4-bromomethylbenzylamino)purine riboside, 2-(amino, hydroxy, chloro, fluoro, bromo, methyl or methylmercapto)-6-(4-butoxybenzylamino)purine riboside, 2-(amino, hydroxy, chloro, fluoro, bromo, methyl or methylmercapto)-6-(4-butoxybenzylamino)purine riboside, 2-(amino, hydroxy, chloro, fluoro, bromo, methyl or methylmercapto)-6-(4-/t-butyl/benzylamino)purine riboside, 2-(amino, hydroxy, chloro, fluoro, bromo, methyl or methylmercapto)-6-(4-t-butyl-2,6-dimethylbenzylamino)purine riboside, 2-(amino, hydroxy, chloro, fluoro, bromo, methyl or methylmercapto)-6-(2-aminobenzylamino)purine riboside, 2-(amino, hydroxy, chloro, fluoro, bromo, methyl or methylmercapto)-6-(3-aminobenzylamino)purine riboside, 2-(amino, hydroxy, chloro, fluoro, bromo, methyl or methylmercapto)-6-(4-aminobenzylamino)purine riboside, 2-(amino, hydroxy, chloro, fluoro, bromo, methyl or methylmercapto)-6-(2-amino-3-chlorobenzylamino)purine riboside, 2-(amino, hydroxy, chloro, fluoro, bromo, methyl or methylmercapto)-6-(2-amino-4-chlorobenzylamino)purine riboside, 2-(amino, hydroxy, chloro, fluoro, bromo, methyl or methylmercapto)-6-(2-amino-5-chlorobenzylamino)purine riboside, 2-(amino, hydroxy, chloro, fluoro, bromo, methyl or methylmercapto)-6-(2-amino-6-chlorobenzylamino)purine riboside, 2-(amino, hydroxy, chloro, fluoro, bromo, methyl or methylmercapto)-6-(3-amino-2-chlorobenzylamino)purine riboside, 2-(amino, hydroxy, chloro, fluoro, bromo, methyl or methylmercapto)-6-(3-amino-4-chlorobenzylamino)purine riboside, 2-(amino, hydroxy, chloro, fluoro, bromo, methyl or methylmercapto)-6-(3-amino-5-chlorobenzylamino)purine riboside, 2-(amino, hydroxy, chloro, fluoro, bromo, methyl or methylmercapto)-6-(3-amino-6-chlorobenzylamino)purine riboside, 2-(amino, hydroxy, chloro, fluoro, bromo, methyl or methylmercapto)-6-(2,6-diamino-3-chlorobenzylamino)purine riboside, 2-(amino, hydroxy, chloro, fluoro, bromo, methyl or methylmercapto)-6-(2,6-diamino-4-chlorobenzylamino)purine riboside, 2-(amino, hydroxy, chloro, fluoro, bromo, methyl or methylmercapto)-6-(4-amino-3-chlorobenzylamino)purine riboside, 2-(amino, hydroxy, chloro, fluoro, bromo, methyl or methylmercapto)-6-(4-amino-5-dichlorobenzylamino)purine riboside, 2-(amino, hydroxy, chloro, fluoro, bromo, methyl or methylmercapto)-6-(5-amino-2-methylbenzylamino)purine riboside, 2-(amino, hydroxy, chloro, fluoro, bromo, methyl or methylmercapto)-6-(2-amino-3-nitrobenzylamino)purine riboside, 2-(amino, hydroxy, chloro, fluoro, bromo, methyl or methylmercapto)-6-(4-amino-3-nitrobenzylamino)purine riboside, 2-(amino, hydroxy, chloro, fluoro, bromo, methyl or methylmercapto)-6-(4-benzyloxybenzylamino)purine riboside, 2-(amino, hydroxy, chloro, fluoro, bromo, methyl or methylmercapto)-6-(3-acetylbenzylamino) purine riboside, 2-(amino, hydroxy, chloro, fluoro, bromo, methyl or methylmercapto)-6-(2-acetylbenzylamino)purine riboside, 2-(amino, hydroxy, chloro, fluoro, bromo, methyl or methylmercapto)-6-(2,4,5-trichlorobenzylamino)purine riboside, 2-(amino, hydroxy, chloro, fluoro, bromo, methyl or methylmercapto)-6-(2,4,5-trichlorobenzylamino)purine riboside, 2-(amino, hydroxy, chloro, fluoro, bromo, methyl or methylmercapto)-6-(2,4,6-trichlorobenzylamino)purine riboside, 2-(amino, hydroxy, chloro, fluoro, bromo, methyl or methylmercapto)-6-(2,3,4-trichlorobenzylamino)purine riboside, 6-(2,3,5-trichlorobenzylamino)purine riboside, 2-(amino, hydroxy, chloro, fluoro, bromo, methyl or methylmercapto)-6-(2,3,6-trichlorobenzylamino)purine riboside, 2-(amino, hydroxy, chloro, fluoro, bromo, methyl or methylmercapto)-6-(2,5,6-trichlorobenzylamino)purine riboside.

The starting material for the preparation of the compounds of the general formula I is 6-chloropurine riboside, synthesised from hypoxanthine using $POCl_3$ according to the literature (Davoll and Blowy, J. Am. Chem. Soc. 73:2936 (1957)) or commercially available (Sigma, Aldrich, Fluka).

Another starting material for the preparation of the compounds of the general formula I is 6-bromopurine riboside, synthesised from adenine or hypoxanthine using n-pentyl nitrite in tribromomethane, or commercially available. Another starting material for the preparation of the compounds of the general formula I is 6-fluoropurine riboside, which can be prepared from 6-chloropurine riboside by the reaction with triethylamine affording quarternary ammonium salt, which can be converted by the reaction with tetrabutylammonium triphenydifluorosilicate in dimethylformamid to 6-fluoropurine riboside (Gurvich et al., Nucleos. Nucleot. 18: 2327 (1999)).

Yet another starting material for the preparation of the compounds of the general formula I are substituted benzylamines. Those bearing one or more hydroxyl groups are not commercially available and may be prepared by demethylation of appropriate methoxyderivatives using 48% HBr in $N_2$ atmosphere.

A further object of the invention is a method of preparation of substitution derivatives of $N^6$-benzyladenosine of the general formula I, wherein $R_1$ and $R_2$ have above mentioned meanings, comprising nucleophilic substitution of heterocyclic derivative of formula I, wherein $R_3$ represents bromine, chlorine or fluorine or methylmercapto group and $R_2$ have above mentioned meanings, in order to convert chlorine, bromine, or methylmercapto group at 6 position to any other meaning of substituent $R_1$, as described above, to obtain the compound of general formula I.

Use of corresponding 2-chloro, 2-hydroxy, 2-amino, and 2-methylmercapto derivatives of 6-chloropurine riboside is advantegeous for their preparation (Nair and Young, Synthesis 6: 450 (1986); Nair and Fasbender, Tetrahedron 49: 2169 (1993).

Object of the invention are substitution derivatives of $N^6$-benzyladenosine of the general formula I for use as drugs.

A further object of the invention are derivatives of $N^6$-benzyladenosine of formula I for use as growth regulators of plant, mammal, microorganisms, yeast and fungal cells.

This invention also concerns substitution derivatives of $N^6$-benzyladenosine of formula I for use as cosmetics.

Another object of the present invention are also pharmaceuticals, cosmetics or growth regulators, which contain compound of formula I or their pharmaceutically acceptable salt, including a pharmaceutical carrier.

A further object of this invention is the use of substitution derivatives of $N^6$-benzyladenosine of formula I, for preparation of affinity absorption matrices, immobilised enzymes for process control, immunoassay reagents, diagnostic samples, as well as compounds and oligonucleotides, labeled by $^{14}C$, $^3H$, avidin or biotin.

This invention also concerns method of using a compound of formula I or its pharmaceutically acceptable salt, including a pharmaceutical carrier, for preparation of a pharmaceutical composition destined for use as mitotic or antimitotic compound, especially for treating cancer, psoriasis, rheumatoid arthritis, lupus, type I diabetes, multiple sclerosis, restenosis, polycystic kidney disease, graft rejection, graft versus host disease and gout, parasitoses such as those caused by fungi or protists, or Alzheimer's disease, or as antineurogenerative drugs, or to suppress immunostimulation.

Object of the invention is further the use of substitution derivatives of $N^6$-benzyladenosine of formula I for use as growth regulators in agriculture, especially for increasing of yield and quality of agricultural products.

This invention also concerns substitution derivatives of $N^6$-benzyladenosine of formula I for use as cosmetics for inhibiting ageing and senescence of mammalian epidermal cells, such as keratinocytes or fibroblasts.

A further object of this invention is the use of substitution derivatives of $N^6$-benzyladenosine of formula I as growth regulator in tissue cultures for stimulation of proliferation and morphogenesis.

This invention also concerns substitution derivatives of $N^6$-benzyladenosine of formula I for the preparation of a composition and its using for plant and mammalian embryonic cells and embryos (esp. oocytes) cloning.

This invention also concerns substitution derivatives of $N^6$-benzyladenosine of formula I, for preparation of a composition and its using for suppressing immunostimulation e.g. in arthritis or in suppression of transplant rejection in mammals.

Therapeutic Administration

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition comprise about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, dextran, polyvinylpyrrolidone or gelatine.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Húls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethylstarch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alcohols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration, can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, of hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminium silicates, which have the task of binding the moisture or secretions present.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The present invention further provides veterinary compositions comprising at least one active ingredient as above defined together with a veterinary carrier therefor. Veterinary carriers are materials for administering the composition and may be solid, liquid or gaseous materials, which are inert or acceptable in the veterinary art and are compatible with the active ingredient. These veterinary compositions may be administered orally, parenterally or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 50 g, preferably 0.5 g to about 10 g, of a compound of the present invention is administered here for a body weight of about 70 kg.

FIGURES

FIG. 1: Protein $p21^{WAF-1}$ induction in MCF-7 cells after treatment by different concentrations of 2OH3MeOBAPR.

FIG. 2: Protein p21$^{WAF-1}$ induction in MCF-7 cells 6-24 hours after application of 2OH3MeOBAPR in 1 μM concentration.

FIG. 3: Inhibition of growth of carcinoma cell line CEM (A) and HL60 (B) by new cytokinins. Cytotoxicity was measured using Calcein AM assay. Activity is presented as percentage of maximal activity (in absence of inhibitors). ZR: zeatin riboside; oTR: ortho-topolin riboside; 3F-BAPR: 6-(3-fluorobenzylamino)purine riboside; 3Cl-4FBAPR: 6-(3-chloro-4-fluorobenzylamino)purine riboside; 2OH3MeOBAPR: 6-(2-hydroxy-3-methoxybenzylamino)purine riboside.

FIG. 4. Inhibition of HL-60 cell proliferation induced by 2OH3MeOBAPR. 2OH3MeOBAPR was added to the exponentially growing cells in following concentrations: 2.5 μM (●), 5 μM (□), 10 μM (■), 20 μM (Δ), 40 μM (▲) and 60 μM (○). Control cells cultivated on standard media without 2OH3MeOBAPR (○).

FIG. 5. Induction of apoptosis by 2OH3MeOBAPR in HL-60 cells. Different concentrations of 2OH3MeOBAPR were added to the exponentially growing cells. Number of apoptotic cells (with respect to the nucleus morphology) was monitored after 24 h of incubation. Control cells were cultivated on standard media without 2OH3MeOBAPR.

FIG. 6. Effect of 2OH3MeOBAPR on HL-60 cell nuclear morphology. Nuclei of cells cultivated at standard conditions on media without 2OH3MeOBAPR a), nuclei of cells cultivated on media containing 5 μM 2OH3MeOBAPR for 24 hours b)

FIG. 7. Effect of 2OH3MeOBAPR on nuclear DNA integrity of HL-60 cells. M—molecular weight standards. Line 1—DNA isolated from cells cultivated on media without 2OH3MeOBAPR. Line 2-6 DNA isolated from cells cultivated on media containing 5, 10, 20 40 and 60 μM 2OH3MeOBAPR for 24 h.

FIG. 8. Effect of 2OH3MeOBAPR (6-(2-hydroxy-3-methoxybenzylamino)purine riboside) on cell cycle. Cells were cultivated a) in standard media without 2OH3MeOBAPR (control), b) in media containing 5 μM 2OH3MeOBAPR for 24 h prior analysis by flow-cytometry.

FIG. 9. Effect of 2OH3MeOBAPR on caspase proteases. Cells cultivated in standard media without 2OH3MeOBAPR (white bars), Cells cultivated in media containing 20 μM 2OH3MeOBAPR (black bars). Relative substrate hydrolysis for caspase-9 Ac-LEHD-AFC a) and caspase-3 Ac-DEVD-AMC b).

FIG. 10: Effect of caspase inhibitor Z-VAD-FMK on viability HL-60 cells cultivated in presence of 2OH3MeOBAPR. Exponencially growing cells were cultivated for 72 h with 20 μM 2OH3MeOBAPR (white bars) and comdination of 20 μM 2OH3MeOBAPR and 50 μM Z-VAD-FMK (black bars). Cell viability was measured during the incubation using combined FDA/PI staining.

FIG. 11: Effect of adenosine kinase inhibitor, 4-amino-3-iodo-1β-D-ribofuranosylpyrazolo [3,4-d]-pyrimidine (AIRPP), on viability of HL-60 cells cultivated in presence of 2OH3MeOBAPR. Exponencially growing cells were cultivated for 72 h with 20 μM 2OH3MeOBAPR (white bars) and comdination of 20 μM 2OH3MeOBAPR and 1 μM AIRPP (black bars). Cell viability was measured during the incubation using combined FDA/PI staining.

FIG. 12: Effect of tested compounds on retention of chlorophyll in excised wheat leaf tips. Values are expressed % of initial chlorophyll content of fresh leaves before the incubation. Dashed line indicates control incubation without any cytokinin, which was 57.7±0.9.

FIG. 13: Effect of tested compounds on fresh weight yield of tobacco callus culture. Error bars show standard deviation of the mean for 5 replicate determination. Line -●- indicates the value for the control treatment without any cytokinin, 2.5±0.3 g.

FIG. 14: Effect of tested compounds on dark induction of betacyanin synthesis in *Amarantus caudatus* cotyledons/hypocotyls explants. Values represent the difference in O.D. units between absorption at 537 and 620 nm.

FIG. 15: Relative number of with at least one brown leaf in function of culture time (■: BAP, ●: mT, ▲: mMeOBAPR)

FIG. 16: Relative number of dead explants in relation to culture time (■: BA, ●: mT, ▲: mMeOBAPR)

FIG. 17: Left: dead *Rosa* explant on BA containing medium; right: vigorous *Rosa* plantlet after 121 days of cultivation on mMeOBAPR containing medium

EXAMPLES

The following examples serve to illustrate the invention without limiting the scope thereof.

Example 1

3 mmol of 6-chloropurine riboside were dissolved in 15 ml of butanol. Subsequently, 4 mmol of 2,3,6-trifluorobenzylamine and 5 mmol of triethylamine were added and mixture was heated at 90° C. for 4 hours. After cooling, the precipitated product was filtered off and crystallised from ethanol. M.p. 196° C. TLC: chloroform-methanol-ammonia (90:9:0.1) single spot. Yield 92%.

TABLE 1

Compounds Prepared by the Method of Example 1

| | Elemental analyses calculated/found | | | ES-MS | Melting point |
|---|---|---|---|---|---|
| Substituent | % C | % H | % N | [M + H⁺] | (° C.) |
| 2-fluorobenzylamino | 54.4/54.1 | 4.8/4.8 | 18.7/18.4 | 376 | 191-192 |
| 3-fluorobenzylamino | 54.4/53.9 | 4.8/4.7 | 18.7/18.2 | 376 | 153-154 |
| 4-fluorobenzylamino | 54.4/54.3 | 4.8/4.8 | 18.7/18.3 | 376 | 177-178 |
| 2-chlorobenzylamino | 52.1/52.0 | 4.6/4.7 | 17.9/17.5 | 392 | 183-184 |
| 3-chlorobenzylamino | 52.1/51.9 | 4.6/4.6 | 17.9/17.3 | 392 | 164-165 |
| 4-chlorobenzylamino | 52.1/51.8 | 4.6/4.5 | 17.9/17.1 | 392 | 181-182 |
| 2-bromobenzylamino | 46.8/46.3 | 4.16/4.1 | 16.05/15.5 | 436 | 180-181 |
| 3-bromobenzylamino | 46.8/47.8 | 4.16/4.5 | 16.05/15.6 | 436 | 173-174 |
| 4-bromobenzylamino | 46.8/46.9 | 4.16/4.3 | 16.05/15.4 | 436 | 175-176 |
| 3-jodobenzylamino | 41.0/41.4 | 2.8/2.8 | 20.0/19.5 | 484 | 184-185 |

TABLE 1-continued

Compounds Prepared by the Method of Example 1

| Substituent | Elemental analyses calculated/found | | | ES-MS | Melting point |
| --- | --- | --- | --- | --- | --- |
| | % C | % H | % N | [M + H$^+$] | (° C.) |
| 2-methylbenzylamino | 58.2/57.88 | 5.7/5.5 | 18.86/18.3 | 372 | 174-175 |
| 3-methylbenzylamino | 58.2/57.9 | 5.7/5.44 | 18.86/18.2 | 372 | 162-163 |
| 4-methylbenzylamino | 58.2/58.5 | 5.7/5.9 | 18.86/18.3 | 372 | 164-166 |
| 2-methoxylbenzylamino | 55.8/54.95 | 5.46/5.2 | 18.1/17.73 | 388 | 164-166 |
| 3-methoxylbenzylamino | 55.8/55.5 | 5.46/5.7 | 18.1/17.96 | 388 | 162-163 |
| 4-methoxylbenzylamino | 55.8/55.33 | 5.46/5.2 | 18.1/17.7 | 388 | 154-156 |
| 2,4-dichlorobenzylamino | 47.9/47.98 | 4.0/4.03 | 16.4/15.9 | 426 | 205-206 |
| 3,4-dichlorobenzylamino | 47.9/47.3 | 4.0/4.3 | 16.4/16.12 | 426 | 194-195 |
| 2,3-dihydroxybenzylamino | 52.4/52.1 | 4.9/5.0 | 18.0/18.2 | 390 | 184-186 |
| 3,5-dihydroxybenzylamino | 52.4/52.2 | 4.9/5.2 | 18.0/17.6 | 390 | 187-188 |
| 2-hydroxy-3-methoxybenzylamino | 53.6/54.0 | 5.2/5.4 | 17.4/17.1 | 404 | 208-209 |
| 3-hydroxy-4-methoxybenzylamino | 53.6/53.1 | 5.2/5.6 | 17.4/17.0 | 404 | 218-219 |
| 2,3-dimethoxybenzylamino | 54.7/54.8 | 5.6/5.5 | 16.8/16.4 | 418 | 177-179 |
| 2,4-dimethoxybenzylamino | 54.7/54.3 | 5.6/5.7 | 16.8/16.3 | 418 | 208-210 |
| 3,4-dimethoxybenzylamino | 54.7/54.45 | 5.6/5.5 | 16.8/16.3 | 418 | 156-157 |
| 3,5-dimethoxybenzylamino | 54.67/54.7 | 5.6/5.5 | 16.8/16.4 | 418 | 174-175 |
| 4-hydroxy-3,5-dimethoxybenzylamino | 52.6/52.5 | 5.3/5.2 | 16.2/16.3 | 434 | 200-201 |
| 2,4-difluorobenzylamino | 51.9/51.4 | 4.4/4.3 | 17.8/17.7 | 394 | 171-172 |
| 3,5-difluorobenzylamino | 51.9/51.2 | 4.4/4.3 | 17.8/17.6 | 394 | 178-178 |
| 2,3,4-trifluorobenzylamino | 49.6/49.1 | 3.9/3.7 | 17.0/16.8 | 412 | 192-193 |
| 2,4,5-trifluorobenzylamino | 49.6/49.0 | 3.9/3.8 | 17.0/16.4 | 412 | 175-176 |
| 2,3,6-trifluorobenzylamino | 49.6/49.0 | 3.9/3.7 | 17.0/16.4 | 412 | 195-196 |
| 3-chloro-4-fluorobenzylamino | 49.8/49.2 | 4.2/4.1 | 17.1/16.8 | 411 | 148-149 |

Example 2

3 mmol of 6-chloropurine riboside were dissolved in 15 ml of butanol. Subsequently, 4 mmol of 2-hydroxy-3-methoxybenzylamine and 5 mmol of diisopropylethylamine were added and mixture was heated at 60° C. for 8 hours. After cooling, the precipitated product was filtered off and recrystallised from ethanol. M.p. 209° C. TLC: chloroform-methanol-ammonia (90:9:0.1) single spot. Yield 92%.

Example 3

3 mmol of 6-fluoropurine riboside were dissolved in 15 ml of isopropanol. Subsequently, 8 mmol of 2,3-dihydroxybenzylamine hydrobromide and 10 mmol of triethylamine were added and mixture was heated at 60° C. for 6 hours. After cooling, the precipitated product was filtered off and recrystallised from ethanol. M.p. 196° C. TLC: chloroform-methanol-ammonia (90:9:0.1) single spot. Yield 89%.

TABLE 2

Compounds Prepared by the Method of Example 2

| Substituent | Elemental analyses calculated/found | | | ES-MS | Melting point |
| --- | --- | --- | --- | --- | --- |
| | % C | % H | % N | [M + H$^+$] | (° C.) |
| 2-methoxybenzylamino | 55.8/55.5 | 5.5/5.7 | 18.1/18.3 | 388 | 165-166 |
| 3-methoxybenzylamino | 55.8/55.5 | 5.46/5.7 | 18.1/17.96 | 388 | 163-164 |
| 4-methoxybenzylamino | 55.8/55.33 | 5.46/5.2 | 18.1/17.7 | 388 | 156-157 |
| 2,3-dimethoxybenzylamino | 54.7/54.5 | 5.6/5.7 | 16.8/17.0 | 418 | 178-179 |
| 2,4-dimethoxybenzylamino | 54.7/54.4 | 5.6/5.7 | 16.8/16.9 | 418 | 209-210 |
| 3,4-dimethoxybenzylamino | 54.7/54.5 | 5.6/5.5 | 16.8/16.3 | 418 | 157-158 |
| 3,5-dimethoxybenzylamino | 54.7/54.7 | 5.6/5.5 | 16.8/16.4 | 418 | 176-177 |
| 2-hydroxy-3-methoxybenzylamino | 53.6/53.3 | 5.2/5.3 | 17.4/17.6 | 404 | 209-211 |
| 3-hydroxy-4-methoxybenzylamino | 53.6/53.3 | 5.2/5.4 | 17.4/17.6 | 404 | 219-220 |
| 4-hydroxy-3,5-dimethoxybenzylamino | 52.6/52.4 | 5.3/5.4 | 16.2/16.3 | 434 | 202-203 |

TABLE 3

Compounds Prepared by the Method of Example 3

| Substituent | Elemental analyses calculated/found | | | ES-MS [M + H⁺] |
|---|---|---|---|---|
| | % C | % H | % N | |
| 2,3-dihydroxybenzylamino | 52.4/52.2 | 4.9/5.0 | 18.0/18.2 | 390 |
| 3,5-dihydroxybenzylamino | 52.4/52.2 | 4.9/5.0 | 18.0/17.8 | 390 |
| 2-hydroxy-3-methoxybenzylamino | 53.6/53.9 | 5.2/5.3 | 17.4/17.2 | 404 |
| 3-hydroxy-4-methoxybenzylamino | 53.6/53.3 | 5.2/5.4 | 17.4/17.2 | 404 |
| 2,3-dimethoxybenzylamino | 54.7/54.8 | 5.6/5.5 | 16.8/16.6 | 418 |
| 2,4-dimethoxybenzylamino | 54.7/54.3 | 5.6/5.7 | 16.8/16.5 | 418 |
| 3,4-dimethoxybenzylamino | 54.7/54.5 | 5.6/5.5 | 16.8/16.5 | 418 |
| 3,5-dimethoxybenzylamino | 54.7/54.7 | 5.6/5.5 | 16.8/16.6 | 418 |
| 4-hydroxy-3,5-dimethoxybenzylamino | 52.6/52.3 | 5.3/5.2 | 16.2/16.4 | 434 |

Example 4

2-chloro-6-(3-methoxybenzylamino)purine riboside 3 mmol of 2,6-dichloropurine riboside were dissolved in 15 ml of butanol. Subsequently, 4 mmol of 3-methoxybenzylamine and 5 mmol of triethylamine were added and mixture was heated at 90° C. for 4 hours. After cooling, the precipitated product was filtered off and recrystallised from ethanol. TLC: chloroform-methanol-ammonia (90:9:1) single spot. Yield 85%.

TABLE 4

Compounds Prepared by the Method of Example 4

| Substituent ($R_2$ = Cl) | Elemental analyses calculated/found | | | ES-MS [M + H⁺] |
|---|---|---|---|---|
| | % C | % H | % N | |
| 2-methylbenzylamino | 53.3/52.8 | 5.0/5.2 | 17.3/17.6 | 406 |
| 3-methylbenzylamino | 53.3/52.7 | 5.0/5.3 | 17.3/17.8 | 406 |
| 4-methylbenzylamino | 53.3/52.9 | 5.0/5.2 | 17.3/17.6 | 406 |
| 2-methoxybenzylamino | 51.2/50.6 | 4.8/5.0 | 16.6/16.9 | 422 |
| 3-methoxybenzylamino | 51.2/50.9 | 4.8/4.9 | 16.6/17.0 | 422 |
| 4-methoxybenzylamino | 51.2/50.7 | 4.8/5.0 | 16.6/16.9 | 422 |
| 2,3-dimethoxybenzylamino | 50.5/50.0 | 4.9/4.7 | 15.5/15.8 | 452 |
| 2,4-dimethoxybenzylamino | 50.5/50.2 | 4.9/4.9 | 15.5/15.6 | 452 |
| 3,4-dimethoxybenzylamino | 50.5/49.7 | 4.9/4.5 | 15.5/16.1 | 452 |
| 3,5-dimethoxybenzylamino | 50.5/50.2 | 4.9/4.7 | 15.5/15.8 | 452 |

Example 5

2-amino-6-(2-methoxybenzylamino)purine riboside 3 mmol of 2-amino-6-chloropurine riboside were dissolved in 15 ml of butanol. Subsequently, 4 mmol of 3-methoxybenzylamine and 5 mmol of triethylamine were added and mixture was heated at 90° C. for 4 hours. After cooling, the precipitated product was filtered off and recrystallised from ethanol. TLC: chloroform-methanol-ammonia (90:9:1), single spot. Yield 86%

TABLE 5

Compounds Prepared by the Method of Example 5

| Substituent ($R_2$ = $NH_2$) | Elemental analyses calculated/found | | | ES-MS [M + H⁺] |
|---|---|---|---|---|
| | % C | % H | % N | |
| 2-methylbenzylamino | 56.0/55.4 | 5.7/5.9 | 16.6/16.9 | 387 |
| 3-methylbenzylamino | 56.0/55.6 | 5.7/5.7 | 16.6/16.9 | 387 |
| 4-methylbenzylamino | 56.0/55.6 | 5.7/5.8 | 16.6/16.7 | 387 |
| 2-methoxybenzylamino | 53.7/53.1 | 5.5/5.7 | 20.9/21.2 | 403 |
| 3-methoxybenzylamino | 53.7/53.2 | 5.5/5.7 | 20.9/21.3 | 403 |
| 4-methoxybenzylamino | 53.7/53.3 | 5.5/5.6 | 20.9/21.2 | 403 |
| 2,3-dimethoxybenzylamino | 52.8/52.4 | 5.6/5.7 | 19.4/19.6 | 403 |
| 2,4-dimethoxybenzylamino | 52.8/52.5 | 5.6/5.7 | 19.4/19.6 | 433 |
| 3,4-dimethoxybenzylamino | 52.8/52.0 | 5.6/6.0 | 19.4/19.9 | 433 |
| 3,5-dimethoxybenzylamino | 52.8/52.1 | 5.6/5.9 | 19.4/19.9 | 433 |

Example 6

Inhibition of Senescence of Mammal Cells

In this example, human diploid fibroblasts (HCA cells with different levels of passage: passage 25—labelling HCA25; passage 45—labelling HCA45; passage 80—labelling HCA80) were used for studying β-galactosidase activity. Medium used for cells cultivation was removed, cells were washed twice with PBS and fixed in 2-3 ml of fixation agent consisting of 2% of formaldehyde and 0.2% of flutaraldehyde in PBS. Cells were incubated at room temperature for 5 min and subsequently washed twice with PBS. Cells were then incubated at 37° C. (without $CO_2$) for 1 to 16 hours in 2-3 ml of solution comprising potassium ferricyanide (5 mM), potassium ferrocyanide (5 mM), $MgCl_2$ (2 mM), X-gal (5-bromo-4-chloro-3-indolyl-β-D-galactopyranoside) (1 mg/ml) in citrate/phosphate buffer, pH 6.0. After this incubation period the cells were observed with microscope in order to detect senescent cells or measure the intensity of coloration at 415 nm spectrophotometrically with reader Multiscam MCC (Lab-systems)—positively senescent cells. In this experiment only senescent cells were labelled due to the effect of β-galactosidase on the substrate.

TABLE 6

Effect of the new compounds on the number of senescent cells in the culture of human fibroblasts

| Substituent R6 | Senescent cells (%) | | |
|---|---|---|---|
| | HCA25 | HCA45 | HCA80 |
| control | 3 | 5 | 38 |
| Kinetin | 3 | 5 | 25 |
| 3-chloroanilino | 4 | 4 | 27 |
| anilino | 4 | 5 | 25 |
| 3-chloro-5-aminoanilino | 4 | 5 | 23 |
| 4-bromoanilino | 5 | 5 | 21 |
| 4-chloroanilino | 4 | 6 | 25 |
| 3-amino-4-chloroanilino | 3 | 5 | 24 |
| 2-methoxybenzylamino | 4 | 4 | 16 |
| 3-methoxybenzylamino | 5 | 6 | 12 |
| 2,3-dimethoxybenzylamino | 4 | 5 | 18 |
| 2-methoxy-3-chlorobenzylamino | 4 | 5 | 18 |
| 2-fluorobenzylamino | 4 | 4 | 15 |
| 3-fluorobenzylamino | 3 | 5 | 13 |
| 3-amino-4-chlorobenzylamino | 4 | 6 | 22 |
| 2,3-diamino-4-chlorobenzylamino | 3 | 4 | 19 |

In Table 6 it is shown that with increasing number of passages the level of coloration after addition of β-galactosidase substrate was increasing. In the oldest cultures only blue-coloured cells were found, whose colour differed between clear blue and matt blue. $N^6$-substituted derivatives were efficient in retardation of cell senescence after 80 passages. In case of long-term cultivation these cells were able to survive 40% longer in comparison with control cells.

Example 7

2-methylthio-6-(3-methylbenzylamino)purine riboside

The reaction mixture, containing 2-methylthioxanthine (65 g), $POCl_3$ (975 ml) and N,N-diethylaniline (97.5 ml), was refluxed for 1.5 h with continuous stirring. Entire excess of $POCl_3$ was evaporated to dryness in vacuo and the residue was poured on crushed ice (1.75 kg) in 10 l vessel (without additional cooling). After being stirred for additional 10 min. ($POCl_3$ hydrolysis completion), the mixture was subsequently extracted by ethylacetate (4×2.5 l). Extracts were combined, washed with water (3×1 l) and dried. Crude product was crystallised from ethanol and subsequently dried using $P_2O_5$ to the constant weight. Yield 23.6 g (33%). UV purity 99%. HPLC (25×O.4 cm ODS. From 0 to 30% of acetonitrile. 1 ml/min. 3O min) Rt 26.8 min. Purity 92%. TLC (chloroform/methanol. 9/1) single spot, Rf 0.80

2-Methylthio-6-chloropurine (4 g, dried using $P_2O_5$ to the constant weight) was mixed with β-D-ribofuranosyl-1,2,3,5-tetraacetate (6.4 g) at 145-150° C. (paraffin bath). 100 mg of iodine was added and mixture was dried for 30 min under vacuum. Black residue was dissolved in chloroform, filtered, then applied in 100 ml of mixture ethylacetate/toluen (1/4) on column and chromatographed over silicagel (2×400 g). The mixture of ethylacetate/toluen (3/7) was used as a mobile phase. Fraction composition was monitored using TLC. The mixture of ethylacetate/toluen (1/2) was used as mobile phase (starting compound Rf=0.06, product 0.25). Major product (71%), β isomer, was completely separated from α isomer and other impurities. Brown syrup was dried under vacuum, dissolved in dry methanol, cooled and deacetylated over night in 1000 ml of dry methanol saturated with ammonia. Mixture was evaporated and product crystallized in hot water. Resulting yellow crystals were dried using $P_2O_5$ to the constant weight. Yield 4.95 g (18.6%). M.p. 187-188° C. HPLC purity (25 cm ODS 0-30% of acetonitrile)=91%.

3.3 g (10 mmol) of 2-methylthio-6-chloropurine-β-D-ribofuranoside were added into a solution of 3-methylbenzylamine in butanol (100 ml) containing triethylamine (7.8 ml). Mixture was refluxed for 2 hours. Butanol was evaporated yielding white product, which was subsequently resuspended in water (50 ml). Suspension pH was adjusted at 8-8.5 using 2 M NaOH and the suspension was stored over night at 4° C. The precipitated solid was filtered off and crystallised from ethanol. White product was subsequently dried using $P_2O_5$ to the constant weight. Yield 3.1 g. (81.4%). HPLC purity 98.6%.

TABLE 7

Compounds Prepared by the Method of Example 7

| Substituent | Elemental analyses calculated/found | | | ES-MS |
|---|---|---|---|---|
| ($R_2$ = methylthio) | % C | % H | % N | [M + H⁺] |
| 2-methylbenzylamino | 58.9/58.2 | 5.3/5.6 | 24.5/24.8 | 286 |
| 3-methylbenzylamino | 58.9/58.4 | 5.3/5.6 | 24.5/24.8 | 286 |

TABLE 7-continued

Compounds Prepared by the Method of Example 7

| Substituent | Elemental analyses calculated/found | | | ES-MS |
|---|---|---|---|---|
| ($R_2$ = methylthio) | % C | % H | % N | [M + H⁺] |
| 4-methylbenzylamino | 58.9/58.1 | 5.3/5.9 | 24.5/25.0 | 286 |
| 2-methoxybenzylamino | 55.8/55.0 | 5.0/5.4 | 23.2/23.8 | 302 |
| 3-methoxybenzylamino | 55.8/55.5 | 5.0/5.1 | 23.2/23.3 | 302 |
| 4-methoxybenzylamino | 55.8/55.3 | 5.0/5.3 | 23.2/23.6 | 302 |

Example 8

Induction of $p21^{WAF-1}$ protein, the natural cyclin-dependent kinases inhibitor, by cytokinines' activity in brest cancer cell line MCF-7—molecular mechanism of the effect.

$p21^{WAF-1}$ Protein Level Changes in Dependence on the 6-(2-hydroxy-3-methoxybenzylamino) purine riboside (2OH3MeOBAPR) concentration MCF-7 cells cultured at 37° C. in 5% $CO_2$ atmosphere in D-MEM medium supplemented with 10% foetal calf serum were treated with 2OH3MeOBAPR concentrations range of 0-100 μM. 2OH3MeOBAPR was added into the medium from the 100 mM storage solution in DMSO. Cells were harvested after 12 hours incubation with 2OH3MeOBAPR, centrifuged (1000 rpm, 4° C., 5 min), washed twice by ice-cold PBS and re-centrifuged. These washed cells were then lysed by 1×CSB (loading buffer for SDS-PAGE, i.e. electrophoresis of proteins in polyacrylamide gel containing SDS). Cell lysate proteins were separated by SDS-PAGE and transferred onto a nitrocelulose (NC) membrane. NC membrane was blocked by 5% skimmed milk, 0.1% Tween 20 in PBS. Protein level of $p21^{WAF-1}$ and actin (as a loaded protein volume control) were detected immunochemically using commercially available specific monoclonal antibodies anti-$p21^{WAF-1}$ (Ab-1, Calbiochem) and anti-Actin (Clone AC-40, Sigma-Aldrich). The primary antibodies bind to target proteins were detected using rabbit secondary peroxidase-labeled antibody (RAM-Px, DAKO), followed by chemiluminiscence (ECL, Amersham-Pharmacia). Efficient $p21^{WAF-1}$ protein induction is achieved in MCF-7 cells by treating these cells with 2OH3MeOBAPR at concentration rank of units of μmol/liter of culture medium (FIG. 1).

$p21^{WAF-1}$ Protein Level Changes in Dependence on the Duration of Incubation with 2OH3MeOBAPR MCF-7 cells were incubated in presence of 1 μM 2OH3MeOBAPR. Treated cells were harvested and lysed after various time periods of 2OH3MeOBAPR treatment. Subsequent SDS-PAGE and immunodetection enable us to detect $p21^{WAF-1}$ protein level depending on the duration of incubation with 2OH3MeOBAPR. The cultivation of cells, harvesting, lysis and the detection of $p21^{WAF-1}$ and actin proteins in cell lysates was similar to paragraph no. 1. Efficient $p21^{WAF-1}$ protein induction is achieved in MCF-7 cells in the range of 6-24 hours after 1 μM 2OH3MeOBAPR adition (FIG. 2).

Example 9

In Vitro Cytotoxic Activity of Novel Compounds

One of the parameters used, as the basis for cytotoxicity assays, is the metabolic activity of viable cells. For example, a microtiter assay, which uses the Calcein AM, is now widely used to quantitate cell proliferation and cytotoxicity. For instance, this assay is used in drug screening programs and in chemosensitivity testing. Because only metabolically active cells cleave Calcein AM, these assays detect viable cells exclusively. The quantity of reduced Calcein AM corresponds to the number of vital cells in the culture.

Human T-lymphoblastic leukemia cell line CEM; promyelocytic HL-60 and monocytic U937 leukemias; breast carcinoma cell lines MCF-7; cervical carcinoma cells HELA; mouse fibroblasts NIH3T3; human erythroleukaemia K562 and human malignant melanoma cells G361 were used for routine screening of compounds. The cells were maintained in Nunc/Corning 80 cm$^2$ plastic tissue culture flasks and cultured in cell culture medium (DMEM with 5 g/l glucose, 2 mM glutamine, 100 U/ml penicillin, 100 µg/ml streptomycin, 10% fetal calf serum and sodium bicarbonate).

The cell suspensions that were prepared and diluted according to the particular cell type and the expected target cell density (10$^4$ cells per well based on cell growth characteristics) were added by pipette (80 µl) into 96/well microtiter plates. Inoculates were allowed a pre-incubation period of 24 hours at 37° C. and 5% CO$_2$ for stabilisation. Four-fold dilutions of the intended test concentration were added at time zero in 20 µl aliquots to the microtiter plate wells. Usually, test compound was evaluated at six 4-fold dilutions. In routine testing, the highest well concentration was 166.7 µM, but it can be the matter of change dependent on the agent. All drug concentrations were examined in duplicates. Incubations of cells with the test compounds lasted for 72 hours at 37° C., in 5% CO$_2$ atmosphere and 100% humidity. At the end of incubation period, the cells were assayed by using the Calcein AM. Ten microliters of the stock solution were pipetted into each well and incubated further for 1 hours. Fluorescence (FD) was measured with the Labsystem FIA Reader Fluoroscan Ascent (UK). The tumour cell survival (GI$_{50}$) was calculated using the following equitation: GI$_{50}$= (FD$_{drug\ exposed\ well}$/mean FD$_{control\ wells}$)×100%. The GI$_{50}$ value, the drug concentration lethal to 50% of the tumour cells, was calculated from the obtained dose response curves (FIG. 3).

Cytoxicity of novel compounds was tested on panel of cell lines of different histogenetic and species origin (Table 8). We show here that equal activities were found in all tumour cell lines tested, however, the non-malignant cells, e.g. NIH3T3 fibroblasts and normal human lymphocytes, were resistant to synthetic inhibitors induced cytotoxicity. As demonstrated in Table 7, GI$_{50}$ for NIH3T3 fibroblasts and normal human lymphocytes was always higher than 166.7 µM. Effective novel derivatives killed tumour cells in concentrations close to 0.1-50 µM.

TABLE 8

Cytotoxicity of N$^6$-substituted Adenosine Derivatives for Different Cancer Cell Lines

| Substituent at N$^6$-position of adenosine | Cell line tested/IC 50 (µmol/L) | | | | | | |
|---|---|---|---|---|---|---|---|
| | HOS | K-562 | MCF7 | NIH-3T3 | G-361 | CEM | HL60 |
| adenosine | >166.7 | >166.7 | >166.7 | >166.7 | >166.7 | >166.7 | >166.7 |
| zeatin riboside | >166.7 | >166.7 | >166.7 | >166.7 | >166.7 | >166.7 | >166.7 |
| 2-hydroxybenzylamino | 2.8 | 88 | 11.4 | 43.2 | >166.7 | 0.7 | 0.42 |
| 3-hydroxybenzylamino | >166.7 | >166.7 | >166.7 | >166.7 | >166.7 | 51.9 | 23.7 |
| 4-hydroxybenzylamino | >166.7 | >166.7 | >166.7 | >166.7 | >166.7 | 39.7 | 9.5 |
| 2-methoxyxybenzylamino | 21.2 | 11.2 | >166.7 | >166.7 | >166.7 | 3.2 | 2.3 |
| 3-methoxyxybenzylamino | >166.7 | >166.7 | >166.7 | >166.7 | >166.7 | 7.6 | 4.9 |
| 4-methoxyxybenzylamino | >166.7 | >166.7 | >166.7 | >166.7 | 114.9 | >166.7 | >166.7 |
| 2-chlorobenzylamino | >166.7 | 64 | >166.7 | >166.7 | | 14.5 | 1.6 |
| 3-chlorobenzylamino | >166.7 | 30.4 | >166.7 | >166.7 | | 1.6 | 0.75 |
| 4-chlorobenzylamino | >166.7 | 16.1 | >166.7 | >166.7 | | 6.5 | 5.3 |
| 2-fluorobenzylamino | >166.7 | 33.2 | >166.7 | | | 4.6 | 3.2 |
| 3-fluorobenzylamino | >166.7 | 7 | 16.6 | >166.7 | 15.7 | 4 | 0.92 |
| 4-fluorobenzylamino | 20 | 6.4 | 14 | >166.7 | | 1.5 | 0.86 |
| 2-methylbenzylamino | >166.7 | >166.7 | >166.7 | >166.7 | | 14 | 3.3 |
| 3-methylbenzylamino | >166.7 | >166.7 | >166.7 | >166.7 | | 19.1 | 6.4 |
| 4-methylbenzylamino | >166.7 | >166.7 | >166.7 | >166.7 | | >166.7 | >166.7 |
| 2-bromobenzylamino | >166.7 | 10 | >166.7 | >166.7 | | 12.3 | 6.6 |
| 3-bromobenzylamino | >166.7 | 19.7 | >166.7 | >166.7 | | 5 | 8 |
| 4-bromobenzylamino | >166.7 | 68.2 | >166.7 | >166.7 | | 20.6 | 47.4 |
| 2,4-dimethoxyxybenzylamino | >166.7 | >166.7 | >166.7 | >166.7 | | >166.7 | 39 |
| 2-chloro-4-fluorobenzylamino | >166.7 | 11.7 | >166.7 | >166.7 | | 20.9 | 9 |
| 3-chloro-4-fluorobenzylamino | >166.7 | 4.1 | >166.7 | >166.7 | | 3.4 | 3.5 |
| 2,3-dimethoxyxybenzylamino | >166.7 | >166.7 | >166.7 | >166.7 | | >166.7 | 109 |
| 2,4-dichloroxybenzylamino | >166.7 | 85.7 | 126.9 | >166.7 | | 86.7 | 96.3 |
| 2,4-difluororoxybenzylamino | >166.7 | 7.4 | >166.7 | >166.7 | | 7.1 | 3.4 |
| 2,3,4-trifluororoxybenzylamino | >166.7 | >166.7 | >166.7 | >166.7 | | 58.2 | 13 |
| 3,4-dichloroxybenzylamino | >166.7 | 6.5 | 88.8 | >166.7 | | 3 | 1.1 |
| 3,5-difluororoxybenzylamino | >166.7 | >166.7 | >166.7 | >166.7 | | 24.5 | 9.1 |
| 3,5-dimethoxyxybenzylamino | >166.7 | >166.7 | >166.7 | >166.7 | | | 18.8 |
| 2,3,6-trifluororoxybenzylamino | >166.7 | >166.7 | >166.7 | >166.7 | | | 13 |
| 2-hydroxy-3-methoxybenzylamino | >166.7 | 19.2 | 27 | >166.7 | 148.1 | 0.3 | 0.15 |
| 3-hydroxy-4-methoxybenzylamino | >166.7 | >166.7 | >166.7 | >166.7 | | >166.7 | >166.7 |
| 2-hydroxy-5-methoxybenzylamino | >166.7 | 15.4 | 21 | >166.7 | 102.3 | 0.2 | 0.1 |
| 2-hydroxy-3-chlorobenzylamino | >166.7 | 10.7 | 15 | >166.7 | 128.5 | 0.3 | 0.1 |
| R2 = Cl, Substituent at N$^6$-position | | | | | | | |
| 2-hydroxybenzylamino | 2.5 | 75 | 10.5 | 35.1 | >166.7 | 0.56 | 0.38 |
| 3-hydroxybenzylamino | >166.7 | >166.7 | >166.7 | >166.7 | >166.7 | 47.8 | 15.9 |
| 4-hydroxybenzylamino | >166.7 | >166.7 | >166.7 | >166.7 | >166.7 | 39.7 | 9.5 |
| 2-methoxyxybenzylamino | 15.3 | 14.5 | >166.7 | >166.7 | >166.7 | 2.7 | 1.5 |

TABLE 8-continued

Cytotoxicity of N⁶-substituted Adenosine Derivatives for Different Cancer Cell Lines

| Substituent at $N^6$-position of adenosine | Cell line tested/IC 50 (µmol/L) | | | | | | |
|---|---|---|---|---|---|---|---|
| | HOS | K-562 | MCF7 | NIH-3T3 | G-361 | CEM | HL60 |
| 3-methoxyxybenzylamino | >166.7 | >166.7 | >166.7 | >166.7 | >166.7 | 6.5 | 4.1 |
| 4-methoxyxybenzylamino | >166.7 | >166.7 | >166.7 | >166.7 | 105.4 | >166.7 | >166.7 |
| 2-chlorobenzylamino | >166.7 | 61 | >166.7 | >166.7 | | 8.5 | 1.2 |
| 3-chlorobenzylamino | >166.7 | 28 | >166.7 | >166.7 | | 1.1 | 0.6 |
| 4-chlorobenzylamino | >166.7 | 15 | >166.7 | >166.7 | | 5.8 | 5.0 |
| 2-fluorobenzylamino | >166.7 | 30 | >166.7 | | | 4.2 | 2.5 |
| 3-fluorobenzylamino | >166.7 | 5.3 | 16 | >166.7 | 16 | 3 | 0.9 |
| 4-fluorobenzylamino | 19 | 5.8 | 12 | >166.7 | | 1.5 | 0.7 |
| 2-hydroxy-3-methoxybenzylamino | >166.7 | 17 | 23 | >166.7 | 140 | 0.2 | 0.1 |
| 2-hydroxy-3-chlorobenzylamino | >166.7 | 10 | 14 | >166.7 | 118 | 0.2 | 0.1 |
| R2 = $NH_2$, Substituent at $N^6$-position | | | | | | | |
| 2-methoxyxybenzylamino | 27.8 | 34.9 | >166.7 | >166.7 | >166.7 | 12.8 | 7.8 |
| 3-methoxyxybenzylamino | >166.7 | >166.7 | >166.7 | >166.7 | >166.7 | 13.8 | 8.9 |
| 2-chlorobenzylamino | >166.7 | 78 | >166.7 | >166.7 | | 24.7 | 10.3 |
| 3-chlorobenzylamino | >166.7 | 43 | >166.7 | >166.7 | | 10.2 | 5.8 |
| 2-fluorobenzylamino | >166.7 | 45 | >166.7 | | | 14.5 | 8.7 |
| 3-fluorobenzylamino | >166.7 | 12 | 36 | >166.7 | 21 | 21 | 3.4 |
| 4-fluorobenzylamino | 43 | 13 | 25 | >166.7 | | 12.1 | 2.9 |
| R2 = $SCH_3$, Substituent at $N^6$-position | | | | | | | |
| 2-methoxyxybenzylamino | 34.3 | 34.8 | >166.7 | >166.7 | >166.7 | 11.5 | 10.2 |
| 3-methoxyxybenzylamino | >166.7 | >166.7 | >166.7 | >166.7 | >166.7 | 16.5 | 8.8 |
| 2-chlorobenzylamino | >166.7 | 78 | >166.7 | >166.7 | | 14.6 | 7.4 |
| 3-chlorobenzylamino | >166.7 | 35 | >166.7 | >166.7 | | 13.2 | 6.1 |
| 2-fluorobenzylamino | >166.7 | 42 | >166.7 | | | 9.7 | 11.4 |
| 3-fluorobenzylamino | >166.7 | 7.9 | 31 | >166.7 | 28 | 8.5 | 5.2 |

Example 10

Novel Compounds Induce Apoptosis in Tumour Cells

To analyse the mechanisms of induced cytotoxicity by the novel compounds, it is important to distinguish apoptosis from the other major form of cell death, necrosis. First, at the tissue level, apoptosis produces little or no inflammation, since the neighbouring cells, especially macrophages, rather than being released into the extracellular fluid, engulf shrunken portions of the cell. In contrast, in necrosis, cellular contents are released into the extracellular fluid, and thus have an irritant affect on the nearby cells, causing inflammation. Second, at the cellular level, apoptotic cells exhibit shrinkage and blebbing of the cytoplasm, preservation of structure of cellular organelles including the mitochondria, condensation and margination of chromatin, fragmentation of nuclei, and formation of apoptotic bodies, thought not all of these are seen in all cell types. Third, at the molecular level, a number of biochemical processes take an important role in induction of apoptosis. However, majority of them is not well understood, and they result in activation of proteases and nucleases, which finally destruct key biological macromolecules—proteins and DNA.

Cell culture. A suspension of human promyelocytic HL-60 cells was cultured in RPMI-1640 medium supplemented with a 10% calf foetal serum and antibiotics in 5% $CO_2$ atmosphere at 37° C. Cells were maintained at density from $1\times10^5$ to $6\times10^5$ cells per ml. HL-60 cells were obtained from ECACC.

Cell viability assay. Double staining with fluorescein diacetate (FDA) and propidium iodide (PI) for discrimination of dead and living cells was used. Cells were stained in growing medium with PI at a concentration 10 µg/ml 5 min later FDA was added at a concentration 1 µg/ml. The percentage of dead cells (i.e., red stained cells) was evaluated using fluorescence microscopy (Mlejnek and Kolman 1999).

Morphological analysis of cell nuclei. Cells were harvested, washed in PBS, and fixed in an ice-cold methanol+acetic acid (3:1) fixation mixture. Aliquots of cells were spread on glass slides and stained with Hoechst 33342 (2 µg/ml) in PBS. The morphology of cell nuclei was examined by a fluorescence microscope (Mlejnek and Kuglik 2000).

Cell cycle analysis. Cells were washed in PBS and then fixed in 70% ethanol at −20° C. over night. Fixed cells are washed in PBS and stained in PBS containing PI (20 µg/ml) and RNase A (100 µg/ml) for 30 min at 37° C. prior to FACScan analysis (Mlejnek and Kolman 1999).

DNA fragmentation assay. Aliquots of cells were washed in PBS and lysed by addition of DNA lysis buffer (50 mM Tris/HCl, pH=8.0, 10 mM EDTA, 0.5% sodium lauroyl sarcosine, and 0.5 mg/ml proteinase K) at 37° C. overnight. Samples were treated further with DNase-free RNase-A (0.2 mg/ml) at 37° C. for 3 h. The resulting extracts were loaded onto 1.8% agarose gel containing ethidium bromide (Mlejnek and Kuglik 2000).

HPLC analysis of acidic cellular extracts. Approximately $10^7$ cells were washed in PBS and harvested by centrifugation. Cell pellet were extracted with ice cold 0.5M $HClO_4$ for 20 at 0° C. Precipitate and debris were removed by centrifugation (18 000×g for 10 min at 2° C.). Acidic extracts were neutralized by addition of 2.5 M $K_2CO_3$ and the insoluble material was removed by centrifugation. Cell extracts were loaded onto a µBONDAPAC $C_{18}$ reversed-phase column (4.0×250 mm, 5 µm particle size) and the mobile phase was eluted under isocratic conditions (100 mM $NaH_2PO_4$, pH=6.4, 5 mM tetrabutylamonium phosphate +10% acetonitril/water at a flow rate 400 µl min⁻¹. Quantitative analysis was done using external standards of ATP, iPA, and iPA-monophosphate.

Caspase protease activity measurement. Cells were washed in PBS and then extracted in buffer [50 mM HEPES, pH 7.4, 1 mM EDTA, 0.1% Chaps, 5 mM DTT, and proteinase inhibitor cocktail (Roche)] on ice. Cell extracts were centrifuged for 30 min at 30 000×g at 4° C. Clarified extract were immediately analysed or stored at –80° C. Measurement of proteolytic activity was done using synthetic fluorogenic substrates Ac-DEVD-AMC and Ac-LEHD-AMC for caspase-3 and -9, respectively. The assay was carried out in 1 ml tubes, aliquots of lysates (200-300 µg of total protein) were mixed with 1 ml of buffer (25 mM PIPES/KOH, 2 mM EGTA, 5 mM DTT, and 0.1% Chaps, pH 7.3) and reactions were initiated by adding 50 µM substrate. Samples were incubated for 1 hour at 30° C. before the fluorescence was determined. Excitation and emission wavelengths were the same for both substrates (380 nm and 445 nm, respectively).

Results 6-(2-hydroxy-3-methoxybenzyl)amino-purine riboside (2OH3MeOBAPR) and other related cytokinin derivatives inhibit cell proliferation (FIG. 4) a induce HL-60 cell death, with typical morphological and biochemical characteristics of apoptosis (FIG. 5-7). Cell cycle analysis shows, that 2OH3MeOBAPR does not inhibit cell cycle in certain control point(s), but rather unspecifically (FIG. 8). 2OH3MeOBAPR application activate caspase proteases, especially caspase-9 and -3 (FIG. 9). It is not possible to stop cell death by inhibition of caspase proteases. Unspecific caspase inhibitor Z-VAD-FMK suppress morphological and biochemical characteristics of apoptosis, however it does not inhibit cell death itself (FIG. 10). 2OH3MeOBAPR is not cell cytotoxic by itself, this is attribute of its phosphorylated forms only. Adenosine kinase inhibitors, which block intracellular 2OH3MeOBAPR conversion to its monophosphate, totally stop apoptosis induction including all their morphological and biochemical attributes (FIG. 11).

Example 11

Immunosuppressive Activity

One of the most important parameters of specific cellular immunity is proliferative response of lymphocytes to antigens or polyclonal mitogens. The majority of normal mammalian peripheral lymphocytes comprise resting cells. Antigens or nonspecific polyclonal mitogens have the capacity to activate lymphoid cells and this is accompanied by dramatic changes of intracellular metabolism (mitochondrial activity, protein synthesis, nucleic acids synthesis, formation of blastic cells and cellular proliferation). Compounds with ability to selectively inhibit lymphocyte proliferation are potent immunosuppressants. Variety of in vitro assays was developed to measure proliferative response of lymphocytes. The most commonly used is ³H-thymidine incorporation method.

During cell proliferation, DNA has to be replicated before the cell is divided into two daughter cells. This close association between cell doublings and DNA synthesis is very attractive for assessing cell proliferation. If labelled DNA precursors are added to the cell culture, cells that are about to divide incorporate the labelled nucleotide into their DNA. Traditionally, those assays usually involve the use of radiolabelled nucleosides, particularly tritiated thymidine ([³H]-TdR). The amount of [³H]-TdR incorporated into the cellular DNA is quantified by liquid scintillation counting.

Human heparinized peripheral blood was obtained from healthy volunteers by cubital vein punction. The blood was diluted in PBS (1:3) and mononuclear cells were separated by centrifugation in Ficoll-Hypaque density gradient (Pharmacia, 1.077 g/ml) at 2200 rpm for 30 minutes. Following centrifugation, lymphocytes were washed in PBS and resuspended in cell culture medium (RMPI 1640, 2 mM glutamine, 100 U/ml penicillin, 100 µg/ml streptomycin, 10% fetal calf serum and sodium bicarbonate).

The cells were diluted at target density of 1,100,000 cells/ml were added by pipette (180 µl) into 96/well microtiter plates. Four-fold dilutions of the intended test concentration were added at time zero in 20 µl aliquots to the microtiter plate wells. Usually, test compound was evaluated at six 4-fold dilutions. In routine testing, the highest well concentration was 266.7 µM. All drug concentrations were examined in duplicates. All wells with exception of unstimulated controls were activated with 50 µl of concanavalin A (25 µg/ml). Incubations of cells with test compounds lasted for 72 hours at 37° C., in 5% $CO_2$ atmosphere and 100% humidity. At the end of incubation period, the cells were assayed by using the [³H]-TdR:

Cell cultures were incubated with 0.5 µCi (20 µl of stock solution 500 µCi/ml) per well for 6 hours at 37° C. and 5% $CO_2$. The automated cell harvester was used to lyse cells in water and adsorb the DNA onto glass-fiber filters in the format of microtiter plate. The DNA incorporated [³H]-TdR was retained on the filter while unincorporated material passes through. The filters were dried at room temperature overnight, sealed into a sample bag with 10-12 ml of scintillant. The amount of [³H]-TdR present in each filter (in cpm) was determined by scintillation counting in a Betaplate liquid scintillation counter. The effective dose of immunosuppressant (ED) was calculated using the following equation: ED=(CCPM$_{drug\ exposed\ well}$/mean CCPM$_{control\ wells}$)×100%. The ED$_{50}$ value, the drug concentration inhibiting proliferation of 50% of lymphocytes, was calculated from the obtained dose response curves.

To evaluate immunosuppressive activity of substituted adenines, their ability to inhibit polyclonal mitogen induced proliferation of normal human lymphocytes was analyzed (Tab. 9). Our data demonstrate that these compounds have only marginal activity on ³H-thymidine incorporation, nonetheless, they efficiently inhibit proliferation of activated lymphocytes. Effective immunosuppressive dose of new derivatives under in vitro conditions was close to 1-20 µM.

TABLE 9

Immunosupressive activity of novel derivatives

| SUBSTITUENT AT N⁶-POSITION OF ADENOSINE | Human lymphocytes ED$_{50}$ (µM) |
|---|---|
| 2-hydroxybenzylamino | 4.8 |
| 3-hydroxybenzylamino | 10.7 |
| 2-fluorobenzylamino | 5.6 |
| 3-fluorobenzylamino | 7.1 |
| 4-fluorobenzylamino | 9.4 |
| 2-methylbenzylamino | 5.8 |
| 3-methylbenzylamino | 6.5 |
| 3,4-dihydroxybenzylamino | 8.3 |
| 2-hydroxy-3-chlorobenzylamino | 2.1 |
| 2-hydroxy-3-methoxybenzylamino | 1.4 |
| 2-hydroxy-4-methoxybenzylamino | 1.5 |
| 2-chlorobenzylamino | 8.4 |
| 3-chlorobenzylamino | 2.5 |
| 4-chlorobenzylamino | 3.9 |

Example 12

Senescence Inhibition by Novel Compounds Tested on Winter Wheat Leaf Segments Seeds of winter wheat, *Triticum aestivum* cv. Hereward, were washed under running water for 24 hours and then sown on vermiculite soaked with Knop's solution. They were placed in the grown chamber at 15° C. with a 16/8 h light period at 50 µmol·m$^{-2}$·s$^{-1}$. After 7 days, the first leaf was fully developed and the second leaf had started to grow. A tip section of the first leaf, approximately 35 mm long, was removed from 5 seedlings and trimmed slightly to a combined weight of 100 mg. The basal ends of the five leaf tips were placed in the wells of a microtiter polystyrene plate containing 150 µl of a cytokinin solution each. The entire plate was inserted into a plastic box lined with paper tissues soaked in distilled water to prevent leaf sections from drying out. After a 96 h incubation in the dark at 25° C., the leaves were removed and chlorophyll extracted by heating at 80° C. for 10 min in 5 ml of 80% ethanol (v/v). The sample volume was then restored to 5 ml by the addition of 80% ethanol (v/v). The absorbency of the extract was recorded at 665 nm. In addition, chlorophyll extracts from fresh leaves and leaf tips incubated in deionised water were measured. From the obtained data, the concentration with highest activity was selected for each compound tested. Relative activity of the compound at this concentration was calculated (Tab. 10). The activity obtained for 10$^{-4}$ M 6-benzylaminopurine (BAP) was postulated as 100%. The values shown are means of five replicates and the whole experiment was repeated twice. The cytokinins to be tested were dissolved in dimethylsulfoxide (DMSO) and the solution brought up to 10$^{-3}$M with distilled water. This stock was further diluted in distilled water to concentrations ranging from 10$^{-8}$M to 10$^{-4}$M. The final concentration of DMSO did not exceed 0.2% and therefore did not affect biological activity in the assay system used.

TABLE 10

Effect of new cytokinin derivatives on retention of chlorophyll in excised wheat leaf tips.

| Substituent N6 | Concentration with highest activity (mol·l$^{-1}$) | Activity (%) [10$^{-4}$ mol·l$^{-1}$ BAP = 100%] |
|---|---|---|
| 2-fluorobenzylamino | 10$^{-4}$ | 118 ± 19 |
| 3-fluorobenzylamino | 10$^{-4}$ | 220 ± 16 |
| 4-fluorobenzylamino | 10$^{-4}$ | 148 ± 2 |
| 2-chlorobenzylamino | 10$^{-4}$ | 119 ± 9 |
| 3-chlorobenzylamino | 10$^{-4}$ | 72 ± 8 |
| 4-chlorobenzylamino | 10$^{-4}$ | 104 ± 6 |
| 2-bromobenzylamino | 10$^{-5}$ | 86 ± 19 |
| 3-bromobenzylamino | 10$^{-4}$ | 89 ± 10 |
| 4-bromobenzylamino | 10$^{-4}$ | 76 ± 11 |
| 3-jodobenzylamino | 10$^{-4}$ | 98 ± 4 |
| 2-methylbenzylamino | 10$^{-4}$ | 142 ± 6 |
| 3-methylbenzylamino | 10$^{-4}$ | 143 ± 9 |
| 4-methylbenzylamino | 10$^{-4}$ | 55 ± 5 |
| 2-methoxylbenzylamino | 10$^{-4}$ | 198 ± 12 |
| 3-methoxylbenzylamino | 10$^{-4}$ | 209 ± 8 |
| 4-methoxylbenzylamino | 10$^{-4}$ | 110 ± 9 |
| 2,4-dichlorobenzylamino | 10$^{-5}$ | 5 ± 1 |
| 3,4-dichlorobenzylamino | 10$^{-4}$ | 151 ± 29 |
| 2,3-dimethoxybenzylamino | 10$^{-4}$ | 106 ± 17 |
| 3,4-dimethoxylbenzylamino | 10$^{-4}$ | 47 ± 6 |
| 3-chloro-4-fluorobenzylamino | 10$^{-4}$ | 156 ± 10 |
| 3,5-difluorobenzylamino | 10$^{-4}$ | 195 ± 14 |
| 2,4-difluorobenzylamino | 10$^{-4}$ | 171 ± 8 |
| 2,3,4-trifluorobenzylamino | 10$^{-4}$ | 144 ± 12 |
| 2,3,6-trifluorobenzylamino | 10$^{-4}$ | 133 ± 14 |
| 2-hydroxy-3-methoxylbenzylamino | 10$^{-4}$ | 30 ± 8 |
| 3-hydroxy-4-methoxylbenzylamino | 10$^{-4}$ | 22 ± 5 |

The developed compounds exhibit very strong antisenescent activities. Some of the compounds induce almost 200% increase in the chlorophyll content in the decapitated wheat leaves in comparison to the control.

Example 13

Stimulation Effect of the New Compounds on Plant Cell Division

Cytokinin-dependent tobacco callus *Nicotiana tabacum* L. cv. Wisconsin 38 was maintained at 25° C. in darkness on modified Murashige-Skoog medium, containing per 1 liter: 4 µmol nicotinic acid, 2.4 µmol pyridoxine hydrochloride, 1.2 µmol thiamine, 26.6 µmol glycine, 1.37 µmol glutamine, 1.8 µmol myo-inositol, 30 g of sucrose, 8 g of agar, 5.37 µmol α-naphtylacetic acid (NAA) and 0.5 µmol benzylaminopurine (BAP). Subcultivation was carried out every three weeks. Fourteen days before the bioassay, the callus tissue was transferred to the media without 6-benzylaminopurine (BAP). Biological activity was determined from the increase in fresh callus weight after four weeks of cultivation. Five replicates were prepared for each cytokinin concentration and the entire test was repeated twice. From the obtained data, the concentration with highest activity was selected for each compound tested. Relative activity of the compound at this concentration was calculated (Tab. 6). The activity obtained for 10$^{-4}$ M 6-benzylaminopurine (BAP) was postulated as 100%. The cytokinins to be tested were dissolved in dimethylsulfoxide (DMSO) and the solution brought up to 10$^{-3}$M with distilled water. This stock was further diluted in the respective media used for the biotest to concentrations ranging from 10$^{-8}$M to 10$^{-4}$M. The final concentration of DMSO did not exceed 0.2% and therefore did not affect biological activity in the assay system used.

TABLE 11

The effect of new cytokinin derivatives on growth of cytokinin-dependent tobacco callus *Nicotiana tabacum* L. cv. Wisconsins 38

| Substituent N6 | Concentration with highest activity (mol·l$^{-1}$) | Activity (%) [10$^{-5}$ mol·l$^{-1}$ BAP = 100%] |
|---|---|---|
| 2-fluorobenzylamino | 10$^{-6}$ | 100 ± 9 |
| 3-fluorobenzylamino | 10$^{-5}$ | 91 ± 6 |
| 4-fluorobenzylamino | 10$^{-6}$ | 100 ± 6 |
| 2-chlorobenzylamino | 10$^{-6}$ | 93 ± 4 |
| 3-chlorobenzylamino | 10$^{-5}$ | 96 ± 5 |
| 4-chlorobenzylamino | 10$^{-6}$ | 46 ± 14 |
| 2-bromobenzylamino | 10$^{-5}$ | 100 ± 4 |
| 3-bromobenzylamino | 10$^{-6}$ | 82 ± 11 |
| 4-bromobenzylamino | 10$^{-6}$ | 15 ± 11 |
| 3-jodobenzylamino | 10$^{-6}$ | 47 ± 12 |
| 2-methylbenzylamino | 10$^{-6}$ | 98 ± 4 |
| 3-methylbenzylamino | 10$^{-6}$ | 90 ± 2 |

TABLE 11-continued

The effect of new cytokinin derivatives on growth of cytokinin-dependent tobacco callus Nicotiana tabacum L. cv. Wisconsins 38

| Substituent N6 | Concentration with highest activity (mol · l$^{-1}$) | Activity (%) [10$^{-5}$ mol · l$^{-1}$ BAP = 100%] |
|---|---|---|
| 4-methylbenzylamino | 10$^{-6}$ | 95 ± 6 |
| 2-methoxylbenzylamino | 10$^{-5}$ | 108 ± 1 |
| 3-methoxylbenzylamino | 10$^{-6}$ | 92 ± 1 |
| 4-methoxylbenzylamino | 10$^{-6}$ | 2 ± 2 |
| 2,3-dimethoxybenzylamino | 10$^{-6}$ | 5 ± 2 |
| 3-chloro-4-fluorobenzylamino | 10$^{-6}$ | 87 ± 4 |
| 2-chloro-4-fluorobenzylamino | 10$^{-5}$ | 98 ± 4 |
| 3,5-difluorobenzylamino | 10$^{-6}$ | 95 ± 3 |
| 2,3,6-trifluorobenzylamino | 10$^{-5}$ | 92 ± 2 |
| 2,4,5-trifluorobenzylamino | 10$^{-5}$ | 95 ± 3 |

Example 14

Testing of Novel Compounds in *Amaranthus* Bioassay

Standard *Amaranthus* bioassay was performed with several modifications. The seeds of *Amaranthus caudatus* var. *atropurpurea* were surface-sterilised in 10% N-chlorobenzenesulfonamide (w/v) for 10 min and washed 5 times in deionized water. They were placed in 15 cm Petri dishes containing paper tissues saturated with deionized water. After 72 h of cultivation at 25° C. in darkness, the roots of the seedlings were cut off. The explants, consisting of two cotyledons and hypocotyls, were placed in 5 cm Petri dishes on two layers of filter paper soaked in 1 ml of incubation medium containing 10 μmol NA$_2$HPO$_4$—KH$_2$PO$_4$, pH 6.8, 5 μmol tyrosine and the cytokinin to be tested. There were 20 explants per dish. The procedure was carried out under a green safe light in a darkroom. After a 48 h of incubation at 25° C. in darkness, betacyanin was extracted by freezing the explants in 4 ml 3.33 μM acetic acid. The concentration of betacyanin was determined by comparing the absorbance at 537 nm and 620 nm as follows: $\Delta A = A_{537nm} - A_{620nm}$. From the obtained data, the concentration with highest activity was selected for each compound tested. Relative activity of the compound at this concentration was calculated (Tab. 12). The activity obtained for 10$^{-4}$ M 6-benzylaminopurine (BAP) was postulated as 100%. The values shown in table 8 are means of five replicates and the entire test was repeated twice.

The cytokinins to be tested were dissolved in dimethylsulfoxide (DMSO) and the solution brought up to 10$^{-3}$M with distilled water. This stock was further diluted in the respective media used for the biotest to concentrations ranging from 10$^{-8}$M to 10$^{-4}$M. The final concentration of DMSO did not exceed 0.2% and therefore did not affect biological activity in the assay system used.

From the data obtained (FIG. 14) the maximum effective concentration of the tested compound was calculated as well as its relative effectiveness at this concentration (Table 12). The concentration 10$^{-4}$ M BAP was postulated asd 100% biological activity.

TABLE 12

The effect of new cytokinin derivatives on betacyanin content in *Amaranthus caudatus* cotyledon/hypocotyl explants.

| Substituent N6 | Concentration with highest activity (mol · l$^{-1}$) | Activity (%) [10$^{-5}$ mol · l$^{-1}$ BAP = 100%] |
|---|---|---|
| 1. 2-fluorbenzylamino | 10$^{-4}$ | 96 ± 2 |
| 2. 3-fluorbenzylamino | 10$^{-4}$ | 92 ± 6 |
| 3. 4-fluorbenzylamino | 10$^{-5}$ | 71 ± 4 |
| 4. 2-chlorbenzylamino | 10$^{-5}$ | 113 ± 7 |
| 5. 3-chlorbenzylamino | 10$^{-5}$ | 139 ± 12 |
| 6. 4-chlorbenzylamino | 10$^{-5}$ | 35 ± 9 |
| 7. 2-brombenzylamino | 10$^{-4}$ | 147 ± 7 |
| 8. 3-brombenzylamino | 10$^{-4}$ | 151 ± 16 |
| 9. 4-brombenzylamino | 10$^{-5}$ | 30 ± 8 |
| 10. 3-jodbenzylamino | 10$^{-5}$ | 102 ± 18 |
| 11. 2-methylbenzylamino | 10$^{-5}$ | 105 ± 14 |
| 12. 3-methylbenzylamino | 10$^{-5}$ | 103 ± 16 |
| 13. 4-methylbenzylamino | 10$^{-5}$ | 32 ± 7 |
| 14. 2-methoxybenzylamino | 10$^{-5}$ | 86 ± 4 |
| 15. 3-methoxybenzylamino | 10$^{-4}$ | 98 ± 10 |
| 16. 4-methoxybenzylamino | 10$^{-4}$ | 17 ± 8 |
| 17. 3-nitrobenzylamino | 10$^{-4}$ | 66 ± 7 |
| 18. 4-nitrobenzylamino | 10$^{-4}$ | 25 ± 3 |
| 19. 2,4-dichlorbenzylamino | 10$^{-4}$ | 3 ± 2 |
| 20. 3,4-dichlorbenzylamino | 10$^{-4}$ | 68 ± 10 |
| 21. 2,3-dimethoxybenzylamino | 10$^{-4}$ | 21 ± 7 |
| 22. 2,4-dimethoxybenzylamino | 10$^{-5}$ | 3 ± 3 |
| 23. 3,4-dimethoxybenzylamino | 10$^{-4}$ | 2 ± 1 |
| 24. 3,4-dihydroxybenzylamino | 10$^{-4}$ | 8 ± 3 |
| 25. 2,4-difluorobenzylamino | 10$^{-4}$ | 88 ± 7 |
| 26. 3,5-difluorobenzylamino | 10$^{-4}$ | 88 ± 1 |
| 27. 2,3,6-trifluorobenzylamino | 10$^{-4}$ | 94 ± 1 |
| 28. 3-chloro-4-fluorobenzylamino | 10$^{-4}$ | 82 ± 5 |
| 29. 2-hydroxy-3-methoxybenzylamino | 10$^{-4}$ | 18 ± 5 |
| 30. 3-hydroxy-4-methoxybenzylamino | 10$^{-4}$ | 0 |
| 31. 2-chloro-4-fluorobenzylamino | 10$^{-4}$ | 115 ± 1 |
| 32. 2,4,5-trifluorobenzylamino | 10$^{-4}$ | 120 ± 1 |

Example 15

The Effect of New Derivatives on In Vitro and Post Vitro Multiplication and Rooting of Rose (*Rosa multiflora*)

The aim of this experiment was to test whether the new compounds are of practical use in tissue culture practice. The multiplication rate was investigated and the post vitro effects on rooting were examined. *Rosa hybrida* (pot rose cultivar) was cultured in 350 ml vessels with a screw on polycarbonate lid. Each culture vessel contained 100 ml autoclaved medium (120° C., 20 min). The cultures were maintained at 23±2° C. under a 16 h photoperiod at 40 μM m$^{-2}$ s$^{-1}$ PAR. The basal medium (MBR) contained Murashige and Skoog (1962) macroelements, microelements and vitamins, 95 μM NaFeEDTA, 555 μM myo-inositol, 111 mM sucrose, 1.332 mM glycine, 684 μM L-glutamine and 7 g/l agar. This medium was supplemented with 10 μM of the tested compound. 6-Benzylaminopurine (BAP) was used as a standard compound; the control medium didn't contain any cytokinin. After a culture period of 8 weeks, the number of induced shoots per explant was determined, as well as root number/explant and total root length/explant. The roots were removed and the explants (shoot clusters) were planted in unfertilised peat. After four weeks of acclimatising in a fog unit, root number and root length was determined.

As expected, a cytokinin free medium yielded almost no new shoots. The original shoot explant grew out as a good quality single shoot that rooted very well (Table 13). BAP gave a high shoot multiplication rate, but the shoots rooted badly (Table 13). The new BAP derivatives tested, induced formation of new shoots and rooting significantly better, when compared with BAP itself (Table 13).

TABLE 13

Effects of cytokinins on in vitro and post vitro shoot multiplication and rooting in *Rosa multiflora*

| | In vitro | | | | Ex vitro | |
|---|---|---|---|---|---|---|
| Substituent | Number of new shoots per explant | Flower number per explant | Root number per explant | Total root length per explant (cm) | Root number per plant | Total root length per plant (cm) |
| Control | 0.2 | 0.03 | 0.8 | 1.2 | 4.6 | 17.1 |
| BAP* | 3.8 | 0.00 | 0.0 | 0.0 | 0.6 | 1.1 |
| 2-methoxybenzylamino | 1.4 | 0.17 | 0.0 | 0.0 | 1.6 | 4.8 |
| 3-methoxybenzylamino | 5.6 | 0.00 | 0.0 | 0.0 | 1.4 | 3.5 |

*BAP = 6-benzylaminopurine

Example 16

Early Shoot Senescence Inhibition of Tissue Cultured Roses (*Rosa hybrida*)

Tissue cultured roses suffer from senescence symptoms. The leafs start to turn brown and after some weeks all explants in a vessel die off. The symptoms start earlier when the aeration of the vessel is inhibited, for instance by a plastic foil. This suggests that ethylene our other gaseous components are involved. The cytokinins which are applied to the medium, induce ethylene, so it looked worthwhile to test the promising new cytokinin compounds on this system.

*Rosa hybrida* 'Pailin' (a cut rose) was cultured in 350 ml vessels with a screw on polycarbonate lid. Each culture vessel contained 100 ml autoclaved medium (120° C., 20 min). The cultures were maintained at 23±2° C. under a 16 h photoperiod at 40 µM m$^{-2}$ s$^{-1}$ PAR. The basal medium (MBR) contained Murashige and Skoog (1962) macroelements, microelements and vitamins, 36.7 mg/l NaFeEDTA, 50 mg/l NaFeEDDHA, 100 mg/l µM myo-inositol, 30 g/l sucrose, 100 mg/l glycine, 50 mg/l calcium pantothenate, 100 mg/l L-glutamine and 7 g/l agar-agar. This medium was supplemented with 10 µM of the tested cytokinin. New cytokinins were filter sterilised and added after autoclaving the medium in the vessels. 6-Benzylaminopurine (BAP) was used as a standard compound; the control medium didn't contain any cytokinin. After a culture period of 6 weeks, scoring senescence symptoms was started. The day on which the first brown leaf appeared was noted for each plant (FIG. 17), as well as the day of complete dying of the whole explant (FIG. 15, 16).

On medium with BAP, the relative number of dead plants looks like a sigmoid curve, suggesting an autocatalytic senescence effect, may be caused by ethylene. It would be interesting to measure the ethylene concentration in the headspace. On 6-(3-hydroxybenzylamino)purine (mT) and 6-(3-methoxyxybenzylamino)purine riboside (3MeOBAPR) the situation improved. 3MeOBAPR was definitely the best compound. Even after 121 days almost all plants were still alive. Although some brown leaves could not be avoided on a medium with 3MeOBAPR, these plants could be easily used for a next subculture. The use of 3MeOBAPR is a significant improvement in the micropropagation of *Rosa hybrida*.

Example 17

Field Studies

Application of New Cytokinin Derivatives to a Spring Wheat Crop

Crops (over the 4-year period) of spring wheat were sown in the experimental fields of Czech Agriculture University (ČZU) (region of sugar beet production type) at a seeding rate of 400 germinative grains·m$^{-2}$ into ploughed and shoddy soil containing 116.1 mg/kg P, 228.3 mg/kg K, and 211.8 mg/kg Mg (agrochemical analyses were done at Department of Pedology ČZU) (interval between ploughing and sowing is usually 3-4 days, longer only in case of adverse weather conditions). Preceding crop was rape. Soil preparation was done by the classical way using skid and harrow and after seeding is rolled. Characteristics of the experimental years, average temperature and precipitation per month are given in table 13.

FIG. 13. Characteristics of the experimental years-average temperature and precipitation per month in the experimental field area

| | year | | | | | | | | | |
|---|---|---|---|---|---|---|---|---|---|---|
| | 1997 | | 1998 | | 1999 | | 2000 | | 2001 | |
| | temperature | rainfall | temperature | rainfall | temperature | rainfall | temperature | rainfall | temperature | rainfall |
| January | −3.2 | 20.3 | 2.2 | 8.37 | 0.64 | 8.7 | −1.5 | 22 | 1.8 | 22.3 |
| February | 3.3 | 18.7 | 5 | 12.8 | 3.47 | 18.9 | 3.1 | 22 | −2.3 | 31.9 |
| March | 6.8 | 23.7 | 5.4 | 18.4 | 3.24 | 30.6 | 3.9 | 26 | 3.2 | 11.9 |
| April | 9.7 | 29.3 | 4.6 | 15 | 9.88 | 11.7 | 10.5 | 41 | 10.6 | 16.5 |
| May | 8.7 | 15.2 | 11.4 | 5.2 | 13.6 | 25.4 | 15.4 | 54 | 16.3 | 66.1 |
| June | 12.3 | 70.5 | 15.4 | 37 | 16.7 | 101.2 | 17.5 | 63 | 16.6 | 97.7 |
| July | 17.1 | 108.9 | 18.5 | 79.8 | 17.4 | 67.4 | 15.8 | 69 | 17.1 | 102.3 |
| August | 18.7 | 60.5 | 19.7 | 58.4 | 17.8 | 22.5 | 18.8 | 64 | 17.6 | 56.7 |
| September | 13 | 41.5 | 13.8 | 67.1 | 15.2 | 68.8 | 13.7 | 42 | 11.5 | 68 |
| October | 6.5 | 34.1 | 9.6 | 37.4 | 8.54 | 86.4 | 10.6 | 35 | 8.3 | 48.6 |

FIG. 13. Characteristics of the experimental years-average temperature and precipitation per month in the experimental field area

| | \multicolumn{10}{c}{year} |
|---|---|---|---|---|---|---|---|---|---|---|
| | \multicolumn{2}{c}{1997} | \multicolumn{2}{c}{1998} | \multicolumn{2}{c}{1999} | \multicolumn{2}{c}{2000} | \multicolumn{2}{c}{2001} |
| | temperature | rainfall | temperature | rainfall | temperature | rainfall | temperature | rainfall | temperature | rainfall |
| November | 2.7 | 28.2 | 5.7 | 41.2 | 0.54 | 23.4 | 2.5 | 29 | 1 | 50.2 |
| December | 1.2 | 46.1 | 2.4 | 27.8 | −0.55 | 8.1 | 0.4 | 26 | 3.6 | 33.9 |
| average | 8.07 | | 9.5 | | 8.9 | | 9.2 | | 8.8 | |
| total | | 497 | | 408.47 | | 473.1 | | 471 | | 606.1 |
| | \multicolumn{10}{c}{Weather characteristics in growing season} |
| April | 9.7 | 29.3 | 4.6 | 15 | 9.88 | 11.7 | 10.5 | 41 | 10.6 | 16.5 |
| May | 8.7 | 15.2 | 11.4 | 5.2 | 13.6 | 25.4 | 15.4 | 54 | 16.3 | 66.1 |
| June | 12.3 | 70.5 | 15.4 | 37 | 16.7 | 101.2 | 17.5 | 63 | 16.6 | 97.7 |
| July | 17.1 | 108.9 | 18.5 | 79.8 | 17.4 | 67.4 | 15.8 | 69 | 17.1 | 102.3 |
| average | 12 | | 12.5 | | 14.4 | | 14.8 | | 8.8 | |
| total | | 223.9 | | 137 | | 205.7 | | 227 | | 282.6 |

Height of plants, leaf area, dry matter, development of vegetation opex—bases of future spike, and number of spikelets were monitored after germination in 14 day intervals, po ošetřeni i obsah chlorofylu v listech. From these primary data, values used in production physiology are derived, as leaf area index LAI, photosynthetic capacity LAD, tillering potential. Experiments with treatment of spring wheat crop (variety Sandra) are carried out on the field (area 10 m², four replicates) by spraying 1 litr of $10^{-6}$ molar solution of tested compound (cytokinin) at the transition period from jointing stage to athesis stage (49 DC).

Glutamate kinase activity was determined 6 days after the application. This enzyme was selected because of good corelation of its activity changes and state of transport of endogenous substances (nutrients from roots, assimilates to cariopsis), respiration, energy (adenosintriphosphate) transfer, storage of nutrients, growth and developmental proceses, and also metabolism of proline, which is known from literature to play an important role in adaptation against stress (unsuitable stand, drought, hypersalinity, coldness) and also in regulation of both theoretical and real production (restriction of seed number reduction per spikelet). Enzyme glutamate kinase catalyses to glutamate conversion into γ glutamylphosphate, which is first step of proline biosynthesis from glutamate. Therefore, this enzyme is, as essential precursor of other plant metabolic pathways, marker of stress inhibition. It can be determined spectrofotometrically (Vašáková, 1980). For analysis, acetone powder is prepared from a sample by standard method, subsequently extracted by 0.05M potassium-phosphate buffer pH=7.2 and centrifugated. Glutamate kinase fraction is precipitated using crystalline ammonium sulfate and after dialysis, glutamate kinase activity is determined spectrophotometrically. Proline accumulation increased by stress corresponds as a "feedback" to glutamate kinase inhibition.

Yield analysis, evaluating spike lenght and seed number per spikelet (Σ Z/K) were carried out for 30 plant per each variant, yield from 1 m² and 1000 grain weight (HTS) was determined from 8 replicates, yield per ha was subsequently calculated.

TABLE 14

Yield analysis and glutamate kinase activity (GK) after treatment by new cytokinin derivatives (BAP - 6-benzylaminopurine, BAPR - 6-benzylaminopurine riboside, 3ClBAPR - 6-(3-chlorobenzylamino)purine riboside, 3BrBAPR - 6-(3-bromobenzylamino)purine riboside, 3,4ClBAPR - 6-(3,4-dichlorobenzylamino)purine riboside)

| | HTS (%) | Σ spike/m² (%) | Yield(%) | Σ Z/K (%) | GK % |
|---|---|---|---|---|---|
| Control | 100.0 | 100.0 | 100.0 | 100.0 | 100.0 |
| BAP | 102.0 | 101.1 | 115.4 | 111.9 | 108.2 |
| BAPR | 103.8 | 102.7 | 121.9 | 114.3 | 154.1 |
| 3ClBAPR | 108.3 | 100.5 | 128.8 | 119.1 | 124.7 |
| 3Br BAPR | 101.5 | 104.9 | 131.8 | 123.8 | 116.6 |
| 3,4 Cl BAPR | 101.5 | 99.7 | 113.3 | 111.9 | 114.2 |

Example 18

Dry Capsules 5000 capsules, each of which contains 0.25 g of one of the compounds of the formula I, II and III mentioned in the preceding or following Examples as active ingredient, are prepared as follows:

| Composition | |
|---|---|
| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 19

Soft Capsules 5000 soft gelatine capsules, each of which contains 0.05 g of one of the compounds of the formula I, II and III mentioned in the preceding or following Examples as active ingredient, are prepared as follows:

| Composition | |
|---|---|
| Active ingredient | 250 g |
| Lauroglycol | 2 liters |

Preparation process: The powdered active ingredient is suspended in Lauroglykol® (propylene glycol laurate, Gattefossé S. A., Saint Priest, France) and ground in a wet-pulveriser to a particle size of about 1 to 3 μm. Portions of in each case 0.419 g of the mixture are then transferred to soft gelatine capsules by means of a capsule-filling machine.

Example 20

Soft Capsules 5000 soft gelatine capsules, each of which contains 0.05 g of one of the compounds of the formula I, II or III mentioned in the preceding or following Examples as active ingredient, are prepared as follows:

| Composition | |
|---|---|
| Active ingredient | 250 g |
| PEG 400 | 1 liter |
| Tween 80 | 1 liter |

Preparation process: The powdered active ingredient is suspended in PEG 400 (polyethylene glycol of Mw between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

The invention claimed is:

1. A therapeutic composition containing substitution derivatives of $N^6$-benzyladenosine, selected from the group comprising 6-(2-acetylbenzylamino)purine riboside, 6-(3-acetylbenzylamino)purine riboside, 6-(4-acetylbenzylamino)purine riboside, 6-(2-acetoxybenzylamino)purine riboside, 6-(3-acetoxybenzylamino)purine riboside, 6-(4-acetoxybenzylamino)purine riboside, 6-(2-sulphobenzylamino)purine riboside, 6-(3-sulphoobenzylamino)purine riboside, 6-(4-sulphobenzylamino)purine riboside, 6-(4-methylaminobenzylamino)purine riboside, 6-(4-hexylbenzylamino)purine riboside, 6-(4-hexyloxybenzylamino)purine riboside, 6-(2-formylbenzylamino)purine riboside, 6-(3-formylbenzylamino)purine riboside, 6-(4-formylbenzylamino)purine riboside, 6-(2-ethoxybenzylamino)purine riboside, 6-(3-ethoxybenzylamino)purine riboside, 6-(4-ethoxybenzylamino)purine riboside, 6-(4-ethylbenzylamino)purine riboside, 6-(4-pentylbenzylamino)purine riboside, 6-(4-pentyloxybenzylamino)purine riboside, 6-(4-phenoxybenzylamino)purine riboside, 6-(4-propylbenzylamino)purine riboside, 6-(4-propyloxybenzylamino)purine riboside, 6-(4-octylbenzylamino)purine riboside, 6-(4-octyloxybenzylamino)purine riboside, 6-(2,5-diaminobenzylamino)purine riboside, 6-(2,5-dihydroxybenzylamino)purine riboside, 6-(2,6-dihydroxybenzylamino)purine riboside, 6-(2-hydroxy-3-methoxybenzylamino)purine riboside, 6-(2-hydroxy-4-methoxybenzylamino)purine riboside, 6-(2-hydroxy-5-methoxybenzylamino)purine riboside, 6-(2-hydroxy-6-methoxybenzylamino)purine riboside, 6-(3-hydroxy-2-methoxybenzylamino)purine riboside, 6-(3-hydroxy-4-methoxybenzylamino)purine riboside, 6-(3-hydroxy-5-methoxybenzylamino)purine riboside, 6-(3-hydroxy-6-methoxybenzylamino)purine riboside, 6-(4-hydroxy-2-methoxybenzylamino)purine riboside, 6-(4-hydroxy-3-methoxybenzylamino)purine riboside, 6-(4-hydroxy-5-methoxybenzylamino)purine riboside, 6-(4-hydroxy-6-methoxybenzylamino)purine riboside, 6-(2-hydroxy-3,4-dimethoxybenzylamino)purine riboside, 6-(2-hydroxy-3,5-dimethoxybenzylamino)purine riboside, 6-(2-hydroxy-3,6-dimethoxybenzylamino)purine riboside, 6-(2-hydroxy-4,5-dimethoxybenzylamino)purine riboside, 6-(2-hydroxy-4,6-dimethoxybenzylamino)purine riboside, 6-(2-hydroxy-5,6-dimethoxybenzylamino)purine riboside, 6-(3-hydroxy-4,5-dimethoxybenzylamino)purine riboside, 6-(3-hydroxy-4,6-dimethoxybenzylamino)purine riboside, 6-(3-hydroxy-2,4-dimethoxybenzylamino)purine riboside, 6-(3-hydroxy-2,5-dimethoxybenzylamino)purine riboside, 6-(3-hydroxy-2,6-dimethoxybenzylamino)purine riboside, 6-(4-hydroxy-2,3-dimethoxybenzylamino)purine riboside, 6-(4-hydroxy-2,5-dimethoxybenzylamino)purine riboside, 6-(4-hydroxy-2,6-dimethoxybenzylamino)purine riboside, 6-(4-hydroxy-3,5-dimethoxybenzylamino)purine riboside, 6-(4-hydroxy-3,6-dimethoxybenzylamino)purine riboside, 6-(2,3-dihydroxy-4-methoxybenzylamino)purine riboside, 6-(2,3-dihydroxy-5-methoxybenzylamino)purine riboside, 6-(2,3-dihydroxy-6-methoxybenzylamino)purine riboside, 6-(2,4-dihydroxy-3-methoxybenzylamino)purine riboside, 6-(2,4-dihydroxy-5-methoxybenzylamino)purine riboside, 6-(2,4-dihydroxy-6-methoxybenzylamino)purine riboside, 6-(2,5-dihydroxy-3-methoxybenzylamino)purine riboside, 6-(2,5-dihydroxy-4-methoxybenzylamino)purine riboside, 6-(2,5-dihydroxy-6-methoxybenzylamino)purine riboside, 6-(2,6-dihydroxy-3-methoxybenzylamino)purine riboside, 6-(2,6-dihydroxy-4-methoxybenzylamino)purine riboside, 6-(2,6-dihydroxy-5-methoxybenzylamino)purine riboside, 6-(3,4-dihydroxy-2-methoxybenzylamino)purine riboside, 6-(3,4-dihydroxy-5-methoxybenzylamino)purine riboside, 6-(3,4-dihydroxy-6-methoxybenzylamino)purine riboside, 6-(3,5-dihydroxy-2-methoxybenzylamino)purine riboside, 6-(3,5-dihydroxy-4-methoxybenzylamino)purine riboside, 6-(3,5-dihydroxy-6-methoxybenzylamino)purine riboside, 6-(2-hydroxy-3,4,5-trimethoxybenzylamino)purine riboside, 6-(2-hydroxy-3,4,6-trimethoxybenzylamino)purine riboside, 6-(2-hydroxy-4,5,6-trimethoxybenzylamino)purine riboside, 6-(2,3,4-trihydroxybenzylamino)purine riboside, 6-(2,4,6-trihydroxybenzylamino)purine riboside, 6-(2,3,4-trihydroxybenzylamino)purine riboside, 6-(3,4,5-trihydroxybenzylamino)purine riboside, 6-(2,4,6-tri hydroxybenzylamino)purine riboside, 6-(2-hydroxy-3-chlorobenzylamino)purine riboside, 6-(2-hydroxy-4-chlorobenzylamino)purine riboside, 6-(2-hydroxy-5-chlorobenzylamino)purine riboside, 6-(2-hydroxy-6-chlorobenzylamino)purine riboside, 6-(2-hydroxy-3-iodobenzylamino)purine riboside, 6-(2-hydroxy-4-iodobenzylamino)purine riboside, 6-(2-hydroxy-5-iodobenzylamino)purine riboside, 6-(2-hydroxy-6- iodobenzylamino)purine riboside, 6-(2-hydroxy-3-bromobenzylamino)purine riboside, 6-(2-hydroxy-4-bromobenzylamino)purine riboside, 6-(2-hydroxy-5-bromobenzylamino)purine riboside, 6-(2-hydroxy-6-bromobenzylamino)purine riboside, 6-(2-hydroxy-3-fluorobenzylamino)purine riboside, 6-(2-hydroxy-4-fluorobenzylamino)purine riboside, 6-(2-hydroxy-5-fluorobenzylamino)purine riboside, 6-(2-hydroxy-6-fluorobenzylamino)purine riboside, 6-(2-hydroxy-3-methylbenzylamino)purine riboside, 6-(2-hydroxy-4-methylbenzylamino)purine riboside, 6-(2-hydroxy-5-methylbenzylamino)purine riboside, 6-(2-hydroxy-6-methylbenzylamino)purine riboside, 6-(2,3-dihydroxy-4-chlorobenzylamino)purine riboside, 6-(2,3-dihydroxy-5-chlorobenzylamino)purine riboside, 6-(2,5-dihydroxy-4-chlorobenzylamino)purine riboside, 6-(2,6-dihydroxy-4-chlorobenzylamino)purine riboside, 6-(2,6-dihydroxy-4-bromoxybenzylamino)purine riboside, 6-(2,6-dihydroxy-4-iodobenzylamino)purine riboside, 6-(2,6-dihydroxy-3-chlorobenzylamino)purine riboside, 6-(2,6-dihydroxy-3-bromobenzylamino)purine riboside, 6-(2,6-dihydroxy-3-iodobenzylamino)purine riboside, 6-(2,6-dihydroxy-3-fluorobenzylamino)purine riboside, 6-(2,6-dihydroxy-3,5-dichlorobenzylamino)purine riboside, 6-(2,6-dihydroxy-3,5-dibromobenzylamino)purine riboside, 6-(2,6-dihydroxy-3,5-diiodobenzylamino)purine riboside, 6-(2,6-dihydroxy-3,5-difluorobenzylamino)purine riboside, and their pharmaceutically acceptable salts with alkali metals, ammonium or amines, in the form of racemates or optically active isomers, as well as their addition salts with acids.

2. A pharmaceutical composition, containing a substitution derivative of N6-benzyladenosine according to claim 1, or its pharmaceutically acceptable salt, including a pharmaceutical carrier.

3. A cosmetic composition, containing a substitution derivative of N6-benzyladenosine according to claim 1, or its pharmaceutically acceptable salt, including a pharmaceutical carrier.

4. A pharmaceutical composition containing a compound according to claim 1, including a pharmaceutical carrier, suitable as mitotic or antimitotic compound.

* * * * *